United States Patent
Fangrow et al.

(10) Patent No.: US 9,168,366 B2
(45) Date of Patent: Oct. 27, 2015

(54) MEDICAL CONNECTOR WITH CLOSEABLE LUER CONNECTOR

(71) Applicant: ICU Medical, Inc., San Clemente, CA (US)

(72) Inventors: Thomas F. Fangrow, Mission Viejo, CA (US); Bruce Hubrecht, Canyon Lake, CA (US); Harold Anderson, Wildomar, CA (US); Christopher Lopez, Laguna Beach, CA (US)

(73) Assignee: ICU Medical, Inc., San Clemente, CA (US)

( * ) Notice: Subject to any disclaimer, the term of this patent is extended or adjusted under 35 U.S.C. 154(b) by 5 days.

(21) Appl. No.: 14/177,548

(22) Filed: Feb. 11, 2014

(65) Prior Publication Data
US 2014/0303601 A1  Oct. 9, 2014

Related U.S. Application Data

(63) Continuation-in-part of application No. 13/100,508, filed on May 4, 2011, now Pat. No. 8,647,310, which is a continuation-in-part of application No. 12/641,283, filed on Dec. 17, 2009, now Pat. No. 8,679,090.

(60) Provisional application No. 61/332,103, filed on May 6, 2010, provisional application No. 61/139,514, filed on Dec. 19, 2008.

(51) Int. Cl.
A61M 5/315   (2006.01)
A61M 39/10   (2006.01)
A61M 39/26   (2006.01)

(52) U.S. Cl.
CPC ............... *A61M 39/10* (2013.01); *A61M 39/26* (2013.01); *A61M 2039/261* (2013.01); *A61M 2039/267* (2013.01); *A61M 2039/268* (2013.01)

(58) Field of Classification Search
CPC .................. A61M 2039/261; A61M 2039/268; A61M 39/10; A61M 39/26
USPC ........................................ 604/236; 251/149.2
See application file for complete search history.

(56) References Cited

U.S. PATENT DOCUMENTS 2,842,382 A   7/1958   Franck
2,931,668 A   4/1960   Baley
(Continued)

FOREIGN PATENT DOCUMENTS

EP   0 791 371   8/1997
EP   1 946 792   7/2008
(Continued)

OTHER PUBLICATIONS

U.S. Appl. No. 14/470,647, filed Aug. 27, 2014, Fangrow, Jr. et al.
(Continued)

*Primary Examiner* — Kevin C Sirmons
*Assistant Examiner* — Deanna K Hall
(74) *Attorney, Agent, or Firm* — Knobbe Martens Olson & Bear, LLP

(57) ABSTRACT

Some embodiments relate to a luer connector comprising a housing having a hollow bore therethrough, a first end, and a second end, a male luer tip supported by the housing configured to rotate with respect to the housing, the luer tip having a first open end and a passageway through the luer tip in fluid communication with the first open end, and a substantially rigid internal member extending into the passageway of the luer tip toward the first open end of the luer tip. In some embodiments, at least one of the luer tip and the internal member can be axially moveable between a first closed position and a second open position relative to the other of the luer tip and the internal member. Further, the luer tip and the internal member can cooperate such that rotation of the luer tip in a first direction relative to the housing increases an axial displacement between the first open end of the luer tip and an end portion of the internal member.

9 Claims, 35 Drawing Sheets

(56) References Cited

U.S. PATENT DOCUMENTS

| | | |
|---|---|---|
| 2,968,497 A | 1/1961 | Treleman |
| 3,127,892 A | 4/1964 | Bellamy, Jr. et al. |
| 3,304,047 A | 2/1967 | Martin |
| 3,334,860 A | 8/1967 | Bolton, Jr. |
| 3,707,972 A | 1/1973 | Villari et al. |
| 3,729,031 A | 4/1973 | Baldwin |
| 3,986,508 A | 10/1976 | Barrington |
| 4,055,179 A | 10/1977 | Manschot et al. |
| 4,066,067 A | 1/1978 | Micheli |
| 4,076,285 A | 2/1978 | Martinez |
| 4,080,965 A | 3/1978 | Phillips |
| 4,084,606 A | 4/1978 | Mittleman |
| 4,121,585 A | 10/1978 | Becker, Jr. |
| 4,133,441 A | 1/1979 | Mittleman et al. |
| 4,143,853 A | 3/1979 | Abramson |
| 4,150,845 A | 4/1979 | Kopacz et al. |
| 4,195,632 A | 4/1980 | Parker et al. |
| 4,233,982 A | 11/1980 | Bauer et al. |
| 4,245,635 A | 1/1981 | Kontos |
| 4,324,239 A | 4/1982 | Gordon et al. |
| 4,334,551 A | 6/1982 | Pfister |
| 4,340,049 A | 7/1982 | Munsch |
| 4,379,458 A | 4/1983 | Bauer et al. |
| 4,387,879 A | 6/1983 | Tauschinski |
| 4,397,442 A | 8/1983 | Larkin |
| 4,430,073 A | 2/1984 | Bemis et al. |
| 4,436,125 A | 3/1984 | Blenkush |
| 4,452,473 A | 6/1984 | Ruschke |
| 4,457,749 A | 7/1984 | Bellotti et al. |
| 4,511,359 A | 4/1985 | Vaillancourt |
| 4,538,836 A | 9/1985 | Kruetten |
| 4,610,469 A | 9/1986 | Wolff-Mooij |
| 4,619,640 A | 10/1986 | Potolsky et al. |
| 4,623,332 A | 11/1986 | Lindmayer et al. |
| 4,629,159 A | 12/1986 | Wellenstam |
| 4,660,803 A | 4/1987 | Johnston et al. |
| 4,662,878 A | 5/1987 | Lindmayer |
| 4,700,744 A | 10/1987 | Rutter et al. |
| 4,723,603 A | 2/1988 | Plummer |
| 4,728,075 A | 3/1988 | Paradis |
| 4,745,950 A | 5/1988 | Mathieu |
| 4,774,964 A | 10/1988 | Bonaldo |
| 4,774,965 A | 10/1988 | Rodriguez et al. |
| 4,781,702 A | 11/1988 | Herrli |
| 4,804,015 A | 2/1989 | Albinsson |
| 4,816,024 A | 3/1989 | Sitar et al. |
| 4,834,271 A | 5/1989 | Litwin |
| 4,862,913 A | 9/1989 | Wildfang |
| 4,883,483 A | 11/1989 | Lindmayer |
| 4,915,687 A | 4/1990 | Sivert |
| 4,917,669 A | 4/1990 | Bonaldo |
| 4,935,010 A | 6/1990 | Cox et al. |
| 4,950,260 A | 8/1990 | Bonaldo |
| 4,969,879 A | 11/1990 | Lichte |
| D313,277 S | 12/1990 | Haining |
| D314,050 S | 1/1991 | Sone |
| 5,006,114 A | 4/1991 | Rogers et al. |
| 5,021,059 A | 6/1991 | Kensey et al. |
| 5,047,021 A | 9/1991 | Utterberg |
| 5,053,015 A | 10/1991 | Gross |
| 5,065,783 A | 11/1991 | Ogle, II |
| 5,070,885 A | 12/1991 | Bonaldo |
| 5,098,385 A | 3/1992 | Walsh |
| 5,108,376 A | 4/1992 | Bonaldo |
| 5,122,123 A | 6/1992 | Vaillancourt |
| 5,139,483 A | 8/1992 | Ryan |
| 5,147,333 A | 9/1992 | Raines |
| 5,154,703 A | 10/1992 | Bonaldo |
| RE34,223 E | 4/1993 | Bonaldo |
| 5,199,948 A | 4/1993 | McPhee |
| 5,201,725 A | 4/1993 | Kling |
| 5,203,775 A | 4/1993 | Frank et al. |
| 5,211,634 A | 5/1993 | Vaillancourt |
| 5,215,537 A | 6/1993 | Lynn et al. |
| 5,215,538 A | 6/1993 | Larkin |
| 5,224,939 A | 7/1993 | Holman et al. |
| 5,242,393 A | 9/1993 | Brimhall et al. |
| 5,242,425 A | 9/1993 | White et al. |
| 5,251,873 A | 10/1993 | Atkinson et al. |
| 5,269,771 A | 12/1993 | Thomas et al. |
| 5,273,533 A | 12/1993 | Bonaldo |
| 5,279,571 A | 1/1994 | Larkin |
| 5,281,206 A | 1/1994 | Lopez |
| 5,284,475 A | 2/1994 | Mackal |
| 5,295,657 A | 3/1994 | Atkinson |
| 5,301,686 A | 4/1994 | Newman |
| 5,306,243 A | 4/1994 | Bonaldo |
| 5,312,377 A | 5/1994 | Dalton |
| 5,322,518 A | 6/1994 | Schneider et al. |
| 5,324,270 A | 6/1994 | Kayan et al. |
| 5,330,450 A | 7/1994 | Lopez |
| 5,334,159 A | 8/1994 | Turkel |
| 5,344,414 A | 9/1994 | Lopez et al. |
| 5,360,413 A | 11/1994 | Leason et al. |
| 5,370,636 A | 12/1994 | Von Witzleben |
| 5,380,306 A | 1/1995 | Brinon |
| 5,385,372 A | 1/1995 | Utterberg |
| 5,390,898 A | 2/1995 | Smedley et al. |
| 5,391,150 A | 2/1995 | Richmond |
| 5,395,348 A | 3/1995 | Ryan |
| 5,397,314 A | 3/1995 | Farley et al. |
| 5,400,500 A | 3/1995 | Behnke et al. |
| 5,401,245 A | 3/1995 | Haining |
| 5,402,826 A | 4/1995 | Molnar et al. |
| 5,402,982 A | 4/1995 | Atkinson et al. |
| 5,405,323 A | 4/1995 | Rogers et al. |
| 5,405,331 A | 4/1995 | Behnke et al. |
| 5,405,333 A | 4/1995 | Richmond |
| 5,411,499 A | 5/1995 | Dudar et al. |
| 5,417,673 A | 5/1995 | Gordon |
| 5,423,791 A | 6/1995 | Bartlett |
| 5,425,465 A | 6/1995 | Healy |
| 5,433,330 A | 7/1995 | Yatsko et al. |
| 5,439,451 A | 8/1995 | Collinson et al. |
| 5,441,487 A | 8/1995 | Vedder |
| 5,445,623 A | 8/1995 | Richmond |
| 5,456,668 A | 10/1995 | Ogle, II |
| 5,456,675 A | 10/1995 | Wolbring et al. |
| 5,462,255 A | 10/1995 | Rosen et al. |
| 5,464,399 A | 11/1995 | Boettger |
| 5,470,319 A | 11/1995 | Mayer |
| 5,470,327 A | 11/1995 | Helgren et al. |
| 5,474,536 A | 12/1995 | Bonaldo |
| 5,480,393 A | 1/1996 | Bommarito |
| 5,492,147 A | 2/1996 | Challender et al. |
| 5,501,426 A | 3/1996 | Atkinson et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,527,284 A | 6/1996 | Ohnemus et al. |
| 5,533,708 A | 7/1996 | Atkinson et al. |
| 5,533,983 A | 7/1996 | Haining |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| 5,552,118 A | 9/1996 | Mayer |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,616,129 A | 4/1997 | Mayer |
| 5,616,130 A | 4/1997 | Mayer |
| RE35,539 E | 6/1997 | Bonaldo |
| 5,643,224 A | 7/1997 | Szapiro et al. |
| 5,645,538 A | 7/1997 | Richmond |

(56) References Cited

U.S. PATENT DOCUMENTS

| | | |
|---|---|---|
| 5,658,260 A | 8/1997 | Desecki et al. |
| 5,674,206 A | 10/1997 | Allton et al. |
| 5,676,346 A | 10/1997 | Leinsing |
| 5,685,866 A | 11/1997 | Lopez |
| 5,685,868 A | 11/1997 | Lundquist |
| 5,699,821 A | 12/1997 | Paradis |
| 5,700,248 A | 12/1997 | Lopez |
| 5,702,374 A | 12/1997 | Johnson |
| 5,709,243 A | 1/1998 | Wells et al. |
| 5,735,826 A | 4/1998 | Richmond |
| 5,738,144 A | 4/1998 | Rogers |
| 5,741,084 A | 4/1998 | Del Rio et al. |
| 5,749,861 A | 5/1998 | Guala et al. |
| RE35,841 E | 7/1998 | Frank et al. |
| 5,782,816 A | 7/1998 | Werschmidt et al. |
| 5,785,693 A | 7/1998 | Haining |
| 5,806,831 A | 9/1998 | Paradis |
| 5,814,024 A | 9/1998 | Thompson et al. |
| 5,820,601 A | 10/1998 | Mayer |
| 5,830,195 A | 11/1998 | Peters et al. |
| 5,839,715 A | 11/1998 | Leinsing |
| 5,848,994 A | 12/1998 | Richmond |
| 5,855,568 A | 1/1999 | Battiato et al. |
| 5,947,954 A | 9/1999 | Bonaldo |
| 5,984,373 A | 11/1999 | Fitoussi et al. |
| 6,029,946 A | 2/2000 | Doyle |
| 6,036,171 A | 3/2000 | Weinheimer et al. |
| 6,050,978 A | 4/2000 | Orr et al. |
| 6,063,062 A | 5/2000 | Paradis |
| 6,068,011 A | 5/2000 | Paradis |
| 6,068,617 A | 5/2000 | Richmond |
| 6,079,432 A | 6/2000 | Paradis |
| 6,106,502 A | 8/2000 | Richmond |
| 6,113,068 A | 9/2000 | Ryan |
| 6,142,446 A | 11/2000 | Leinsing |
| 6,152,913 A | 11/2000 | Feith et al. |
| 6,168,137 B1 | 1/2001 | Paradis |
| 6,171,287 B1 | 1/2001 | Lynn et al. |
| 6,183,464 B1 | 2/2001 | Sharp et al. |
| 6,189,859 B1 | 2/2001 | Rohrbough et al. |
| 6,206,860 B1 | 3/2001 | Richmond |
| 6,224,578 B1 | 5/2001 | Davis et al. |
| 6,224,588 B1 | 5/2001 | Jentzen |
| 6,231,552 B1 | 5/2001 | Jentzen |
| 6,242,393 B1 | 6/2001 | Ishida et al. |
| 6,245,048 B1 | 6/2001 | Fangrow et al. |
| 6,290,206 B1 | 9/2001 | Doyle |
| 6,299,132 B1 | 10/2001 | Weinheimer et al. |
| 6,332,633 B1 | 12/2001 | Fitoussi et al. |
| 6,402,207 B1 | 6/2002 | Segal et al. |
| 6,428,520 B1 | 8/2002 | Lopez |
| 6,431,219 B1 | 8/2002 | Redler et al. |
| 6,485,472 B1 | 11/2002 | Richmond |
| 6,499,719 B1 | 12/2002 | Clancy et al. |
| 6,508,792 B2 | 1/2003 | Szames et al. |
| 6,508,807 B1 | 1/2003 | Peters |
| 6,541,802 B2 | 4/2003 | Doyle |
| 6,543,745 B1 | 4/2003 | Enerson |
| 6,581,906 B2 | 6/2003 | Pott et al. |
| 6,585,229 B2 | 7/2003 | Cote et al. |
| 6,595,964 B2 | 7/2003 | Finley et al. |
| 6,595,981 B2 | 7/2003 | Huet |
| 6,609,696 B2 | 8/2003 | Enerson |
| 6,612,624 B1 | 9/2003 | Segal et al. |
| 6,666,852 B2 | 12/2003 | Niedospial, Jr. |
| 6,695,817 B1 | 2/2004 | Fangrow |
| 6,745,998 B2 | 6/2004 | Doyle |
| 6,840,501 B2 | 1/2005 | Doyle |
| 6,869,426 B2 | 3/2005 | Ganem |
| 6,875,205 B2 | 4/2005 | Leinsing |
| 6,899,315 B2 | 5/2005 | Maiville et al. |
| 6,911,025 B2 | 6/2005 | Miyahara |
| 6,955,669 B2 | 10/2005 | Curutcharry |
| 6,964,406 B2 | 11/2005 | Doyle |
| 6,991,608 B2 | 1/2006 | Young et al. |
| 7,004,934 B2 | 2/2006 | Vaillancourt |
| 7,037,302 B2 | 5/2006 | Vaillancourt |
| 7,040,598 B2 | 5/2006 | Raybuck |
| 7,044,441 B2 | 5/2006 | Doyle |
| 7,100,891 B2 | 9/2006 | Doyle |
| 7,125,396 B2 | 10/2006 | Leinsing et al. |
| 7,137,654 B2 | 11/2006 | Segal et al. |
| 7,140,592 B2 | 11/2006 | Phillips |
| 7,182,313 B2 | 2/2007 | Doyle |
| 7,195,228 B2 | 3/2007 | Tiberghien et al. |
| 7,244,249 B2 | 7/2007 | Leinsing et al. |
| 7,306,197 B2 | 12/2007 | Parrino et al. |
| 7,306,198 B2 | 12/2007 | Doyle |
| 7,306,566 B2 | 12/2007 | Raybuck |
| 7,347,458 B2 | 3/2008 | Rome et al. |
| 7,350,764 B2 | 4/2008 | Raybuck |
| 7,361,164 B2 | 4/2008 | Simpson et al. |
| 7,497,484 B2 | 3/2009 | Ziman |
| 7,559,530 B2 | 7/2009 | Korogi et al. |
| 7,588,563 B2 | 9/2009 | Guala |
| 7,600,515 B2 | 10/2009 | Matlock |
| 7,645,274 B2 | 1/2010 | Whitley |
| 7,651,481 B2 | 1/2010 | Raybuck |
| 7,666,170 B2 | 2/2010 | Guala |
| 7,717,874 B2 | 5/2010 | Landau et al. |
| 7,758,566 B2 | 7/2010 | Simpson et al. |
| 7,762,524 B2 | 7/2010 | Cawthon et al. |
| 7,766,304 B2 | 8/2010 | Phillips |
| 7,766,897 B2 | 8/2010 | Ramsey et al. |
| 7,803,139 B2 | 9/2010 | Fangrow, Jr. |
| 7,803,140 B2 | 9/2010 | Fangrow, Jr. |
| 7,815,614 B2 | 10/2010 | Fangrow, Jr. |
| 7,837,658 B2 | 11/2010 | Cote et al. |
| 7,857,805 B2 | 12/2010 | Raines |
| 7,976,532 B2 | 7/2011 | Kitani et al. |
| 7,998,134 B2 | 8/2011 | Fangrow et al. |
| 8,066,692 B2 | 11/2011 | Simpson et al. |
| 8,211,069 B2 | 7/2012 | Fangrow, Jr. |
| 8,251,346 B2 | 8/2012 | Stroup |
| 8,262,628 B2 | 9/2012 | Fangrow, Jr. |
| 8,372,059 B2 | 2/2013 | Ziman |
| 8,408,226 B2 | 4/2013 | Raines et al. |
| 8,556,868 B2 | 10/2013 | Simpson et al. |
| 8,647,310 B2 | 2/2014 | Fangrow, Jr. et al. |
| 8,679,090 B2 | 3/2014 | Anderson et al. |
| 8,721,628 B2 | 5/2014 | Ziman |
| 8,777,090 B2 | 7/2014 | Miller et al. |
| 8,777,908 B2 | 7/2014 | Fangrow, Jr. |
| 8,777,931 B2 | 7/2014 | Davis et al. |
| 2001/0029355 A1 | 10/2001 | Szames et al. |
| 2002/0066715 A1 | 6/2002 | Niedospial, Jr. |
| 2002/0082586 A1 | 6/2002 | Finley et al. |
| 2003/0060804 A1 | 3/2003 | Vaillancourt |
| 2003/0066978 A1 | 4/2003 | Enerson |
| 2003/0111623 A1 | 6/2003 | Enerson |
| 2003/0136932 A1 | 7/2003 | Doyle |
| 2003/0208165 A1 | 11/2003 | Christensen et al. |
| 2004/0124388 A1 | 7/2004 | Kiehne |
| 2004/0124389 A1 | 7/2004 | Phillips |
| 2004/0238776 A1 | 12/2004 | Peters et al. |
| 2005/0015075 A1 | 1/2005 | Wright et al. |
| 2005/0033268 A1 | 2/2005 | Decaria |
| 2005/0124942 A1 | 6/2005 | Richmond |
| 2005/0212292 A1 | 9/2005 | Parrino et al. |
| 2005/0228362 A1 | 10/2005 | Vaillancourt |
| 2005/0245872 A1 | 11/2005 | Simpson et al. |
| 2006/0025751 A1 | 2/2006 | Roy et al. |
| 2006/0058734 A1 | 3/2006 | Phillips |
| 2006/0129109 A1 | 6/2006 | Shaw et al. |
| 2006/0142730 A1 | 6/2006 | Proulx et al. |
| 2006/0142735 A1 | 6/2006 | Whitley |
| 2006/0149213 A1 | 7/2006 | Raybuck |
| 2006/0157984 A1 | 7/2006 | Rome et al. |
| 2006/0161115 A1 | 7/2006 | Fangrow |
| 2006/0192164 A1 | 8/2006 | Korogi et al. |
| 2006/0202146 A1 | 9/2006 | Doyle |
| 2006/0211996 A1 | 9/2006 | Trinchera et al. |
| 2006/0253084 A1 | 11/2006 | Nordgren |
| 2007/0073270 A1 | 3/2007 | Christensen et al. |

(56) References Cited

U.S. PATENT DOCUMENTS

| | | |
|---|---|---|
| 2007/0088292 A1 | 4/2007 | Fangrow |
| 2007/0088293 A1 | 4/2007 | Fangrow |
| 2007/0088294 A1 | 4/2007 | Fangrow |
| 2007/0088324 A1 | 4/2007 | Fangrow, Jr. |
| 2007/0088327 A1 | 4/2007 | Guala |
| 2007/0179453 A1 | 8/2007 | Lim et al. |
| 2007/0179454 A1 | 8/2007 | Ziman et al. |
| 2008/0103485 A1 | 5/2008 | Kruger |
| 2008/0125756 A1 | 5/2008 | Dicarlo et al. |
| 2008/0140020 A1 | 6/2008 | Shirley |
| 2008/0190485 A1 | 8/2008 | Guala |
| 2008/0200900 A1 | 8/2008 | Aeschlimann et al. |
| 2008/0287920 A1 | 11/2008 | Fangrow et al. |
| 2009/0001720 A1 | 1/2009 | Cheon et al. |
| 2010/0211019 A1 | 8/2010 | Greco |
| 2010/0249723 A1 | 9/2010 | Fangrow, Jr. |
| 2011/0046572 A1 | 2/2011 | Fangrow |
| 2011/0074148 A1 | 3/2011 | Imai |
| 2011/0276035 A1 | 11/2011 | Fangrow, Jr. |
| 2011/0306931 A1 | 12/2011 | Kamen et al. |
| 2012/0041391 A1 | 2/2012 | Fangrow et al. |
| 2012/0089101 A1 | 4/2012 | Carlyon et al. |
| 2012/0330247 A1 | 12/2012 | Fangrow, Jr. |
| 2013/0150806 A1 | 6/2013 | Fangrow, Jr. |
| 2013/0193359 A1 | 8/2013 | Yeh |
| 2013/0197453 A1 | 8/2013 | Yeh |
| 2013/0231616 A1 | 9/2013 | Fangrow, Jr. |
| 2013/0304037 A1 | 11/2013 | Fangrow |
| 2013/0317483 A1 | 11/2013 | Reichert et al. |
| 2014/0246616 A1 | 9/2014 | Fangrow |

FOREIGN PATENT DOCUMENTS

| | | |
|---|---|---|
| GB | 2 116 277 | 9/1983 |
| GB | 2 118 440 | 11/1983 |
| GB | 2 353 078 | 2/2001 |
| JP | 11-311234 | 11/1999 |
| WO | WO 01/03756 | 1/2001 |
| WO | WO 2004/060474 | 7/2004 |
| WO | WO 2004/082756 | 9/2004 |
| WO | WO 2006/076656 | 7/2006 |
| WO | WO 2006/088858 | 8/2006 |
| WO | WO 2006/124756 | 11/2006 |
| WO | WO 2013/036854 | 3/2013 |

OTHER PUBLICATIONS

U.S. Appl. No. 11/417,923, filed May 3, 2006, Gustus et al.
U.S. Appl. No. 11/417,671, filed May 3, 2006, Gustus et al.
U.S. Appl. No. 11/417,648, filed May 3, 2006, Gustus et al.
U.S. Appl. No. 11/417,909, filed May 3, 2006, Gustus et al.
U.S. Appl. No. 11/417,882, filed May 3, 2006, Gustus et al.
U.S. Appl. No. 13/606,520, filed Sep. 7, 2012, Fangrow, Jr.
International Search Report and Written Opinion re PCT App. No. PCT/US2011/034854, mailed Mar. 28, 2012.
International Preliminary Report on Patentability re PCT App. No. PCT/US2011/034854, issued Nov. 6, 2012, 2012.
International Search Report and Written Opinion re PCT App. No. PCT/US2009/068857, dated (mailed) Apr. 8, 2010.
International Preliminary Report on Patentability re PCT App. No. PCT/US2009/068857, issued Jun. 21, 2011 in 8 pages.

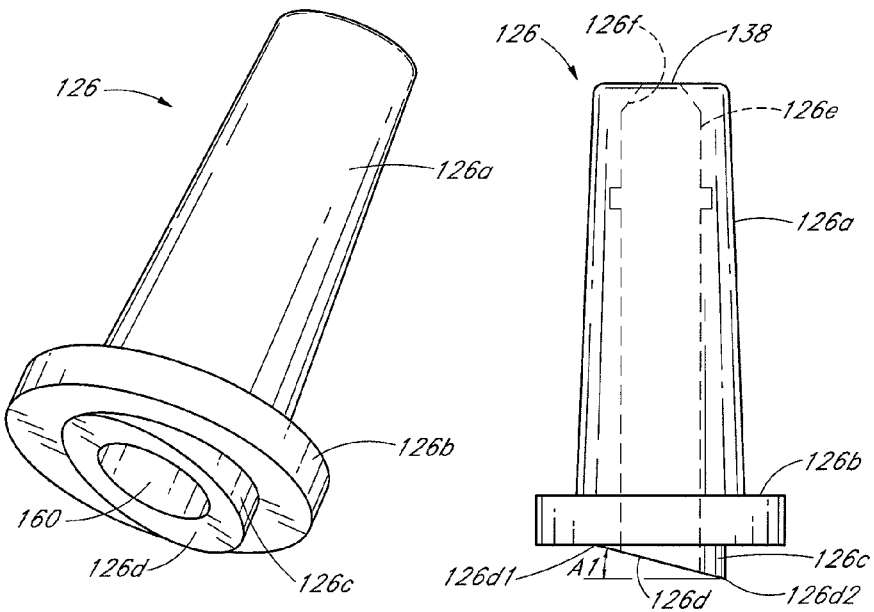
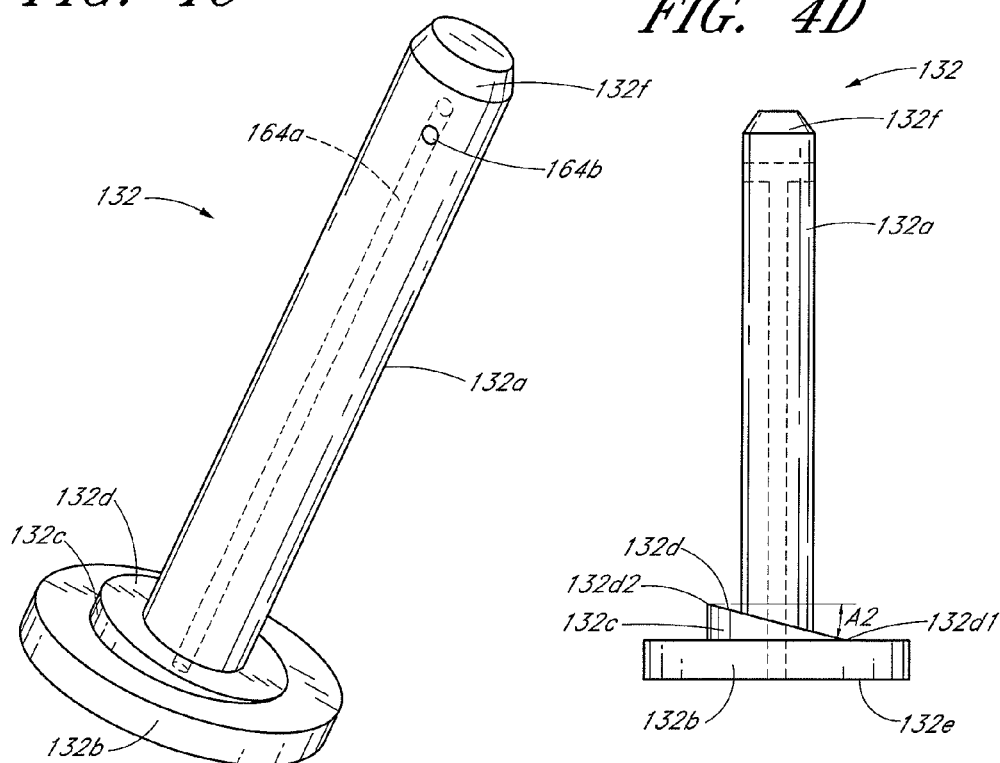
FIG. 4C
FIG. 4D
FIG. 4E
FIG. 4F

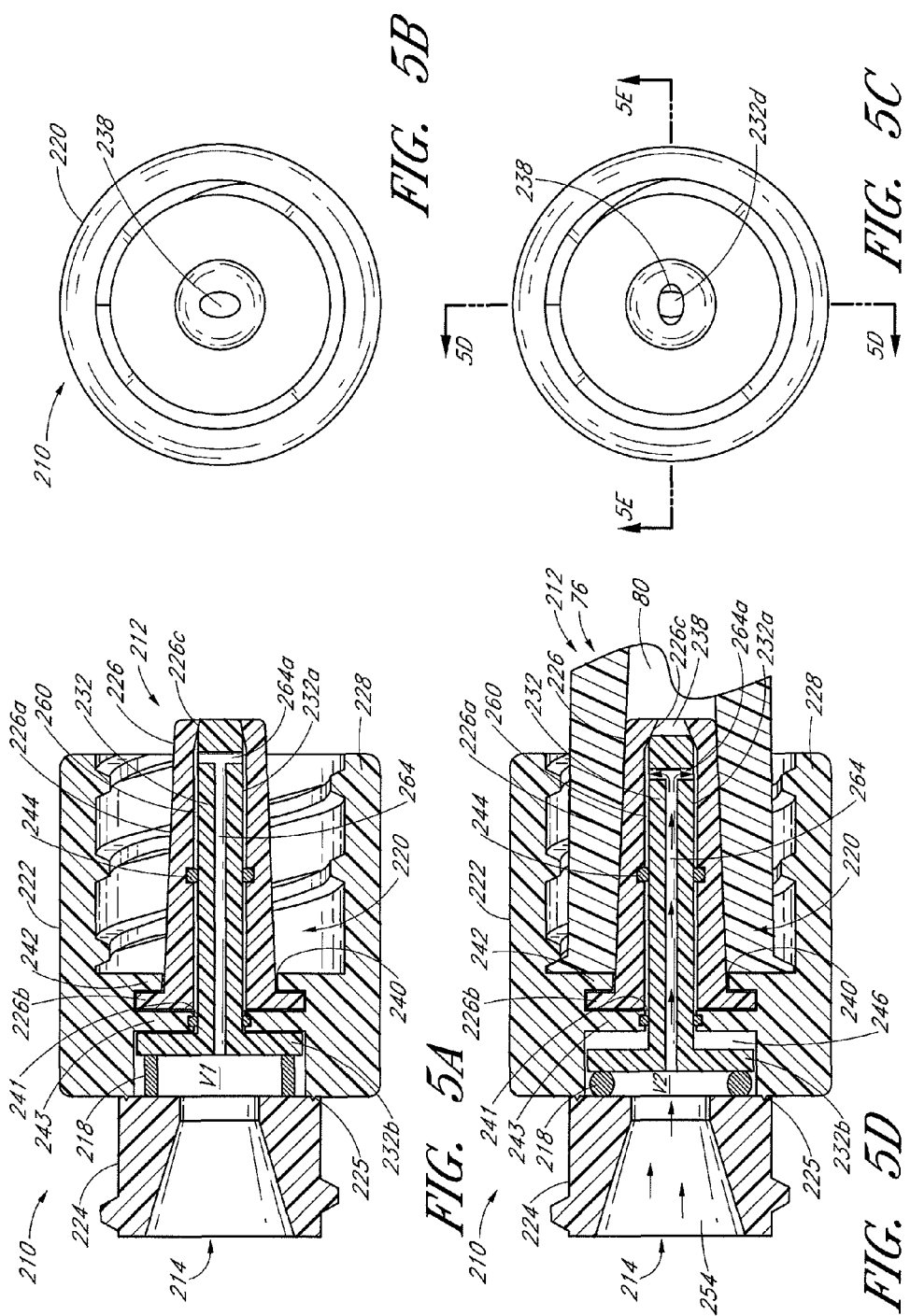

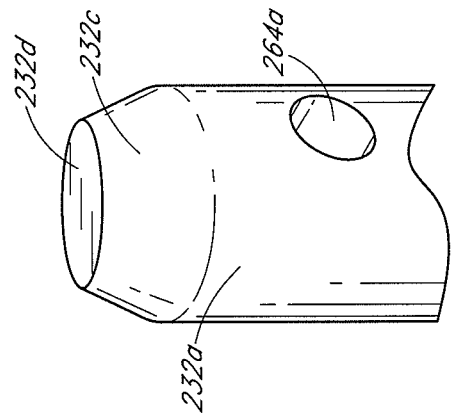
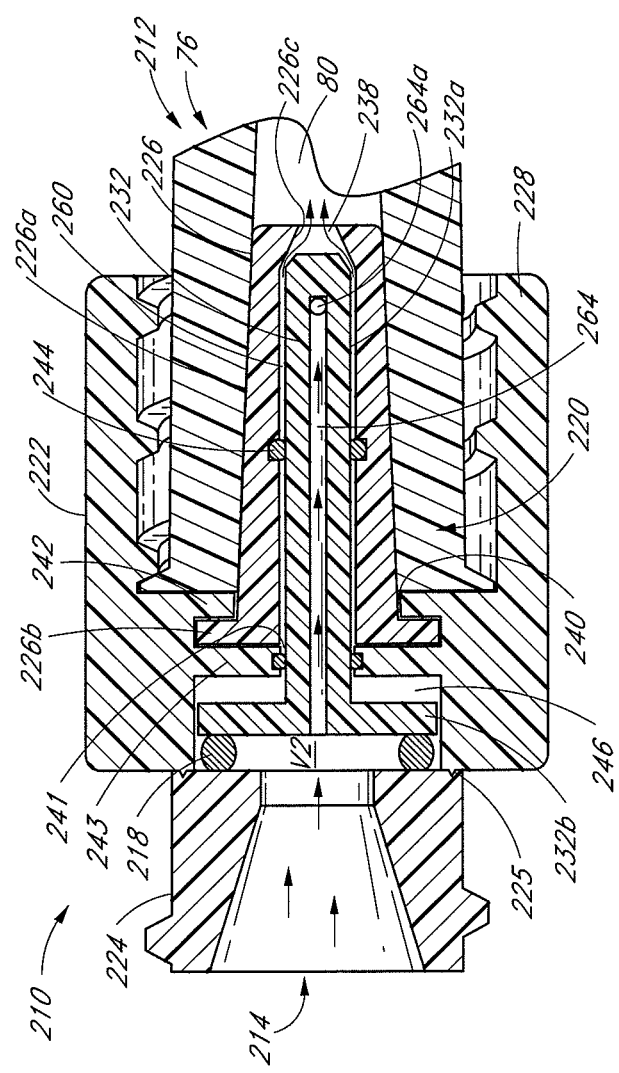
FIG. 5F
FIG. 5E

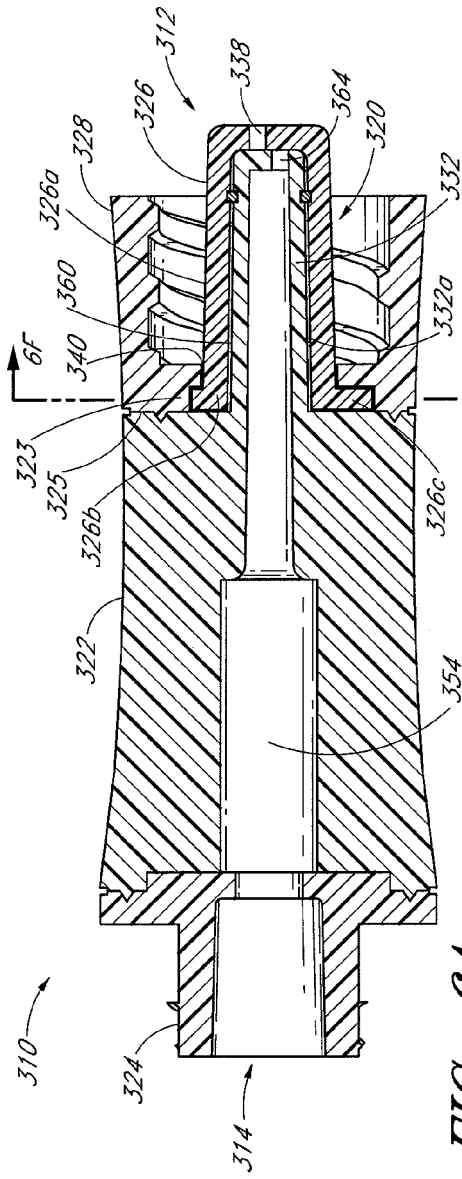
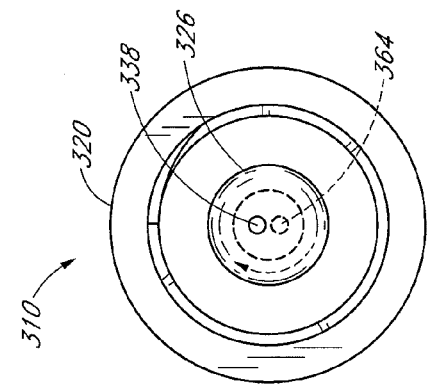
FIG. 6A
FIG. 6C
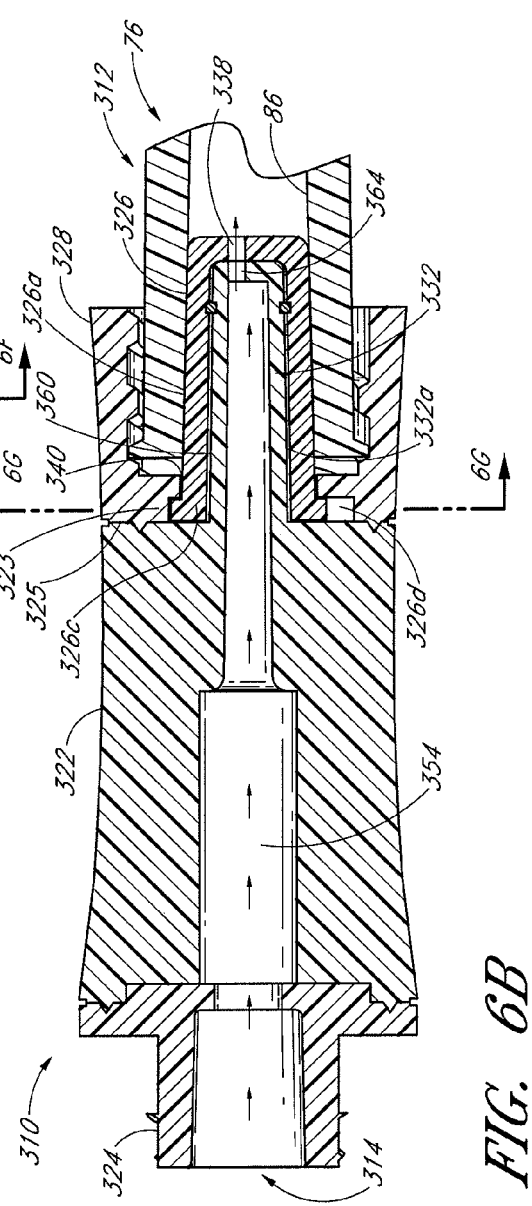
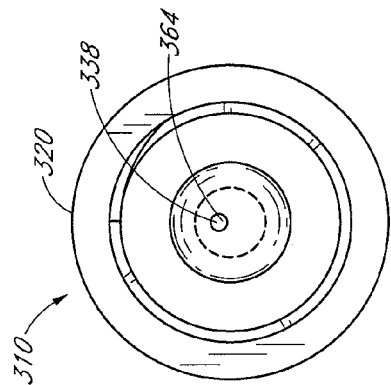
FIG. 6B
FIG. 6D

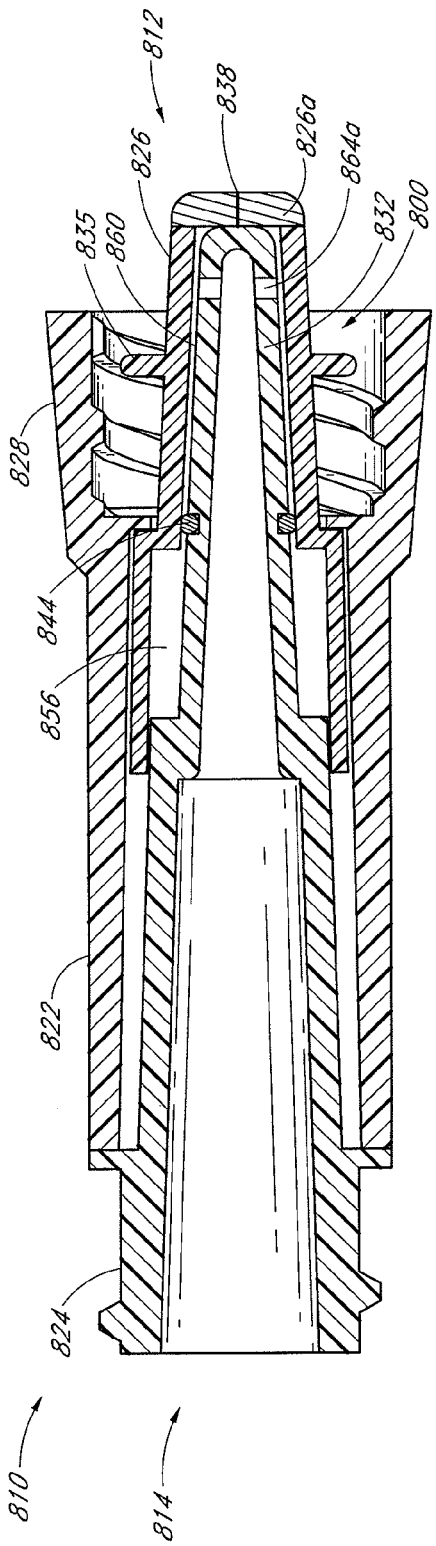
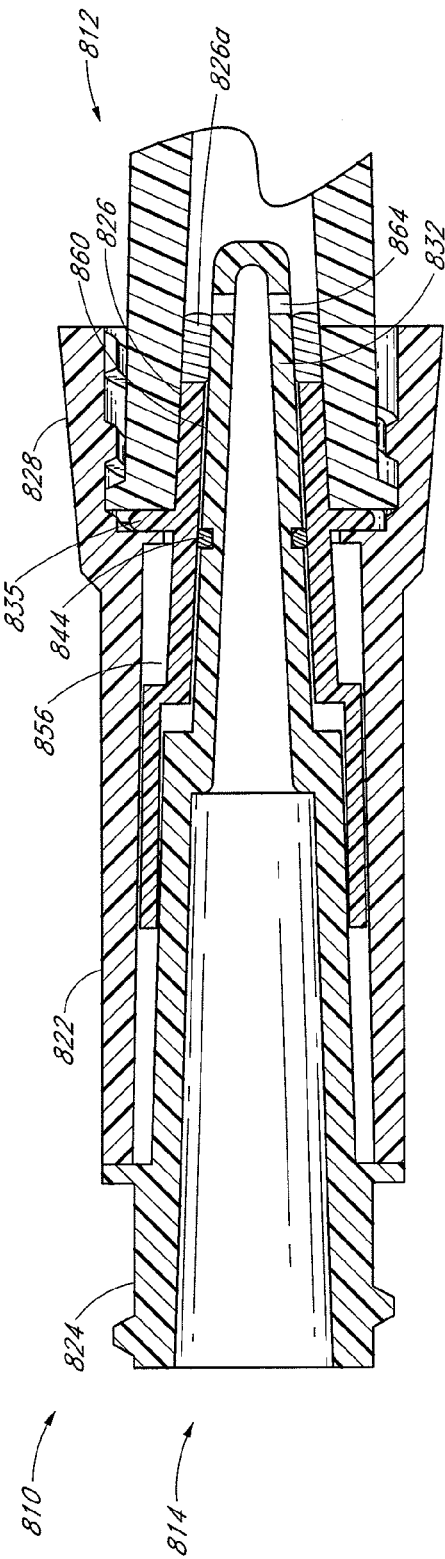
FIG. 11A
FIG. 11B

MEDICAL CONNECTOR WITH CLOSEABLE LUER CONNECTOR

BACKGROUND OF THE DISCLOSURE

Priority Information and Incorporation by Reference

This application is a continuation-in-part of U.S. patent application Ser. No. 13/100,508, filed May 4, 2011, pending, which claims priority benefit of U.S. Provisional Application 61/332,103, filed May 6, 2010, each of which is hereby incorporated by reference in its entirety as if fully set forth herein.

This application is also a continuation-in-part of U.S. patent application Ser. No. 12/641,283, filed Dec. 17, 2009, pending, which claims priority benefit of U.S. Provisional Patent Application No. 61/139,514, filed Dec. 19, 2008, each of which is hereby incorporated by reference in its entirety as if fully set forth herein.

This application also hereby incorporates by reference U.S. Pat. No. 5,685,866, issued Nov. 11, 1997, in its entirety, as if fully set forth herein.

BACKGROUND OF THE INVENTION

1. Field of the Disclosure

Embodiments of this disclosure relate generally to medical connectors through which fluids flow, and in particular, to medical connectors with male luers.

2. Description of the Related Art

Systems of connectors, valves, and tubing are routinely used in hospitals and other medical settings for facilitating the transfer of fluids to and from patients. It is often a challenge to keep such systems sterile and to prevent leakage of fluids when the various components are engaged and disengaged. In order to maintain a barrier to bacteria, debris, and fluid leakage, female connectors often have been provided with closures, such as septa, flexible seals, or other impediments, at their mating ends. When a male luer connector is engaged with the female connector, the closure of the female connector is temporarily opened, pierced, or moved to allow fluid to flow between the two connectors. Male connectors typically employ needles or luers to open, pierce, or move the closure on the female connectors.

In many systems, only the female connectors are automatically blocked from the external environment when disengaged. Male luer connectors are generally not provided with automatic closing mechanisms. Male luer connectors sometimes employ additional components, such as caps, to stop the flow of fluid and impede the entry of bacteria and debris. Because such closure mechanisms are not automatic (or not used at all), male luer connectors are sometimes left unsealed, allowing fluid to drip out. This may increase the risk of unsanitary conditions inside and outside of the fluid transfer system. In addition, in some medical applications such as certain chemotherapy treatments, the fluids in the tubing and connectors can be harmful if released.

Moreover, in the busy environment of hospitals and other medical settings, health care providers must often quickly manipulate multiple medical implements with one hand, making it difficult to retrieve male luer caps and rapidly attach them upon disengagement of male connectors. In addition, male luer connectors are often employed at the downstream end of gravity-fed fluid sources such as IV bags. When the connectors and tubing are initially connected to such sources, they are generally empty (e.g., filled with air) and must be primed with fluid before they can be connected to a patient. During the priming procedure, fluid is allowed to flow from the upstream end of the tubing toward the male luer connector on the downstream end.

As the fluid flows through the tubing, the air in the tubing escapes through the male connector on the downstream end into the environment. Once the fluid itself reaches the male connector, it can also escape and spill out. Because male luer connectors do not usually close automatically after priming, the male luer often drips out a small amount of fluid as the male connector is rapidly moved into mating engagement with a female connector. For this reason, the male luer is generally held over a sink or trash can at the end of the priming procedure to contain the dripping fluid.

SUMMARY OF SOME EXEMPLIFYING EMBODIMENTS

Disclosed are various embodiments of medical connectors with closeable male luers. It is contemplated that one or more of the features of the various embodiments disclosed in FIGS. 1-11B and the associated written disclosure are combinable with one or more features of other embodiments disclosed in FIGS. 1-11B and the associated disclosure to form additional embodiments. Such combinations are within the scope of this disclosure. In some embodiments, closeable male luer connectors automatically open when engaged with a female connector and automatically close when disengaged from such connector or easily can be mechanically opened or closed to minimize or eliminate dripping during priming and other procedures and to improve the barrier of the fluid transfer system against bacteria and other debris. In some embodiments, a closable male luer can be mechanically opened by a user without disrupting the mechanical connection between connectors (e.g., such as by unscrewing connections between housings) so as to minimize or eliminate dripping during priming and other procedures and to improve the barrier of the fluid system against bacteria and other debris, as well as to allow the user to more carefully control the timing of the opening of the closable male luer.

In some embodiments, a male luer connector has a main housing with first and second ends. The first end of the housing can comprise a male luer and a shroud surrounding at least a portion of the male luer. The shroud can include screw threads disposed on an internal wall thereof. A tubular valve member with a fluid pathway can be disposed within the housing. The valve member can have a tip on its first end. In the region near the tip, one or more fluid holes can be positioned on the valve member so as to provide a fluid pathway there through. The tip can be configured to abut snugly against an internal wall of the male luer in a region at or near the first end of the male luer. In some embodiments, the valve member can also have one or more struts that can be directed towards the first end. The struts can extend axially through a portion of the housing, and the ends of the struts toward the first end can be positioned within a space between the male luer and the shroud on the first end of the housing. A length of medical tubing can be connected to the connector. An end of the tubing can be attached to the second end of the connector by adhesive, welding, threading, or some other means. A resilient member formed from either a metal or an elastomeric material can be positioned with at least a portion within the housing and can bias the valve member toward the closed position.

In the closed state or position, the tip of the valve member can be pressed into close contact with a portion of the internal wall on the first end of the male luer, and fluid flow from the medical tubing through the tubular valve member can be generally impeded. Fluid generally does not exit through the opening on the first end of the male luer because such opening can be blocked by the tip of the valve member.

When a force is applied to move or displace the valve member from the housing, the resilient member can be stressed against its bias and the tip of the valve member can be displaced toward the open position. This displacing force can be applied automatically through the action of connecting the male luer to a female end of another medical implement. As the advancing end of the female connector proceeds up the first end of the housing of the male luer connector, the female connector makes contact with and exerts a force directed towards the second end against the struts of the valve member or against another portion of the valve member, such as the luer tip. This force can move a portion of the valve member towards the second end against the biasing force that can be directed towards the first end exerted by a resilient member. In this opened state, fluid can be permitted to flow through the opposing holes, around the tip of the valve member, and out of the connector through the gap between the tip of the valve member and the internal wall on the first end of the male luer. In some embodiments, the valve member can be automatically advanced in the direction of the second end when the valve member contacts a fluid conduit (e.g., a conduit positioned within a female connector) as the male and female connectors are brought together.

In some embodiments, when the separating force is removed, for example, by releasing the manual grip on the housing and the tubing, or by detaching the female connector from the first end of the housing, the resilient member once again can urge the valve member to the closed position. This can cause the tip on the first end of the valve member to abut closely against a portion of the internal wall in a region near the first end of the male luer, and can impede fluid flow out of the valve.

Also disclosed herein are other features and configurations for the foregoing embodiment, as well as additional embodiments for other connectors with closeable male luers. Such embodiments generally include means for permitting or impeding fluid flow through a male luer on a connector, which can be automatically manipulated upon connection with a corresponding female connector. Such embodiments also include features and configurations that permit the female portion of the male luer connector to be coupled with a corresponding male luer portion of a male luer connector or other component such as a syringe.

Some embodiments disclosed herein relate to a first arrangement of a luer connector having a housing having a hollow bore, a first end, and a second end. A male luer tip can be supported by the housing, the male luer tip configured to rotate with respect to the housing. The male luer tip can have a first open end and a passageway through the male luer tip in fluid communication with the first open end. The luer connector can have a substantially rigid internal member extending into the passageway of the male luer tip toward the first open end of the male luer tip. In some embodiments, at least one of the male luer tip and the internal member can be axially moveable between a first position and a second position relative to the other of the male luer tip and the internal member. The male luer tip and the internal member can be configured to cooperate such that rotation of the male luer tip in a first direction relative to the housing increases an axial displacement between the first open end of the male luer tip and an end portion of the internal member.

In the first position, the end portion of the internal member can provide a substantially fluid-tight seal with respect to the first open end of the male luer tip so as to substantially prevent a flow of fluid through the male luer tip, and in the second position, the end portion of the internal member can be spaced apart from the first open end so that fluid is permitted to flow through the first open end of the male luer tip. In any of the previously described first arrangements, the male luer tip can be configured to rotate with respect to the housing as a female connector is threadedly connected to the luer connector.

In some embodiments, the male luer tip and the internal member can cooperate such that rotation of the male luer tip in a second direction relative to the housing decreases the axial displacement between the first open end of the male luer tip and the end portion of the internal member. In some embodiments, the internal member can be axially moveable relative to the male luer tip, and can have a solid cross-section along at least a substantial portion of the length thereof such that at least a substantial amount of fluid flowing through the luer connector is required to flow around an outside surface of the internal member. Some arrangements of the internal member can have an axial opening through at least a portion of the internal member, the axial opening being in fluid communication with the hollow bore of the housing and being configured to permit fluid to flow through the internal member.

Some embodiments of the luer connector disclosed herein can further have a chamber within the housing, the chamber being configured produce a change in volume as at least one of the male luer tip and the internal member axially moves between the first position and the second position relative to the other of the male luer tip and the internal member. The volume of the chamber can be larger when the male luer tip and the internal member are in the first position. Some arrangements of the internal member can have a helical or angled surface, the helical or angled surface configured to cooperate with the male luer tip and to cause the change in axial displacement between the male luer tip and the internal member as the male luer tip is rotated. The luer connector can have a resilient member configured to bias the male luer tip and the internal member toward the first position.

In some embodiments, an opening in the first open end of the male luer tip and the end portion of the internal member can have an ovular or other non-circular cross-sectional shape. The opening in the first open end of the male luer tip can have a tapered internal wall portion and the end portion of the internal member can have a tapered external wall portion that cooperates with the internal wall portion of the male luer tip. The male luer tip and the internal member can be configured such that relative rotation between the male luer tip and the internal member causes axial displacement between the male luer tip and the internal member.

Some embodiments disclosed herein relate to a luer connector having a housing having a hollow bore, a first end, and a second end, a male luer tip supported by the housing configured to axially move with respect to the housing, the male luer tip having a first open end and a passageway through the male luer tip in fluid communication with the first open end, and a substantially rigid internal member extending into the passageway of the male luer tip toward the first open end of the male luer tip. In some embodiments, the male luer tip can be axially moveable between a first position and a second position relative to the internal member. In the first position, an end portion of the internal member can provide a substantially fluid-tight seal with respect to the first open end of the male luer tip so as to substantially prevent a flow of fluid through the male luer tip, and in the second position, the end portion of the internal member can be spaced apart from the first open end so that fluid is permitted to flow through the first open end of the male luer tip.

In some embodiments of the luer connector, the male luer tip can be configured to axially move from the first position to the second position as a female connector is threadedly connected to the luer connector. Some embodiments of the internal member can have a solid cross-section along at least a substantial portion of the length thereof such that at least a substantial amount of fluid flowing through the luer connector is required to flow around an outside surface of the internal member. In some embodiments, the internal member can have an axial opening through at least a portion of the internal member, the axial opening being in fluid communication with the hollow bore of the housing and being configured to permit fluid to flow through the internal member. The luer connector can further have a resilient member configured to bias the male luer tip toward the first position.

Some embodiments disclosed herein relate to a luer connector having a housing having a hollow bore, a first end, and a second end, a male luer tip supported by the housing configured to rotate with respect to the housing, the male luer tip having an opening in a first end thereof and a passageway through the male luer tip in fluid communication with the opening in the first end thereof. The luer connector can have an internal member extending into the passageway of the male luer tip toward the opening in the first end thereof, the internal member having an opening in a first end thereof and a passageway through the internal member in fluid communication with the opening in the first end thereof. The male luer tip can be configured to be rotatable between a first position and a second position relative to the internal member. In the first position, the opening in the first end of the male luer tip can be substantially offset with respect to the opening in the first end of the internal member so as to substantially prevent a flow of fluid through the male luer tip, and, in the second position, the opening in the first end of the male luer tip can be substantially aligned with respect to the opening in the first end of the internal member so that fluid is permitted to flow through the male luer tip.

In some embodiments, the male luer tip can be configured to rotate in a first direction with respect to the housing from the first position to the second position as a female connector is threadedly connected to the luer connector, and/or to rotate in a second direction with respect to the housing from the second position to the first position as a female connector is threadedly disconnected from the luer connector. In some embodiments, the internal member can be rotationally fixed relative to the housing in some embodiments. The luer tip can be biased toward the first position. The luer connector can be configured such that the male luer tip is prevented from rotating beyond the first or the second position.

Disclosed in the rest of the Summary section below are various embodiments of medical connectors with closeable male luers that are disclosed in FIGS. 12A-19D and the associated written description. It is contemplated that the features of the various embodiments disclosed in FIGS. 12A-19D and the associated written description are combinable to form additional embodiments. Such combinations are within the scope of this disclosure.

In some exemplifying embodiments, a male luer connector can have a main housing with first and second ends. The first end of the housing can comprise a male luer and a shroud surrounding at least a portion of the male luer. The shroud can have screw threads disposed on an internal wall thereof. A tubular valve member with a fluid pathway can be disposed within the housing. The valve member can have a tip on its first end. In the region near the tip, one or more fluid holes can be positioned on the valve member so as to provide a fluid pathway therethrough. The tip can be configured to abut snugly against an internal wall of the male luer in a region at or near the first end of the male luer. The valve member can also have one or more struts that can be directed towards the first end. The struts can extend axially through a portion of the housing, and the ends of the struts toward the first end can be positioned within a space between the male luer and the shroud on the first end of the housing. A length of medical tubing can be connected to the connector. An end of the tubing can be attached to the second end of the valve member by adhesive, friction fit, welding, or some other means. A resilient member formed, for example, from either a metal and/or an elastomeric material can be positioned within the housing and can bias the valve member toward the closed position.

In the closed state or position, the tip of the valve member can be pressed into close contact with a portion of the internal wall on the first end of the male luer, and fluid flow from the medical tubing through the tubular valve member can be generally impeded. Fluid generally cannot escape through the opening on the first end of the male luer because such opening can be blocked by the tip of the valve member.

When a force is applied to move or displace the valve member from the housing, the resilient member can be compressed and the tip of the valve member can be displaced toward the open position. This displacing force can be applied automatically through the action of connecting the male luer to a female end of another medical implement. As the advancing end of the female connector proceeds up the screw threads on the first end of the housing of the male luer connector, the female connector makes contact with and exerts a force directed towards the second end against the struts of the valve member. This force moves the valve member towards the second end against the biasing force directed towards the first end exerted by the resilient member. In this opened state, fluid can be permitted to flow through the opposing holes, around the tip of the valve member, and out of the connector through the gap between the tip of the valve member and the internal wall on the first end of the male luer. In some embodiments, the valve member can be automatically advanced in the direction of the second end when the valve member contacts a fluid conduit (e.g., an internal conduit positioned within a female connector) as the male and female connectors are brought together.

When the separating force is removed, for example, by detaching the female connector from the first end of the housing, the resilient member once again can draw the housing and the valve member together. This causes the tip on the first end of the valve member to abut closely against a portion of the internal wall in a region near the first end of the male luer, and impedes fluid flow out of the valve.

Some embodiments provide a medical connector including a substantially rigid housing having a first end and a second end wherein the first and second ends are connected by a selectively closable fluid passageway. The first end can include a hollow male luer with an inner surface, a first open end, and a second base end. The connector can further include a first valve member supported substantially within the housing, the first valve member being configured to selectively seal an opening adjacent to the first end of the housing at the tip of the male luer when the connector is in a closed position and an internal bladder member positioned within the housing and outside the male luer, the bladder member defining an inner cavity and being fluidly coupled to the first valve member, the inner cavity of the bladder member having a first volume in the connector closed position and a second volume smaller than the first volume when the connector is in an open position.

In some embodiments, the rigid housing may extend laterally from the base of the male luer and an activation arm may extend through the housing adjacent the base of the male luer, a first end of the activation arm configured to engage a corresponding female end of a medical implement and a second end of the activation arm configured to engage at least a portion of the bladder member. In some embodiments there is a plurality of activation arms wherein the plurality of activation arms can be connected by a ring. In some embodiments, the bladder member of the connector can include a wall portion being concave toward a longitudinal axis of the connector so as to form a substantially ovular inner cavity. In some embodiments, the bladder member includes a corrugated wall portion. In some embodiments, at least a portion of the bladder member and at least a portion of the valve member are integrally formed.

In some embodiments, the connector includes an annular ring between the valve member and the inner surface of the male luer. The annular ring can be integrally formed with the valve member and can remain in sliding engagement with the inner surface of the male luer between both the closed and open positions of the connector. Alternatively, the inner surface of the male luer can include an annular channel and the annular ring can be recessed into said annular channel and can be in sliding engagement with the outer surface of the valve member.

In some embodiments, the second end can have a female connector portion having an opening axially therethrough. An internal bladder member can be positioned within the housing so that it is outside of the female connector portion so as to be between an end wall of the housing adjacent to the female connector portion and between a valve member positioned within a male luer connector portion of the medical connector. The bladder member can define an inner cavity and can be fluidly coupled to the valve member and the female connector portion. The inner cavity of the bladder member can have a first volume in the connector closed position and a second volume smaller than the first volume when the connector is in an open position.

A protrusion can project from the female portion (e.g., the end wall of the housing) and can be configured to extend into an opening formed in the bladder member. The protrusion can have an annular recess thereon configured to receive the annular wall forming the perimeter of the opening of the bladder member. The opening in the bladder member and the protrusion can be configured to form a generally liquid or gas tight seal between the protrusion and the bladder member so that the bladder member can be sealably supported by the protrusion and, hence, the end wall of the housing.

Similarly, a protrusion can project from the valve base and can be configured to extend into a second opening formed in the bladder member. The protrusion can have an annular recess thereon configured to receive the annular wall forming the perimeter of the second opening of the bladder member. The second opening in the bladder member and the protrusion can be configured to form a generally liquid or gas tight seal between the protrusion and the bladder member so that the bladder member can be sealably supported by the protrusion and, hence, the valve base. In some embodiments, one or more activation arms can be supported by the valve base. The activation arms can be integrally formed with the valve base or otherwise attached to or supported by the valve base.

Some embodiments provide a closeable male luer having a rigid housing, a valve member supported within the housing, and a first end portion. The first end portion can be, inter alia, a male luer tip. The valve member can extend into an opening formed in the first end portion and move between a first or closed position (wherein liquid is substantially prevented from flowing through the valve member and tip) and a second or open position (wherein liquid is permitted to flow through the valve member and tip). The valve member can be configured to be moveable between a first and a second position by imparting a force directly on a portion of the valve member, such as without limitation, a tube member projection from a valve base.

In some embodiments, the closeable male luer can further comprise, without limitation, struts or activation arms projecting from a valve base of the valve member toward a first end of the medical connector. The struts can be configured such that an axial force imparted on the valve struts can be transferred to the valve base so as to displace the valve member. The struts can be configured to engage a proximal end of a female connector engaged with the closeable male luer as the female connector threadably or otherwise advances into engagement with the closeable male luer. A valve tube can be supported by or attached to the valve base, and can project from the valve base such that, in the assembled configuration, the valve tube extends into an opening formed in the male luer tip.

In some embodiments, a diaphragm member formed from a generally liquid impermeable resilient material can be supported within the housing. The diaphragm member can have a generally planar shape or a pair of generally parallel, planar surfaces. The diaphragm member can also have, but is not required to have, a generally annular, disc-like shape. The diaphragm member can be positioned such that an outer periphery of the diaphragm member is sealably supported by the housing. An annular recess can be formed in the housing to support the outer periphery of the diaphragm member. Alternatively, the outer periphery of the diaphragm member can be positioned between a portion of each of two housing portions. An opening can be formed in the diaphragm member, the opening configured to receive an aft portion of the valve base so that the diaphragm member can be sealably secured to the valve member. In some embodiments, a projection extending from the valve base can be received within the opening in the diaphragm member. The projection can define a recess configured to receive and support the opening formed in the diaphragm member.

The diaphragm member can be positioned so as to exert a force on the valve member that biases the valve member toward the closed position. For example, without limitation, the diaphragm member can bias the tube member projecting from the valve base to sealably close against the inside surface of the luer tip. In some embodiments, the diaphragm member can be positioned within the luer connector so that, when the valve member is in the closed position, the diaphragm is partially deflected from its relaxed state so as to increase the bias force that the diaphragm exerts on the valve member.

The diaphragm member can form a partition within the housing so as to create a substantially fluid sealed cavity or chamber within the housing. The diaphragm member can be configured so that the volume within the cavity when the valve member is in the closed position is greater than volume within the cavity when the valve member is in the open position. In this configuration, the volume of space within the cavity can increase when the valve member moves from the open position to the closed position, thereby creating a force of suction that can reduce the amount of fluid or medicament that can flow through or drip out of an opening in the male luer tip as the valve member closes, by drawing such fluid back toward the cavity.

In some embodiments, the valve member can be configured such that the valve struts are directly attached to either the tube or the valve base so that an axial force imparted on the valve struts that causes the valve struts to displace also causes at least a portion of the diaphragm member to displace in addition to causing the tube and/or the valve base to displace. In some embodiments, the valve struts can be separate from the valve base or the tube so as to move independently compared to the valve base or the tube. In this configuration, the struts can each can exert an axial force on at least a portion of the diaphragm when the struts are displaced due to the engagement of a female connector with the first end portion of the housing, thereby deflecting the diaphragm. As the diaphragm is deflected, the valve member can be moved toward the open position because the diaphragm can be secured to the valve base.

In some embodiments, the bladder member can have a generally cylindrical or tubular shape, and can be positioned within the housing so that the opening axially through the bladder member is generally coaxially aligned with an opening formed in a female connector portion of the housing and an opening formed in the male luer tip. The bladder member can have one end surface that can be sealably supported by or positioned against an end wall surface adjacent to the female connector portion of the housing. Similarly, a second end surface of the bladder member can be sealably supported by or positioned against a valve base of the valve member so as to define a chamber or cavity bounded generally by the tubular wall of the bladder member, the end wall of the housing, and the valve member. An opening formed through the end wall of the housing and an opening formed in the valve member can be in communication with the chamber. The volume within the chamber when the luer connector is in the closed position can be larger than the volume within the chamber when the luer connector is in the open position. The increase in the volume of the chamber as the valve member moves from the open to the closed position can create a reduced pressure that draws the fluid from the luer tip or tube back into or toward the chamber.

Some embodiments provide a method for selectively closing a medical connector, the method comprising supporting a resilient bladder member within a housing, moving a valve member at least partially supported within the housing between a connector open position and a connector closed position such that, in the closed position, the valve member substantially prevents liquid from flowing through the fluid passageway and, in the open position, the valve member permits liquid to pass through the fluid passageway, and moving the bladder member between a first configuration having a first volume in the connector closed position and a second configuration having a second volume in the connector open position. The second volume can be, but is not required to be, smaller than the first volume.

The housing can have a first end and a second end, said first and second ends being connected by a selectively closable fluid passageway and said first end having a hollow male luer with an inner surface. In some embodiments, the bladder member can have a corrugated wall portion. In some embodiments, the bladder member can have an opening therethrough and an internal chamber in communication with the fluid passageway. Further, the bladder member can be, but is not required to be, supported within the housing so as to be outside the male luer.

Some embodiments provide the method described above, wherein moving the valve member between the connector open position and the connector closed position and moving the bladder member between the first configuration and the second configuration can comprise engaging or disengaging the medical connector with or from a corresponding female end of a medical implement. In some embodiments, moving the bladder member between the first configuration and the second configuration can comprise moving at least one activation arm between a first and a second position, the at least one activation arm being configured to engage a corresponding female end of a medical implement and having a second end thereof configured to engage at least a portion of the bladder member. Moving the at least one activation arm between the first and the second position can comprise engaging or disengaging the medical connector with or from a corresponding female end of a medical implement.

Also disclosed herein are other features and configurations for the foregoing embodiment, as well as additional embodiments for other connectors with closeable male luers. Such embodiments generally include means for permitting or impeding fluid flow through a male luer on a connector, which can be automatically opened upon connection with a corresponding female connector. Such embodiments also include features and configurations that permit the female portion of the male luer connector to be coupled with a corresponding male luer portion of a male luer connector or other component such as a syringe.

BRIEF DESCRIPTION OF THE DRAWINGS

Certain embodiments of this disclosure will now be discussed in detail with reference to the following figures. These figures are provided for illustrative purposes only, and the embodiments are not limited to the subject matter illustrated in the figures.

FIG. 4C is a perspective view of an embodiment of a luer tip of the embodiment of the luer connector shown in FIG. 4A.

FIG. 4D is a side view of the embodiment of the luer tip shown in FIG. 4C.

FIG. 4E is a perspective view of an embodiment of a valve tube of the embodiment of the luer connector shown in FIG. 4A.

FIG. 4F is a side view of the embodiment the valve tube shown in FIG. 4E.

FIG. 5A is a cross-sectional view of another embodiment of a luer connector in a closed position.

FIG. 5B is an end view of the embodiment of the luer connector shown in FIG. 5A in a closed position.

FIG. 5C is an end view of the embodiment of the luer connector shown in FIG. 5A, showing the embodiment of the luer connector in an open position.

FIG. 5D is a cross-sectional view of the embodiment of the luer connector shown in FIG. 5A taken through line 5D-5D in FIG. 5C.

FIG. 5E is a cross-sectional view of the embodiment of the luer connector shown in FIG. 5A taken through line 5E-5E in FIG. 5C.

FIG. 5F is a perspective view of a portion of an embodiment of a valve tube of the embodiment of the luer connector shown in FIG. 5A.

FIG. 6A is a cross-sectional view of another embodiment of a luer connector in a closed position.

FIG. 6B is a cross-sectional view of the embodiment of the luer connector shown in FIG. 6A in an open position.

FIG. 6C is an end view of the embodiment of the luer connector shown in FIG. 6A in a closed position.

FIG. 6D is an end view of the embodiment of the luer connector shown in FIG. 6B in an open position.

FIG. 11A is a cross-sectional view of another embodiment of a luer connector in a closed position.

FIG. 11B is a cross-sectional view of the embodiment of the luer connector shown in FIG. 11A in an open position.

DETAILED DESCRIPTION OF SOME EXEMPLIFYING EMBODIMENTS

In some embodiments of those disclosed in FIGS. 1-11B and the associated written disclosure, closing mechanisms function to substantially prevent and/or impede fluid from escaping from or entering into the male luer end of a connector, while allowing fluid flow when the male luer is manually opened or engaged with a corresponding female luer. As used in the description associated with FIGS. 1-11B, terms such as "closed," "sealed," "prevent," or "impede" should be understood as obstructions or barriers to fluid flow. These terms should not be understood to require that a particular structure or configuration achieves a complete fluid closure in all circumstances.

Some medications, including those used during chemotherapy, can be harmful to a patient in certain applications. For example, exposure to the skin can sometimes result in a chemical burn. Inhalation of aerosolized forms of some medications also can be harmful. Thus, control over the containment of the medication is highly desirable.

Figure 1A:
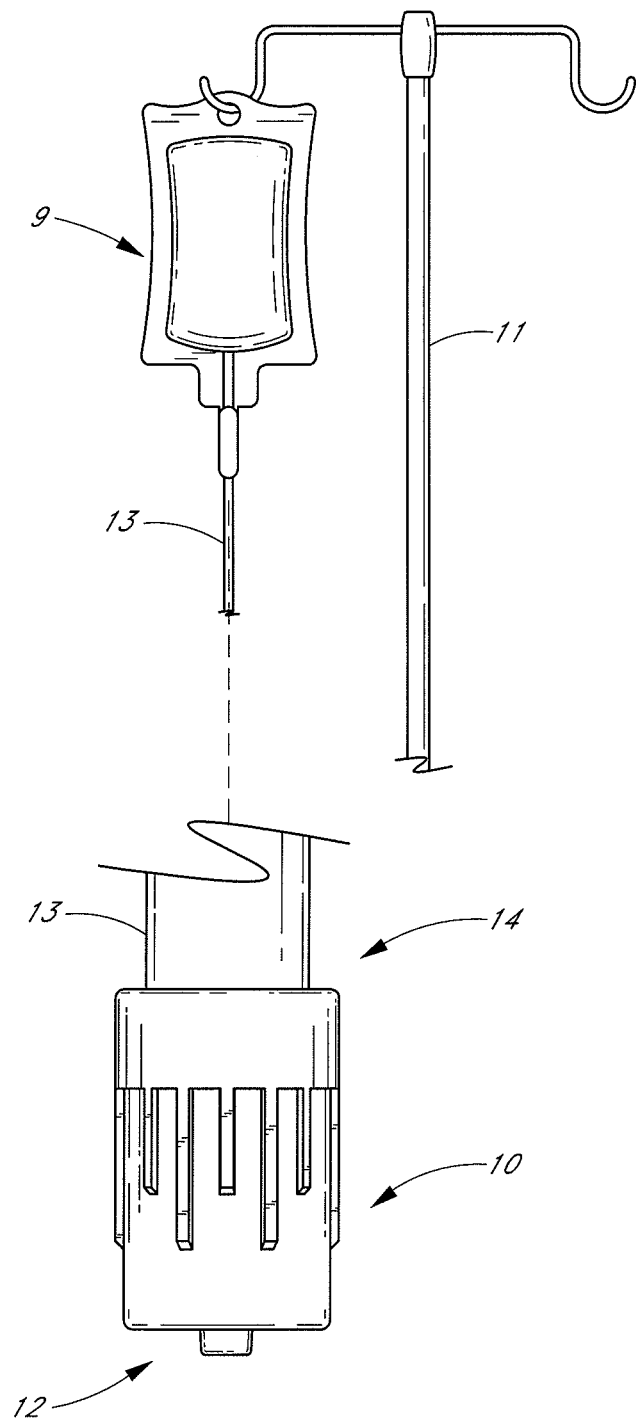
FIG. 1A is a perspective view of an embodiment of a male luer connector attached to tubing configured to receive fluid from a hanging gravity-fed IV bag. In this and other figures, the relative size of the connector and attached tubing is increased in comparison to other objects to facilitate viewing certain details.

FIG. 1A is a perspective view of an embodiment of a male luer connector attached to tubing configured to receive fluid from a hanging gravity-fed IV bag. In some embodiments, the female end of the connector can alternatively be configured to engage a standard male luer end. In FIG. 1A, some embodiments of a closeable male luer connector 10 is shown in a closed position. The luer connector 10 can be attached to a gravity-fed IV bag 9 filled with fluid hanging from a pole stand 11. At the bottom of the bag 9, a section of tubing 13 can be attached. The opposite end of the tubing 13 can be connected to the second end 14 of the luer connector 10. A closing mechanism on the interior of the first end 12 of the luer connector 10 can prevent the fluid contained within the bag 9 from flowing through the tubing 13 and leaking out of the luer connector 10, as long as the luer connector 10 remains in a closed configuration.

The IV delivery system illustrated in FIG. 1A can be easily readied for fluid communication with a patient. In most circumstances, the tubing 13 can be filled with air when it is initially connected to the IV bag 9. If the other end of the tubing 13 can be connected to a closed connector, as illustrated in FIG. 1A, the air cannot escape and fluid cannot enter the tubing 13 from the IV bag 9. In some embodiments, the luer connector 10 can be changed so as to be in the open position until all of the air has been purged through the luer 10 and the fluid in the IV bag 9 fills the tubing 13 and connector 10. This procedure is known as "priming." As soon as the fluid line and connector are properly primed, the health care provider can then change the luer connector 10 to the closed position to stop the flow of fluid through the luer connector 10.

Figure 1B:
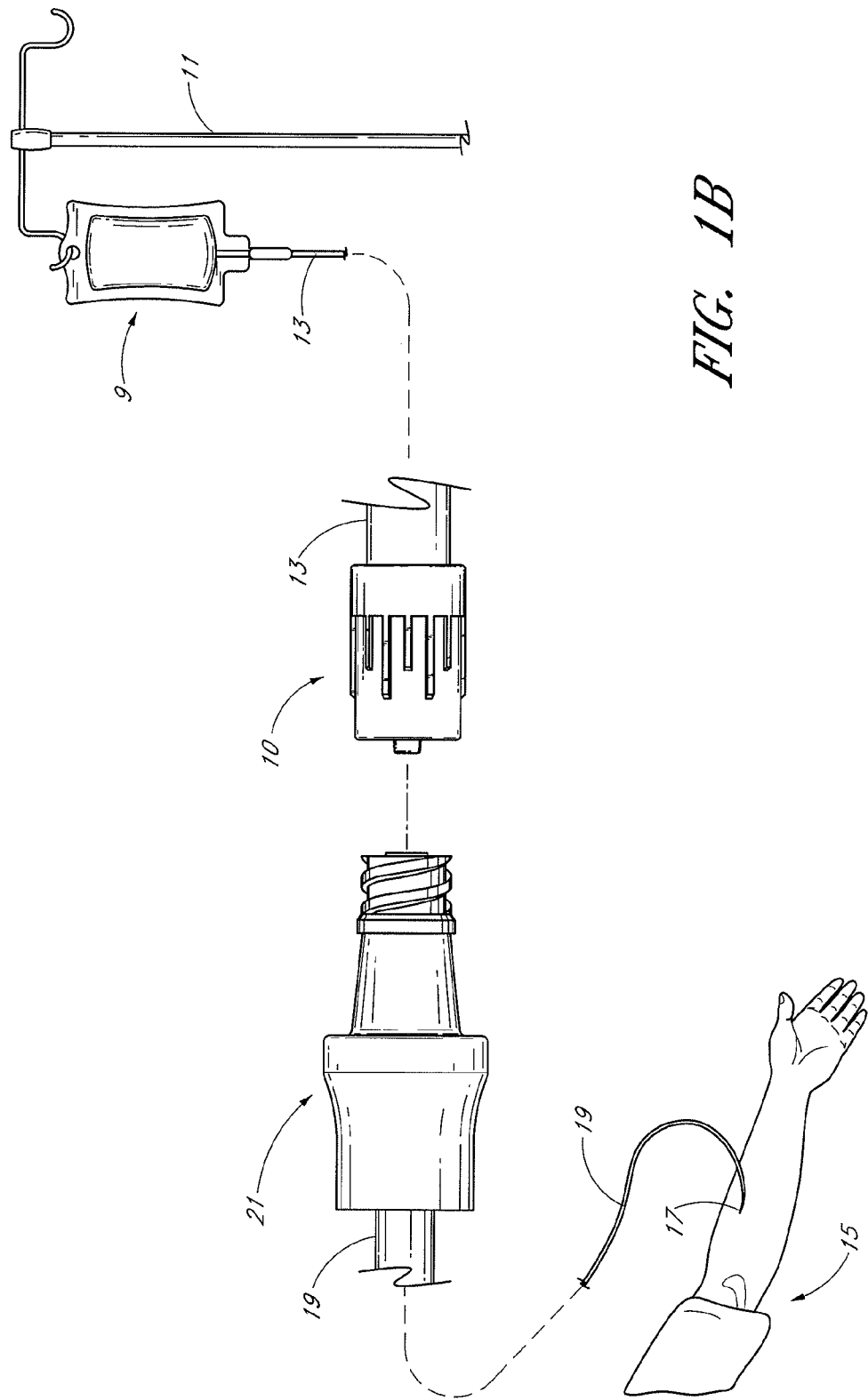
FIG. 1B shows a perspective view of an embodiment of the male luer connector of FIG. 1A being connected to a female connector attached to tubing inserted into a patient.

FIG. 1B shows a perspective view of an embodiment of the male luer connector of FIG. 1A being connected to an exemplifying female connector attached to tubing inserted into a patient. Referring now to FIG. 1B, a catheter 17 has been inserted into a patient's arm 15. The catheter 17 penetrates the skin of the arm 15 and can be fluidly connected with the patient's bloodstream. The catheter 17 can also be connected to a length of medical tubing 19 attached to a female medical connector 21. The example of a female medical connector 21 illustrated in FIG. 1B is a version of the Clave® connector manufactured by ICU Medical, Inc., San Clemente, Calif. Various embodiments of a connector of this type are illustrated and described in U.S. Pat. No. 5,685,866, which is incorporated herein by reference in its entirety. It is contemplated that many of the male luer embodiments disclosed in FIGS. 1-11B and the associated written disclosure can be used with other types of female connectors. The tubing 19, catheter 17, and female connector 21 were previously primed with fluid using standard procedures. The luer connector 10 can be primed as described previously and brought into engagement with the female connector 21. As described in further detail below, when the male connector 10 and female connector 21 are engaged, fluid can be permitted to flow from the IV bag 9 into the patient. When the male connector 10 and female connector 21 are disengaged, fluid can be once again prevented from flowing out of the first end 12 of the male connector 10. In general, fluid can also be prevented from flowing out of the opening in the female connector 21.

The embodiment illustrated in FIGS. 1A-1B is described in further detail below. Each of the other embodiments disclosed in FIGS. 1-11B and the associated written disclosure can be used in the illustrated fluid system, and in various modifications and alternatives thereof. Further, it is contemplated that the various embodiments of connectors disclosed in FIGS. 1-11B and the associated written disclosure can be used in a wide variety of additional medical fluid systems. For example, the disclosed connectors can also be used to transfer bodily fluids such as blood, urine, or insulin, nourishing fluids, and/or therapeutic fluids such as fluids used in chemotherapy treatments. The disclosed connectors can also be used to interconnect various other components of fluid transfer systems.

Figure 2A:
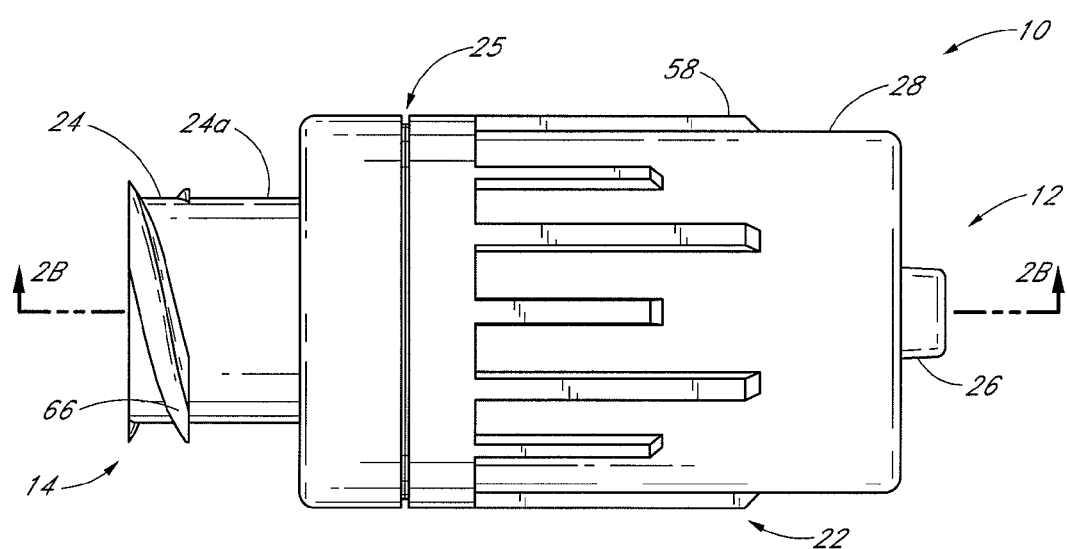
FIG. 2A is a side view of the outside of the embodiment of the luer connector shown in FIG. 1A.
Figure 2B:
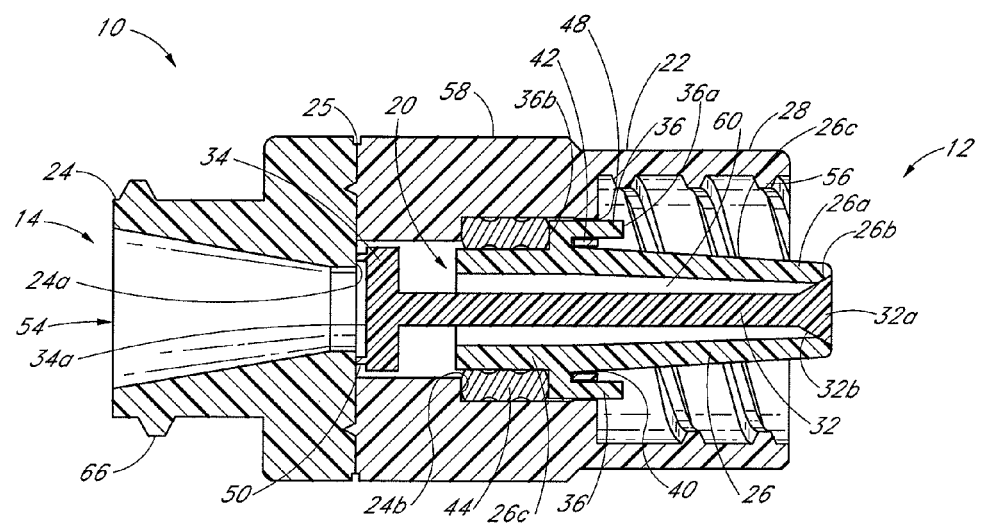
FIG. 2B is a cross-sectional view of the connector taken along the line 2B-2B in FIG. 2A in a closed position.
Figure 2C:
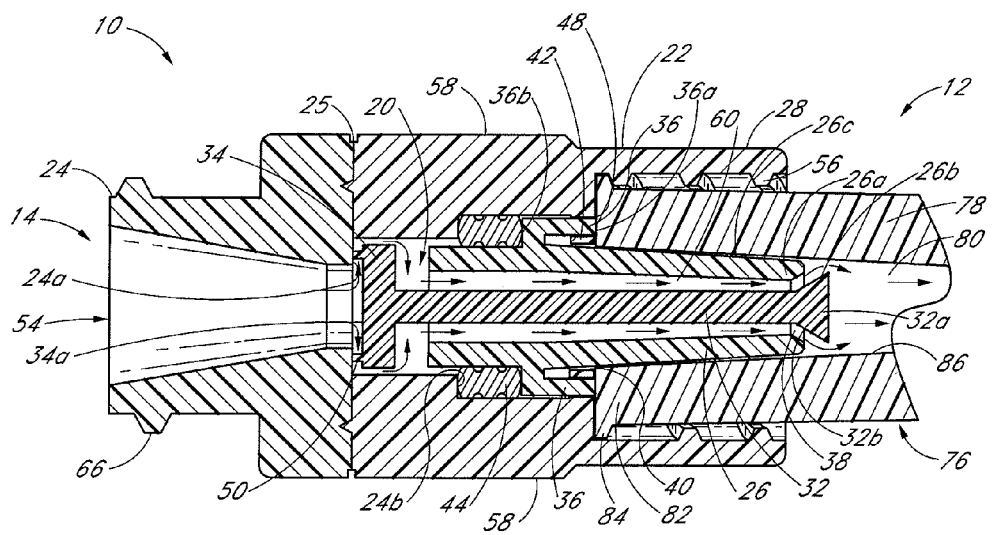
FIG. 2C is a cross-sectional view the connector taken along the line 2B-2B in FIG. 2A in an open position.

Referring now to FIGS. 2A-2C, the embodiment of the closeable male luer 10 of FIGS. 1A-1B is illustrated in greater detail. FIG. 2A is a side view of the outside of the embodiment of the luer connector 10. FIGS. 2B and 2C are cross-sectional views of the luer connector 10 in a closed (or first) position and an open (or second) position, respectively. When the luer connector 10 is in the closed position, fluid can be significantly prevented by the valve member 20 from flowing through the luer connector 10. In the open position, the valve member 20 can be moved to the open position so as to not significantly impede the flow of fluid through the luer connector 10.

As illustrated in FIG. 2A, some embodiments of the assembled luer connector 10 can comprise a housing 22, a port member 24 positioned near the second end 14 of the luer connector 10, a male luer or luer tip 26 positioned near the first end 12 of the luer connector 10, a shroud 28 surrounding at least a portion of the luer tip 26, and the valve member 20 mentioned above supported by the housing 22. The housing 22 can define a part line 25, where the two or more separately formed portions of the housing can be joined. With reference to illustrated embodiment, the port member 24 can be joined with the housing 22 at the part line 25 using ultrasonic welding, epoxy, or other adhesive, interference fits, mechanical connections, unitary constructions, and/or any other suitable coupling method or methods.

In some embodiments, the port member 24 and the housing 22 can be integrally formed, which may require the valve member 20 and the housing 22 to be configured differently to accommodate assembly of these and other components. For example, in some embodiments, where the port member 24 and housing 22 are integrally formed, the luer tip 26, valve tube 32, and sealing member 44 can be assembled within the housing 22 through the shroud 28 at the first end 12 of the luer connector. A retaining member (not illustrated) that can be configured to retain the luer tip 26 and sealing member 44 in the desired position within the housing 22 can be assembled with the housing 22 after the other components have been assembled in the housing 22. In some embodiments, the retaining member (not illustrated) can be a planar disk having openings formed therein and configured to allow the luer tip 26 and struts 36 to translate axially relative to the retaining member. The retaining member could be joined with the housing 22 using ultrasonic welding, epoxy, or other adhesive, interference fits, mechanical connections, and/or any other suitable coupling method or methods.

Additionally, the valve base 34 can be configured so that it is held in a fixed axial position adjacent to the port member 24 after the valve base 34 has been inserted into the housing 22. In some embodiments, the valve base 34 can be configured so as to form an interference fit with the port member 24 when assembled therewith. In some embodiments, the valve base 34 can be attached to the port member 24 using ultrasonic welds, adhesive, mechanical connections such as tabs, channels, or protrusions, and/or by any other suitable coupling method or methods. Axial openings (not illustrated) can be formed in the valve base 34 or any similar components disclosed in FIGS. 1-11B and the associated written disclosure to allow fluid or medicament to flow therethrough. Thus, in some embodiments, the valve base 34 can be formed to abut flat against one more of the inside surfaces of the port member 24. Alternatively, in some embodiments, the valve base 34 and valve tube 32 can be integrally formed with the port member 24, with the end portion 32a of the valve tube 32 being configured to be attached to the valve tube 32 after the luer tip 26 has been assembled.

Additionally, in the illustrated embodiment, the housing 22 can be configured so that the luer tip 26 projects through an opening 40 formed in an internal wall 42 formed within the housing 22. As will be described in greater detail below, the luer connector 10 can be configured so that the luer tip 22 translates axially relative to the opening 40 formed in the internal wall 42.

In the illustrated embodiment, the valve member 20 can comprise a tube 32 projecting from a valve base 34 toward the first end 12 of the connector 10, and a pair of valve arms or struts 36 also preferably projecting from and supported by the second region 26c of the male luer 26. In the illustrated embodiment, in an assembled configuration, the valve struts 36 can be positioned so as to be adjacent to the tip 26 along the sides of the tip 26. When the luer connector 10 is in the closed position, a portion of the inner surface of the distal portion 32a of the valve tube 32 can be sealingly closed against the inner surface of a portion of the distal portion 26a of the luer tip 26 such that fluid is generally prevented from flowing through the opening 38 formed in the distal end 26a of the luer tip 26.

The following are some sample cross-sectional diameters of the opening 38 preferably formed in the distal end portion 26a of the luer tip 26, or of any opening in any luer tip disclosed in FIGS. 1-11B and the associated written disclosure: approximately 2 mm or less and approximately 0.5 mm to approximately 2.0 mm. Other diameters, either inside or outside the listed ranges can also be used. In some embodiments, the opening 38 can be any desired or otherwise suitable geometry. Regardless of the geometry of the opening 38, the distal portion 32a of the valve tube 32 can be sized appropriately to occupy the space in the opening 38 so that, when the luer connector 10 is in a closed position, a generally fluid tight seal is provided.

In the illustrated embodiment, the luer connector 10 can be configured so that the tube 32 is supported in an axially fixed position relative to the housing 22. In particular, in some embodiments, the aft portion 34a of the valve base 34 can be supported indirectly or directly by the inside surface 24a of the port member 24. In the illustrated embodiment, one or more substantially rigid tabs 50 can be formed so as to project from the aft portion 34a of the valve base 34. The tabs 50 can be configured to abut against the inside surface 24a of the port member 24. The valve base 34 and the tabs 50 are preferably configured to allow fluid or medicament to flow freely around the valve base 34. Further, as mentioned above, the luer tip 26 can be slidably supported so as to translate axially relative to the valve tube 32.

The valve struts 36 that can be supported in a cantilevered disposition by the second end region 26c of the male luer 26 can be configured so as to slide within the openings 48 formed through the internal wall 42 of the housing 22. The number of openings 48 through the internal wall 42 can be equal to the number of the valve struts 36 that are supported by the valve base 34.

An annular sealing member 44 can be positioned between the outside surface of the luer tip 26 and the inside surface of the housing 22 so as to generally prevent any fluid from flowing through either of the openings 40, 48. The sealing member 44 can be formed from a resilient material and configured to provide an axial biasing force on the luer tip 26 toward the first end 12 of the luer connector 10, so as to bias the luer connector 10 to the closed position.

With reference to FIGS. 2B and 2C, the luer connector 10 can be configured so that the sealing member 44 abuts against an aft surface 36b of the valve struts 36 at a first end of the sealing member 44 (e.g., at the end of the sealing member 44 that is closer to the first end 12 of the luer connector 10). Similarly, the luer connector 10 can be configured so that the sealing member 44 abuts against an inside surface 24b of the port member 24 at a second end of the sealing member 44 (e.g., the end of the sealing member 44 that is closer to the second end 14 of the luer connector 10).

In some embodiments, as in the embodiment illustrated in FIGS. 2B-2C, the valve tube 32 or any other valve tube or valve member described with reference to any other embodiments disclosed in FIGS. 1-11B and the associated written disclosure can be solid such that a substantial portion of the fluid flowing through the luer connector flows around the outside of the valve member. Moreover, any luer connector embodiment disclosed in FIGS. 1-11B and the associated written disclosure can be configured such that the valve tube is solid or such that the valve tube comprises an opening axially through at least a portion thereof.

In some embodiments, the valve 20, the valve base 34, the valve struts 36, and the protrusion 52 can be integrally formed. In some embodiments, any of the features of the valve member 20, including the valve tube 32, the valve base 34, the valve struts 36, and the protrusion 52, can be separately formed and adhered or otherwise joined together in subsequent manufacturing steps.

In some embodiments, the housing 22 can generally be a tube-like structure with a passageway 54 that can extend away from the second end 14 of the connector 10 through the axial center of the luer connector 10. As such, in some embodiments, when the luer connector 10 is in the open state or position, as illustrated in FIG. 2C, fluid can be permitted to flow from the second end 14 through the port member 24, around the valve base 34 and the tube 32, and out through the opening 38 in the luer tip 26 positioned at the first end 12 of the luer connector 10. With reference to FIGS. 2B and 2C, near the second end 14 of the luer connector 10, the port member 24 and the corresponding section of the fluid passageway 54 can be sized and configured so as to accommodate a section of standard diameter medical tubing inserted therein, or so as to be joinable with any standard or suitably sized medical connector or component, in particular medical implements corresponding to ISO and/or ANSI standards.

In some embodiments, the length of the housing 22 (or any housing disclosed in FIGS. 1-11B and the associated written disclosure) from the second end 14 to the distal end of the luer tip 26 can be approximately 0.75 inch. However, the size of the housing 22 is not so confined. In some embodiments, the length of the housing 22 (or any housing disclosed in FIGS. 1-11B and the associated written disclosure) from the second end 14 to the distal end of the luer tip 26 can be from approximately 0.5 inch to approximately 0.75 inch, or from approximately 0.75 inch to approximately 1.0 inch, or from approximately 1.0 inch to approximately 1.5 inches or more, or from or to any value within these ranges. Thus, the housing 22 can be, but is not necessarily, less than or equal to approximately 1.5 inches from the second end 14 to the distal end of the luer tip 26 so that the weight and bulk of the connector can be minimized. However, the housing 22 can have any length suited for a particular application.

The shroud 28 can have inner threads 56 on an interior wall to securely attach the connector 10 in a removable manner to another medical implement. In other embodiments, the shroud 28 can include other structures or materials for providing a releasable connection, including quick-release mechanisms and other means. As illustrated, the housing 22 and shroud 28 can define a plurality of protrusions 58 or other suitable features on an outer surface to assist the user in firmly grasping and twisting the shroud 28 and the housing 22 with the user's fingers so as to prevent the luer connector 10 from slipping within the user's grasp when the luer connector 10 is twisted. In other embodiments (not illustrated) the housing 22 or shroud 28 may alternatively or additionally define depressions that have upwardly tapering sidewalls that prevent the fingers from sliding off the connector 10, or any other features or materials that prevent the fingers from sliding relative to the connector 10. The protrusions 58 may extend around substantially the entire outer surface of the housing 22 or shroud 28 so that the user's fingers, when positioned on opposite sides of the connector 10, will likely encounter a depression, regardless of the orientation of the connector 10, during use.

With reference to FIGS. 2A-2C, the tip 26 can have a tapered external wall. The diameter of the luer tip 26 can become gradually smaller from the valve base 34 towards the distal end portion 26a of the tip 26. As described above, the tip 26 can define an opening 38 positioned at the distal end portion 26a of the luer tip 26. Near the base of the luer tip 26, which can be the internal wall 42, an interior space 60 (most clearly shown in FIG. 2B) can communicate with the fluid passageway 54 of the luer connector 10 and with the opening 38 so as to provide a fluid flow path through the entire luer connector 10. In some embodiments, the term fluid passageway is meant to refer to the entire fluid pathway through the luer connector. With regard to any of the luer connectors disclosed in FIGS. 1-11B and the associated written disclosure, the dimensions of the housing, shroud, luer tip, or port member (e.g., the male and female ends) or other interfaces can be made to comply with applicable standards and/or regulations, such as the ANSI standards and or ISO standards.

As most clearly illustrated in FIG. 2C, in some embodiments, the distal end portion 32a of the tube 32 can be configured so as to complement the size and shape of the distal end portion 26a of the luer tip 26 so as to define a sealable closing mechanism. In particular, in some embodiments, in the closed position, the inside surface 26b of the luer tip 26 can be positioned against the outside surface 32b of the valve tube 32 so as to provide a generally fluid-tight seal that prevents fluid or other medicament from pass through the opening 38 that can be formed in the distal end 26a of the luer tip 26. Thus, in this configuration, the closing mechanism can be adapted to close the fluid passage extending through the closeable male luer 10 from fluid communication with the external environment, preferably whenever the male luer 10 is not engaged with a female connector.

Thus, as the distal end portion 32a of the tube 32 abuts against the inside surface of the luer tip 26, closure can be formed at or near the first end 12 of the male luer 10. Further, the distal end portion 32a of the tube 32 can be made from, or covered by, a different material than is used to form the tube 32. For example, in some embodiments, the distal end portion 32a can be covered with a softer, more malleable or deformable material that may exhibit better sealing properties as compared to the material used to form the tube 32 so as to provide a better seal between the distal end portion 32a of the tube 32 and the luer tip 26.

Any of the luer connectors disclosed in FIGS. 1-11B and the associated written disclosure may be configured to comprise the features of any of the embodiments of the luer connector 10 described above. Further, in some embodiments, the valve member 20 can be constructed without a fluid path and function as a blocking plunger for fluid flowing around the valve member 20 rather than a means for conveying fluid between the first and second ends of the luer connector 10.

The housing 22 of the illustrated embodiment, or the housing of any embodiment disclosed in FIGS. 1-11B and the associated written disclosure, the port member 24, and any other components disclosed in FIGS. 1-11B and the associated written disclosure can be constructed from any of a number of different materials or combination of materials. In some embodiments, the housing 22 or any housing disclosed in FIGS. 1-11B and the associated written disclosure can be constructed from a relatively rigid material, such as polycarbonate or other polymeric material. The housing 22, port member 24, and/or the valve member of any embodiment disclosed in FIGS. 1-11B and the associated written disclosure, or any of the components of this or any other embodiment disclosed in FIGS. 1-11B and the associated written disclosure can also be constructed of a hydrophobic material, such as Bayer Makrolon, or any other suitable material.

The length of the valve member 20 can be shorter than the length of the housing 22, but the length of the valve member 20 is not so limited. Any of the valve assemblies disclosed in FIGS. 1-11B and the associated written disclosure, including but not limited to the valve member 20, can be manufactured through injection molding. Finally, although the valve member 20 of the illustrated embodiment is configured as shown in FIGS. 2B-2C, many other configurations are possible.

In some embodiments, as in the embodiments illustrated in FIGS. 2A-2C, one or more protrusions or raised tabs 66 (such as, but not limited to, threads) can be formed on an exterior surface 24a of the port member 24 to facilitate removably attaching a medical implement (not shown) with the second end 14 of the valve member 20. Accordingly, in some embodiments, the exterior surface 24a can be cylindrical except for the protrusions, raised tabs, or other features formed thereon. In some embodiments, the interior surface of the port member 24 can be conically shaped, such that the diameter of the interior surface can be greatest at the portion of the interior surface adjacent to the second end 14 of the luer connector 10. The internal taper of the interior surface can compliment and closely fit with the taper of a typical male luer. Such an internal taper can conform to ANSI and/or ISO standards and/or regulations, such as the standard for medical syringes.

Similarly, the outside surface 26c of the luer tip 26 can be straight or tapered so as to conform to ANSI and/or ISO standards and/or regulations, such as the standard for medical syringes. In some embodiments, the inside surface of the luer tip 26 and the outside surface of the tube 32 can either be straight or can also be tapered. Tapering the inside surface of the luer tip 26 and the outside surface of the tube 32 can help minimize the amount of fluid that flows into and is trapped in the interior space 60 between the tube 32 in the luer tip 26, since, as the tube 32 moves toward a closed position, the distance between the tapered inside surface of the luer tip 26 and the outside surface of the tube 32 would be reduced.

As shown in FIGS. 2A-2C, the closeable luer connector 10 can have a female mating end at the second end 14 of the luer connector 10 and a male luer mating end at the first end 12 of the luer connector 10. The closeable female connector 21 of FIG. 1B (referenced above), as well as other standard female connectors with similar external structure, can also have both female and male ends. In many embodiments, such female connectors can utilize seals or other fluid barriers to impede the flow of fluid on the female end but do not typically do so on the male end. In many of the embodiments of the closeable male luer connectors illustrated and disclosed in FIGS. 1-11B and the associated written disclosure there may be no seal or other fluid barrier shown on the female end. However, the female end of any of the closeable male luer connectors disclosed in FIGS. 1-11B and the associated written disclosure can be configured to include a closeable female end. For example, the structure for selective fluid-impedance with the female connector 21, or any of the other standard female connectors, could be included within the female end of any of the closeable male luer connectors disclosed in FIGS. 1-11B and the associated written disclosure to provide a connector that selectively seals or impedes fluid flow on both ends. In some embodiments of this type with closeable female and male ends, it can be advantageous for a resilient seal element to be positioned at or near the female opening, as shown in U.S. Pat. No. 5,685,866 entitled Medical Valve and Method of Use filed on Nov. 4, 1994 which disclosure is hereby incorporated by reference as if fully set forth herein. By positioning the seal element in this manner, it is possible to cleanse the female opening prior to use with antiseptic with a wiping motion to avoid a harmful accumulation of debris, bacteria, antiseptic, or other unwanted substances on the seal element and/or in the region between the seal element and the housing of the connector adjacent to the seal element.

With reference again to FIGS. 2B and 2C, the sealing member 44 will now be described in greater detail. In some embodiments, the sealing member 44 can define a generally cylindrical cross-section, as illustrated in FIGS. 2B and 2C. In some embodiments, the sealing member 44 can define a generally circular cross-section. In some embodiments, the sealing member can be substantially cylindrical and can have a bore extending axially through the center thereof. In some embodiments, the sealing member can further comprise a pair of generally rectangular protrusions extending from the sidewalls of the cylindrical portion at diametrically opposed positions. In other embodiments, the protrusions can have different shapes and/or positions, and can assist with positioning and/or aligning the sealing member in the desired position. In some embodiments, the sealing member 44 can also have a generally smaller-diameter middle portion surrounded by two rings at either end with larger diameters. The sealing member can be constructed from a number of different materials. In some embodiments, the sealing member can be made from a silicon-based deformable material. Silicon-based deformable materials are among those that can form fluid-tight closures with plastics and other rigid polymeric materials.

As mentioned, FIG. 2C is a cross-sectional view of the luer connector 10 in an open position, so that fluid can be generally permitted to flow through the luer connector 10. The flow of fluid or medicament through the luer connector 10 is represented by arrows in FIG. 2C. With reference to FIG. 2C, the housing 22, the valve member 20, and the sealing member 44 are in an assembled configuration. As illustrated, the valve member 20 has preferably been moved to the open position by the insertion of the female connector 76. Thus, FIG. 2C illustrates a cross-section and embodiment of the luer connector 10 wherein the valve member 20 has preferably been caused to be opened by the insertion of an exemplifying female connector 76.

With reference to the embodiment illustrated in FIG. 2C, the structure of an exemplifying female connector 76 will now be discussed in further detail. The female connector 76 can comprise an elongate body 78 having a fluid passageway 80 therethrough, and the female connector 76 can have a tip 82 near its proximal end. In some embodiments, the tip 82 of the female connector 76 can have a radially extending surface 84 disposed on its external surface. The female connector 76 can have a fluid conduit (not shown) within the female connector 76. The fluid conduit is not included or required in all female connectors compatible with the connectors 10 disclosed in FIGS. 1-11B and the associated written disclosure. Along a proximal inner surface 86 of the female connector 76, the fluid passageway 80 can be tapered such that the diameter of the fluid passageway 80 decreases in the distal direction.

As shown in FIG. 2B and discussed above, the struts 36 of the valve member 20 can extend through openings 48 in the internal wall 42 of the housing 22 such that, in the closed position, the ends of the struts 36 extend past the internal wall 42 toward the first end 12 of the connector 10. The struts 36 can be configured to engage the proximal end 84 of the female connector 76 as the female connector 76 advances into engagement with the closeable male luer 10. To engage the male luer 10 and female connector 76, as is shown in FIG. 2C, the radially extending surface or surfaces 84 of the female connector 76 can be threaded into the inner threads 56 of the male luer 10. As shown in FIG. 2C, the two luers 10, 76 can be threadedly engaged with one another until the taper of the inner surface 86 of the female luer connector 76 lies adjacent the correspondingly tapered external surface 26c of the tip 26.

As the male luer connector 10 and female connector 76 move towards each other into threaded engagement, the proximal end 84 of the tip of the female connector 76 can contact the struts 36 of the valve member 20. As the male luer connector 10 and female connector 76 move further into threaded engagement, the struts 36, and thereby the luer tip 26, can be moved toward the second end 14 of the male connector 10 by the female connector 76. Thus, as the male luer connector 10 and female connector 76 move further into threaded engagement, the distal end portion 26a of the luer tip 26 can move away from the interior distal end portion 32a of the valve tube 32 in the direction of the second end 14 of the male connector 10. As the luer tip 26 and the valve tube 32 move apart from one another, a space or gap can form between the luer tip 26 and the valve tube 32, permitting fluid to pass through the opening 38 into the fluid passageway 80 of the female connector 76, or vice versa.

In some embodiments, as mentioned above, as the valve struts 36 and luer tip 26 retract into the housing 22, the seal 44 can compress, causing the seal 44 to exert a biasing force on the luer tip 26 toward the closed position or causing the seal 44 to increase the biasing force that this seal 44 exerts on the luer tip 26. The biasing force from the seal 44 can be resisted by the radially extending surface 84 of the female connector 76 contacting the inner threads 56 of the housing 22. However, when the female connector 76 is withdrawn from the male luer 10, the seal 44 can return the sealing portion of the luer tip 26 to the closed position around the valve tube 32.

Despite the relative movement between the housing 22 and the luer tip 26, the sealing member 44 can be configured to maintain a fluid barrier between the outer surface of the tube 32 and the inner surface of the luer tip 26. In some embodiments, where the sealing member 44 comprises the generally rectangular protrusions the position of the sealing member 44 can be maintained by the protrusions. In some embodiments, the sealing member 44 can be positioned by adhering the outer surface of the protrusions to an inner surface of the luer tip 26. In some embodiments, the sealing member 44 can be positioned by adhering the outer surface of the seal 44 to an inner surface of the luer tip 26 or to an outer surface of the valve tube 32. Other suitable means of fixing the position of the sealing member 44 can also be used.

As shown in FIG. 2C, in the opened configuration, the fluid passageway 80 of the female connector 76 can communicate with the passageway 54 of the valve member 20 so as to allow fluid to flow through the passageway 54 and the fluid passageway 80 of the female connector 76 in either direction. Fluid can thereby flow from tubing (not shown) or another connector or conduit that can be attached to second end 14 of the luer connector 10, into the passageway 54 of the housing 22, around the valve base 34, through the interior space 60 within the luer tip 26, and through the opening 38 at the distal end portion 26a of the luer tip 26 and into the fluid passageway 80 of the female connector 76, and vice versa. In some embodiments, the substantially fluid-tight closure can also be formed between corresponding tapers of the outside surface of the tip 26 and the inner surface 86 of the female connector 76.

Figure 3A:
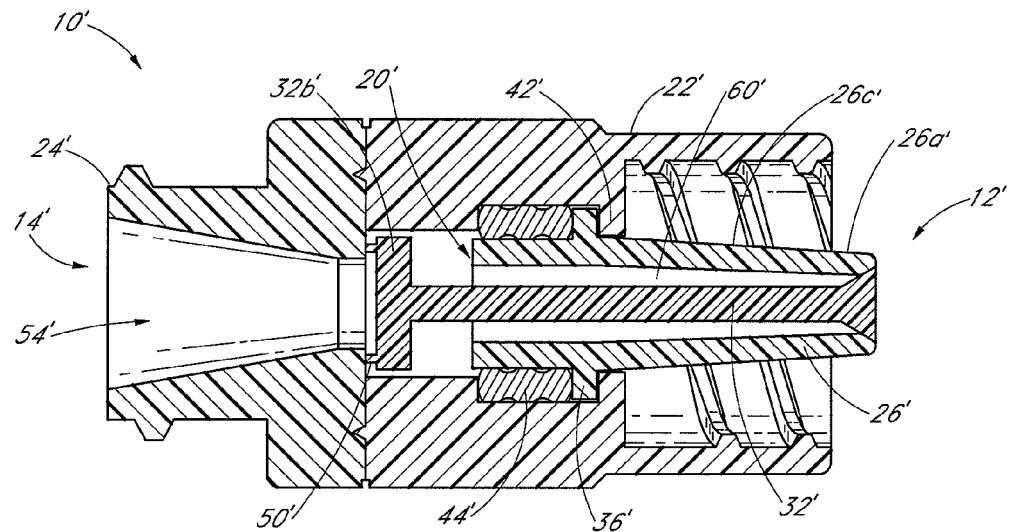
FIG. 3A is a cross-sectional view of another embodiment of a luer connector in a closed position.
Figure 3B:
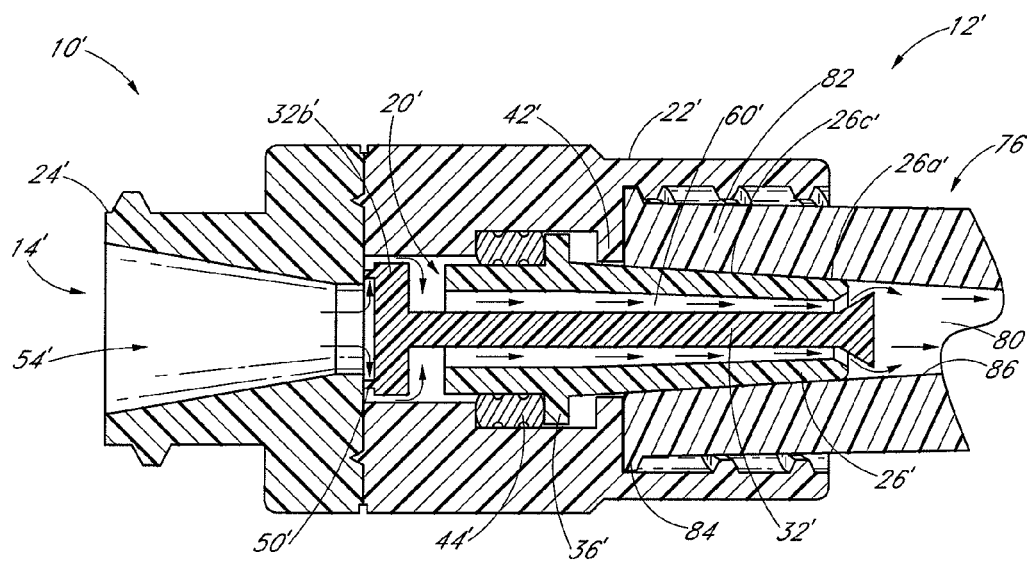
FIG. 3B is a cross-sectional view of the connector in FIG. 3A in an open position.

Referring now to FIGS. 3A-3B, some embodiments of the closeable luer connector 10' will be described in greater detail. In some embodiments, the luer connector 10' can comprise any of the components, features, materials, sizes, geometries, details, or configurations of any of the other luer connectors disclosed in FIGS. 1-11B and the associated written disclosure. FIG. 3A is a cross-sectional view of the luer connector 10' in a first or closed position. As described above, when the valve member 20' of the luer connector 10' is in the closed position, fluid is generally prevented from flowing through the luer connector 10'. FIG. 3B is a cross-sectional view of the embodiment of the luer connector 10' in a second or open position due to the engagement of a female connector 76 with the luer connector. The flow of fluid or medicament through the luer connector 10' is represented by arrows in FIG. 3B. As described above, when the valve member 20' of the luer connector 10' is in the open position, fluid can be generally permitted to flow through the luer connector 10'. As with any embodiment of the luer connector disclosed in FIGS. 1-11B and the associated written disclosure, a perfect seal by the valve member is not required, although such a seal may be preferred in some embodiments.

In some embodiments, the luer connector 10' can be the same or similar to the luer connector 10 described above, except for or in addition to the features and components illustrated and/or described below. First, in some embodiments, as in the illustrated embodiment, the luer tip 36' can be moved from the first, closed position (as illustrated in FIG. 3A) to the second, open position (as illustrated in FIG. 3B) without the use of the actuators or struts 36 as described above with respect to luer connector 10. With reference to FIG. 3B, the luer connector 10' can be threadedly engaged with the closeable female connector 76. The closeable female connector tip 82 of the female connector 76 can have a radially extending surface 84 disposed on its external surface that can engage with the inner threads formed on the inside surface of the shroud 28' of the luer connector 10' to engage the connectors 10', 76 as illustrated.

In some embodiments, as in the illustrated embodiment, the outside surface 26c' of the luer tip 26 can be tapered so that the distal end portion 26a' of the luer tip defines a smaller cross-sectional size or diameter than the portion of the luer tip 26' adjacent to the inner wall 42' of the housing 22'. Additionally, the inside surface 86 of the female connector 76 can be tapered, as illustrated, or can be cylindrical in shape, defining a uniform cross-sectional size or diameter. The female connector 76 can be engaged with the luer connector 10' by any suitable method, including, but not limited to, being threadingly engaged with the luer connector 10' as described above. The luer tip 26' can be configured such that, as the female connector 76 is engaged with the luer connector 10', at least a portion of the inside surface 86 of the female connector 76 will merge with and abut against a portion of the outside surface 26c' of the luer tip 26. At the point when a portion of the inside surface 86 of the female connector 76 has abutted against a portion of the outside surface 26c' of the luer tip 26, further engagement of the female connector 76 relative to the luer connector 10' can cause the luer tip 26' to retract axially toward the second end 14' of the luer connector 10', e.g., toward the open position (also referred to as the second position) as shown in FIG. 3B. In some embodiments, the luer tip 26' can be caused to rotate about the axial centerline of the luer connector 10' as the female connector 76 is increasingly threadingly engaged with the luer connector 10'. Conversely, as the female connector 76 is disengaged from the luer connector 10', the axial biasing force of the seal member 44' will preferably cause the luer tip 26' to return to the closed position (also referred to as the first position) relative to the valve tube 32'.

Figure 4A:
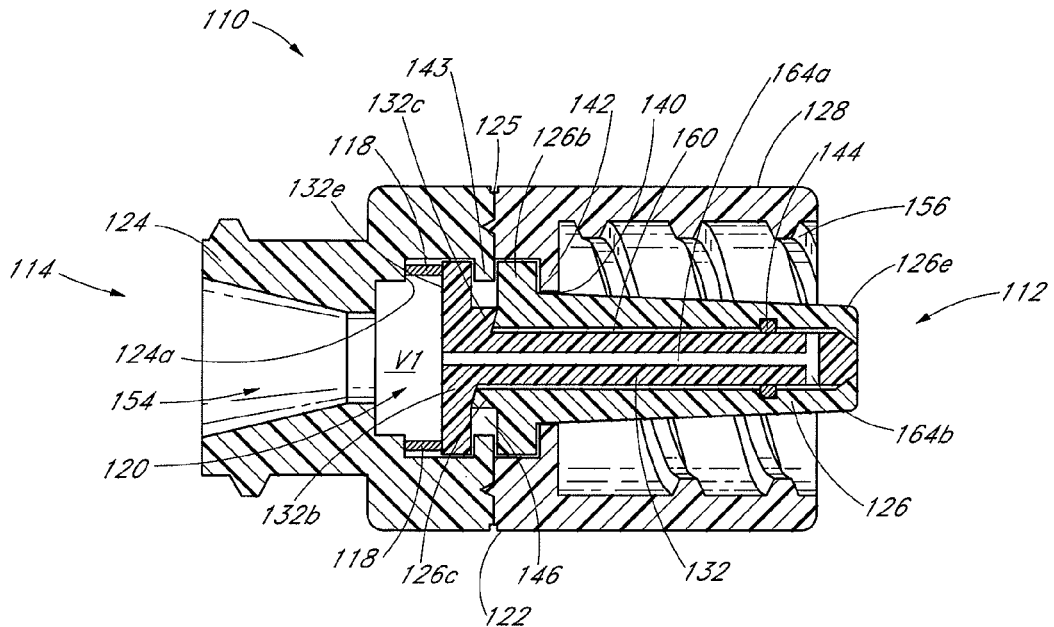
FIG. 4A is a cross-sectional view of another embodiment of a luer connector in a closed position.
Figure 4B:
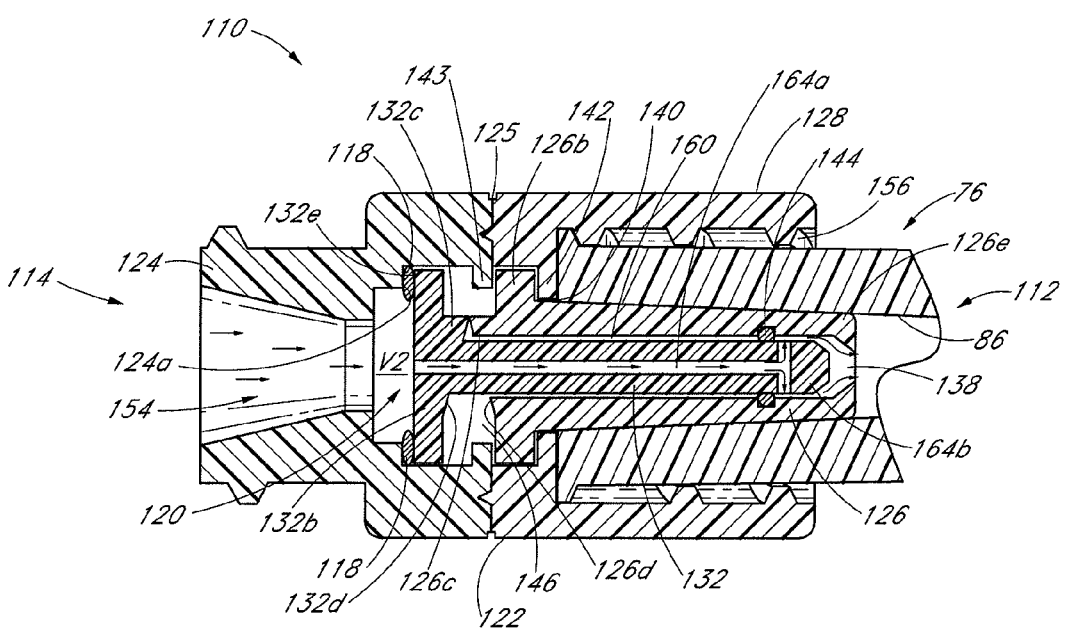
FIG. 4B is a cross-sectional view of the connector in FIG. 4A in an open position.

Referring now to FIGS. 4A-4F, some embodiments of the closeable luer connector 110 will be described. In some embodiments, the luer connector 110 can have any of the components, features, materials, sizes, geometries, details, or configurations of any of the other luer connectors disclosed in FIGS. 1-11B and the associated written disclosure. FIG. 4A is a cross-sectional view of the luer connector 110 in a closed position. As described above, when the valve member 120 of the luer connector 110 is in the closed position, fluid is generally prevented from flowing through the luer connector 110. FIG. 4B is a cross-sectional view of the embodiment of the luer connector 110 in an open position due to the engagement of a female connector 76 with the luer connector. The flow of fluid or medicament through the luer connector 110 is represented by arrows in FIG. 4B. As described above, when the valve tube 132 (also referred to as an internal member) of the luer connector 110 is in the open position, fluid can be generally permitted to flow through the luer connector 110. When the valve tube 132 is in a closed position, fluid can be generally prevented from flowing through the luer connector 110. As with any embodiment of the luer connector disclosed in FIGS. 1-11B and the associated written disclosure, a perfect seal by the valve member is not required, although such a seal may be preferred in some embodiments.

As illustrated in FIG. 4A, some embodiments of the assembled luer connector 110 can comprise a housing 122, a port member 124 positioned near the second end 114 of the luer connector 110, a luer tip 126 positioned near the first end 112 of the luer connector 110, a shroud 128 surrounding at least a portion of the luer tip 126, a seal 118, and a valve member 120. As illustrated, the seal 118 and the valve member 120 can be supported within the housing 122. In the illustrated embodiment, the valve member 120 can comprise a luer tip 126 and a valve tube 132. In some embodiments, the valve tube 132 can be positioned at least partially within the opening 138 that can be formed in the luer tip 126.

In some embodiments, as in the illustrated embodiment, the housing 122 can define an opening 140 through which the luer tip 126 can project. With reference to FIG. 4A, the luer connector 110 can be configured so that the luer tip 126 projects toward the first end 112 of the luer connector 110. The luer tip 126 is preferably co-axially aligned with the centerline of the housing 122, port member 124, and the shroud 128. The opening 140 can be sized and configured so as to provide radial support to the luer tip 126 so that the luer tip 126 remains generally co-axially aligned with the centerline of the housing 122. The luer connector 110 also can be configured so that the luer tip 126 is axially supported within the housing 122. Additionally, for reasons that will be described in greater detail below, the housing 122 and opening 140 can be sized and configured so that the luer tip 126 can freely rotate at least within a predetermined angular range relative to the housing 122 and shroud 128.

FIGS. 4C and 4D are a perspective view and a side view, respectively, of an embodiment the luer tip 126 of the embodiment of the luer connector 110. As most clearly illustrated in FIGS. 4C-4D, in some embodiments, the luer tip 126 can be formed so as to define a generally conical, tapered outside surface 126a projecting from a planar base portion 126b toward the first end 112 of the luer connector 110. Additionally, in some embodiments, the luer tip 126 can be formed so as to define a helical or angled portion 126c projecting from the base portion 126b toward the second end 114 of the luer connector 110. The angled portion 126c can define a generally planar angled surface 126d. As will be discussed below, the angled portion 126c can project from the base portion 126b to any length suitable to cause the valve tube 132 to move axially away from the luer tip 126 when the luer tip 126 is rotated relative to the valve tube 132, causing the luer connector 110 to change from the closed to the open position when the luer tip 126 is rotated relative to the valve tube 132.

The luer tip 126 can also be configured to define a generally cylindrical opening 160 through at least a portion of the luer tip 126, with the opening 160 being generally axially aligned with the axial centerline of the luer tip 126. The end portion 126e of the luer tip 126 preferably defines an angled or tapered surface 126f, wherein the inside surface of the luer tip 126 can be generally conical in shape so that the size of the opening 138 at the distal tip of the luer tip 126 is reduced relative to the portion of the opening 160 adjacent the opening 138.

FIGS. 4E and 4F are a perspective view and side view, respectively, of an embodiment a valve tube 132 of the embodiment of the luer connector 110. As most clearly illustrated in FIGS. 4E-4F, in some embodiments, the valve tube 132 can be formed so as to define a generally cylindrical outside surface 132a that is sized and configured to be received within a generally cylindrically shaped opening 160 that can be formed in the luer tip 126.

As illustrated in FIGS. 4E and 4F, the outside surface 132a of the valve tube 132 can project from the base portion 132b of the valve tube 132 toward the first end 112 of the luer connector 110. Additionally, the valve tube 132 can define a helical or angled portion 132c that projects toward the first end 112 of the luer connector 110 from the base portion 132b of the valve tube 132. The angled portion 132c can surround the outside surface 132a of the valve tube 132. The angled portion 132c can define a generally planar surface 132d that, in some embodiments, can be sized, angled, and configured to complement the angled portion 126c of the luer tip 126.

Alternatively, in some embodiments, either the luer tip 126 or the valve tube 132 can be formed so that either component defines a tab, pin, or other projection (not illustrated) instead of the angled portion 126c, 132c that substantially performs the same function as either angled portion. For example, in some embodiments, a tab, pin, or other projection (not illustrated) can project from the base portion 126b of the luer tip 126 toward the second end 114 of the luer connector 110 (instead of the angled portion 12bc) that can interact with the angled surface 132c of the valve tube 132 so as to cause the valve tube 132 to move away from the luer tip 126 and, hence, cause the opening 138 in the luer tip 126 to open as the luer tip 126 is rotated relative to the valve tube 132.

In some embodiments, the luer tip 126 can be axially and radially supported by the housing 122 in a manner that permits the luer tip 126 to rotate substantially freely relative to the housing 122, preferably within a defined angular range, but in a manner that substantially prevents axial movement of the luer tip 126 relative to the housing 122 and with enough rotational resistance to inhibit accidental opening of the connector 110. For example, detents can be formed on the luer connector 110 to inhibit accidental rotation of the male luer tip 126 relative to the housing 122. In some embodiments, the luer tip 126 can be configured to move axially relative to the housing 122. With reference to FIGS. 4A and 4B, the luer tip 126 can be axially supported by an internal wall 142 that can be formed on the inside of the housing 122 so as to prevent the luer tip 126 from translating axially toward the first end 112 of the luer connector 110 relative to the housing 122. Similarly, the luer tip 126 can be axially supported by an internal wall 143 that can be formed on the inside of the port member 124 so as to prevent the luer tip 126 from translating axially toward the second end 114 of the luer connector 110 relative to the housing 122. Additionally, in some embodiments, the port member 124 can be adhered, fused, welded, or otherwise attached to the housing 122 along the part line surface 125 after the luer tip 126 has been assembled within the housing 122.

The valve tube 132 can be supported within the housing 122 as shown in FIGS. 4A-4B. As illustrated therein, the valve tube 132 can be axially supported by an internal wall 143 that can be formed in the housing 122 so as to prevent the valve tube 132 from translating axially toward the first end 112 of the luer connector 110 relative to the housing 122. Additionally, the luer connector 110 can be configured so as to prevent the valve tube 132 from rotating relative to the housing 122 or port member 124. In particular, in some embodiments, the port member 124 and the base portion 132b of the valve tube 132 can define splines, channels, protrusions, tabs, pins, or other indexing features configured to prevent the valve tube 132 from rotating relative to the housing 122 or port member 124. As will be discussed in greater detail below, in some embodiments, the valve tube 132 is preferably prevented from rotating relative to the port member 124 or housing 122 so that the luer tip 126 can rotate relative to the valve tube 132 and cause the valve tube 132 to open and close in response to the rotation of the luer tip 126.

Additionally, with reference to FIGS. 4A and 4B, a seal 118 can be attached to the inside surface 124a of the port member 124 and to the base portion 132b of the valve tube 132. In some embodiments, the seal 118 can define an annular or cylindrical shape so that generally all of the fluid or medicament flowing through the port member 124 is caused to flow through the axial opening 164a in the valve tube 132 (e.g., so as to generally prevent fluid or medicament from flowing around the base portion 132b of the valve tube 132) and at least one opening 164b in communication with the axial opening 164a. The opening 164b can be positioned approximately transverse to the axial opening 164a and/or the valve tube 132. Additionally, in some embodiments, the seal 118 can be formed from a resilient material that exerts a biasing force on the valve tube 132 that biases the valve tube 132 toward the first end 112 of the luer connector 110 (e.g., biases the valve tube 132 toward the closed position relative to the luer tip 126).

With reference to FIG. 4D, the angled portion 126c of the luer tip 126 can define a planar surface 126d. In some embodiments, the surface 126d or surface 132d can be curved, or define other suitable shapes. As illustrated in FIG. 4D, the planar surface 126d can define an angle A1 relative to a horizontal reference plane. Similarly, with reference to FIG. 4F, the angled portion 132c of the valve tube 132 can define a planar surface 132d. As illustrated in FIG. 4F, the planar surface 132d can define an angle A2 relative to a horizontal reference plane. In some embodiments, the value of angle A1 can be approximately equal to the value of angle A2. In some embodiments, the value of the angle A1 can be different than the value of angle A2.

In some embodiments, the value of the angle A1 and/or A2 can be approximately 30 degrees. In some embodiments, the value of the angle A1 and/or A2 can be from approximately 15 degrees to approximately 75 degrees. In some embodiments, the value of angle A1 can be different as compared to the value of angle A2.

As will now be described in greater detail below, in the assembled configuration, as illustrated in FIGS. 4A and 4B, rotation of the luer tip 126 relative to the valve tube 132 can cause the valve member 120 of the luer connector 110 to move between the open position and the closed position. As mentioned above, in some embodiments, the seal 118 can exert a biasing force on the valve tube 132 that can cause the valve tube 132 to move into or remain in contact with the luer tip 126. In particular, the seal 118 can cause the planar surface 132d of the valve tube 132 to abut against the planar surface 126d, as is illustrated in FIGS. 4A and 4B. With reference to FIGS. 4A, 4D, and 4F, when the highest point 126d2 on the planar surface 126d (e.g., the point on the surface 126d that is furthest away from the base portion 126b) is approximately radially aligned with the lowest point 132d1 on the planar surface 132d (e.g., the point on the surface 132d that is closest to the base portion 132b) as is illustrated in FIG. 4A, the aft portion 132f of the valve tube 132 can generally be in sealing contact with the inside surface of the aft portion of the luer tip 126, so as to generally sealingly close the opening 138. Conversely, when the highest point 126d2 on the planar surface 126d is approximately radially aligned with the highest point 132d2 on the planar surface 132d (e.g., the point on the surface 132d that is furthest away from the base portion 132b) as is illustrated in FIG. 4B, the aft portion 132f of the valve tube 132 will preferably be spaced apart from the inside surface of the aft portion of the luer tip 126, so that the opening 138 is unsealed by the valve tube 132.

Accordingly, the relative rotation of the luer tip 126 with respect to the valve tube 132 can cause the valve tube 132 to move between the opened and closed position. In some embodiments, the luer tip 126 can be configured so as to define rotational limits or stops arranged to ensure that, as a female connector 76 is threadedly engaged with the luer connector 110 as described in greater detail below, the luer tip 126 stops rotating at a desired radial position wherein the valve tube 132 has opened a sufficient amount to permit fluid or medicament to flow through the luer connector 110. Similarly, the rotational limits or stops can be arranged to ensure that, as the female connector 76 is threadedly disengaged from the luer connector 110, the luer tip 126 stops rotating at a desired radial position that allows the valve tube 132 to sealingly close against the inside surface of the luer tip 126 by the bias force provided by the resilient seal 118. In particular, in some embodiments, the luer tip 126 and the housing 122 can define splines, channels, protrusions, tabs, pins, or other indexing features configured to control the range of rotation of the luer tip 126 relative to the housing 122. When the luer connector 110 is in the closed position, the outer surface of the distal portion 132a of the valve tube 132 can be sealingly closed against the inner surface of the distal portion of the luer tip 126 such that fluid can be generally prevented from flowing through the opening 138 formed in the distal end portion of the luer tip 126.

As mentioned, in the illustrated embodiment, the tube 132 can be slidably supported so as to translate axially within the luer tip 126. Further, an annular sealing member 144 can be positioned between the outside surface of the valve tube 132 and the inside surface of the luer tip 126 to prevent fluid from flowing into the chamber 146. The sealing member 144 can comprise any of the materials, geometries, sizes, or other details or configurations of any other seal or a sealing member disclosed in FIGS. 1-11B and the associated written disclosure. In some embodiments, the sealing member 144 can be formed from the same material as the valve tube 132 and can be formed integrally with the valve tube 132. In some embodiments, the sealing member 144 can be formed from a different material as compared to the valve tube 132. In some embodiments, the sealing member 144 can be formed separately from the valve tube 132 and positioned at the desired axial location of either the valve tube 132 or the inside surface of the luer tip 126. In some embodiments, the inside surface of the luer tip 126 and/or the outside surface of valve tube 132 can comprise features such as channels or depressions to secure the sealing member 144 in the desired location.

In some embodiments, the seal 118 can be resilient and biased toward an expanded position, as illustrated in FIG. 4A, so as to exert a force on the valve tube 132 that biases the valve tube 132 toward the closed position. In particular, in the illustrated embodiment, the seal 118 can bias the valve tube 132 to sealably close against the inside surface of the luer tip 126. Further, the seal 118 can be configured so that the volume generally contained within the interior portion of the seal 118 when the valve member 120 is in the closed position (which is represented by V1 in FIG. 4A) can be greater than the volume contained within the interior portion of the seal 118 when the valve member 120 is in the open position (which is represented by V2 in FIG. 4B). Thus, the volume of fluid contained within the interior portion of the seal 118 can decrease when the valve member 120 moves from the closed position to the open position and can increase when the valve member 120 moves from the open position to the closed position. By increasing the volume of space within the seal 118 as the valve member 120 moves to the closed position, the seal 118 can create reduced pressure or a force of suction that can reduce the amount of fluid or medicament that can flow through or drip out of the opening 138 as the valve member 120 is in the process of closing by drawing such fluid back into the volume of space within the interior of the seal 118.

In some embodiments, the seal 118, the tube 132, and the sealing member 144 can all be integrally formed from the same material. In some embodiments, however, any of these features can be formed separately and supported in the desired position as described above or in any other suitable manner. The housing 122 can be generally a tube-like structure with a passageway 154 that can extend from the second end 114 of the connector 110 through the axial center of the luer connector 110. As such, in some embodiments, when the luer connector 110 is in the open configuration as illustrated in FIG. 4B, the passageway 154 can permit fluid to flow from the second end 114 through the port member 124, the seal 118, the opening 164a in the tube 132, and out through the opening 138 in the luer tip 126 positioned at the first end 112 of the luer connector 110.

With reference to FIGS. 4A and 4B, near the second end 114 of the luer connector 110, the port member 124 and the corresponding section of the fluid passageway 154 can be sufficiently wide so as to accommodate a section of standard-diameter medical tubing inserted therein. The length, diameter, or other features and of the housing 122 (or any housing disclosed in FIGS. 1-11B and the associated written disclosure) can be the same as any other housing disclosed in FIGS. 1-11B and the associated written disclosure.

Additionally, the shroud 128 can be sized and configured as described above or as desired to securely or removably attach the luer connector 110 to another medical implement. Further, the housing 122, tip 126, seal 118, or any other components or features of the luer connector 110 can have or be made from any of the materials, shapes, features, sizes, or other configurations or details described with regard to any other tip member disclosed in FIGS. 1-11B and the associated written disclosure. As with other embodiments of the luer tip, the luer tip 126 can be made to comply with applicable standards and/or regulations, such as the ANSI and/or ISO standards.

With reference to FIG. 4B, as the male luer connector 110 and female connector 76 move towards each other into threaded engagement, the inside surface 86 of the female connector 76 can contact the outside surface of the luer tip 126. This can cause a fluid tight seal between the inside surface 86 of the female connector 76 and the outside surface of the luer tip 126. As the male luer connector 110 and female connector 76 move further into threaded engagement, the contact force between the inside surface 86 of the female connector 76 and the outside surface of the luer tip 126 can cause the luer tip 126 to rotate substantially in unison with the female connector 76. This can cause in the luer tip 126 to rotate relative to the valve tube 132, causing the distal end portion 132a of the valve tube 132 to move away from the interior distal end portion 126a of the luer tip 126, as described above. As the tube 132 and luer tip 126 move apart from one another, a gap can form between the tube 132 and the luer tip 126, permitting fluid to pass through the opening 138 into the fluid passageway 80 of the female connector 76, or vice versa.

As discussed above, as the valve tube 132 opens and causes the seal 118 to be compressed, the volume of fluid that can be contained within the seal 118 accordingly decreases. In some embodiments, when a constant source of positive pressure is imparted on the passageway 54 at the second end 114 of the luer connector 110, while the seal 118 is being compressed (which decreases the volume of fluid in the seal 118), the fluid within the seal 118 can be subjected to an increased pressure due to the compression of the seal 118. In some embodiments, this increased pressure can cause the fluid within the seal 118 to flow through the passageway 154 toward the first end 112 of the luer connector 110 at an increased rate, until the seal 118 is no longer being compressed.

Conversely, in some embodiments, when the female connector 76 is removed from the luer connector 110, the interaction between the inside surface 86 of the female connector 76 and the outside surface of the luer tip 126 can cause the luer tip 126 to rotate relative to the valve tube 132, causing the valve tube 132 to move to the closed position relative to the luer tip 126. As the valve tube 132 moves toward the closed position, the volume within the seal 118 can increase back to volume V1. The expansion of the interior volume of the seal 118 can cause a reduced pressure or suction to be generated within the seal 118, drawing at least some of the fluid that is within the opening 164a back into the volume of space within the seal 118. In some embodiments, the luer connector 110 may be used to control the flow of fluids or medicaments that are harmful or corrosive, such that preventing even a few drops from dripping out of the opening 138 as the female connector 76 is being removed can be beneficial.

Referring now to FIGS. 5A-5F, another embodiment of a closeable luer connector 210 will be described. FIG. 5A is a cross-sectional view of the luer connector 210, showing the luer connector 210 in a closed position. FIG. 5B is an end view of the luer connector 210, showing the luer connector 210 in a closed position. FIG. 5C is an end view of the luer connector 210, showing the embodiment of the luer connector in an open position. FIG. 5D is a cross-sectional view of the luer connector 210 taken through line 5D-5D in FIG. 5C, showing the luer connector 210 in an open position. FIG. 5E is a cross-sectional view of the luer connector 210 taken through line 5E-5E in FIG. 5C, showing the luer connector 210 in an open position. FIG. 5F is a perspective view of a portion of an embodiment of a valve tube 232 (also referred to as an internal member) of the luer connector 210.

In some embodiments, the luer connector 210 can have or be made from any of the components, features, materials, sizes, geometries, details, or configurations of any of the other luer connectors disclosed in FIGS. 1-11B and the associated written disclosure. As mentioned, FIG. 5A is a cross-sectional view of the luer connector 210 in a closed position so that fluid is generally prevented from flowing through the luer connector 210. FIG. 5D is a cross-sectional view of the embodiment of the luer connector 210 in an open position due to the engagement of a female connector 76 with the luer connector. The flow of fluid or medicament through the luer connector 210 is represented by arrows in FIG. 5D. As described above with reference to other luer connectors, when the valve tube 232 of the luer connector 210 is in the open position, fluid can be generally permitted to flow through the luer connector 210. Similarly, when the valve tube 232 is in a closed position, fluid can be generally prevented from flowing through the luer connector 210. As with any embodiment of the luer connector disclosed in FIGS. 1-11B and the associated written disclosure, a perfect seal by the valve member is not required, although such a seal may be preferred in some embodiments.

In some embodiments, the luer connector 210 can be the same or similar to the luer connector 110 described above, except for or in addition to the features and components illustrated and/or described below. Accordingly, in some respects, the luer connector 210 can operate in the same or similar manner as compared to the luer connector 110 described above. As illustrated in FIG. 5A, some embodiments of the assembled luer connector 210 can comprise a housing 222, a port member 224 positioned near the second end 214 of the luer connector 210, a luer tip 226 positioned near the first end 212 of the luer connector 210, a shroud 228 surrounding at least a portion of the luer tip 226, a seal 218, and a valve member 220. As illustrated, the seal 218 and the valve member 220 can be supported within the housing 222. In the illustrated embodiment, the valve member 220 can comprise a luer tip 226 and a valve tube 232. In some embodiments, the valve tube 232 can be positioned at least partially within the opening 260 that can be formed in the luer tip 226.

In some embodiments, as in the illustrated embodiment, the housing 222 can define an opening 240 through which the luer tip 226 can project. With reference to FIG. 5A, the luer connector 210 can be configured so that the luer tip 226 projects toward the first end 212 of the luer connector 210. The luer tip 226 is preferably co-axially aligned with the centerline of the housing 222, port member 224, and the shroud 228. The opening 240 can be sized and configured so as to provide radial support to the luer tip 226 so that the luer tip 226 remains generally co-axially aligned with the centerline of the housing 222. In some embodiments (not shown), a seal can be positioned between the outside surface of the luer tip 226 and the opening 240. The luer connector 210 also can be configured so that the luer tip 226 is axially supported within the housing 222. Additionally, for reasons that will be described in greater detail below, the housing 222 and opening 240 can be sized and configured so that the luer tip 226 can freely rotate completely around or within a predetermined angular range relative to the housing 222, the shroud 228, and the valve tube 232.

In some embodiments, the luer tip 226 can be formed so as to define a generally conical, tapered outside surface 226a projecting from a planar base portion 226b toward the first end 212 of the luer connector 210. Additionally, in some embodiments, the luer tip 226 can be formed so as to define an angled surface 226c on the inside of the end portion of the luer tip 226. As will be discussed below, the angled surface 226c can be configured to cause the valve tube 232 to move axially away from the luer tip 226 when the luer tip 226 is rotated relative to the valve tube 232, causing the luer connector 210 to change from the closed to the open position when the luer tip 226 is rotated relative to the valve tube 232. The luer tip 226 can also be configured to define a generally cylindrical opening 260 through at least a portion of the luer tip 226, with the opening 260 being generally aligned with the axial centerline of the luer tip 226.

In some embodiments, the valve tube 232 can be formed so as to define a generally cylindrical outside surface 232a that is sized and configured to be received within a generally cylindrically shaped opening 260 that can be formed in the luer tip 226. As illustrated in FIGS. 5A and 5D, the outside surface 232a of the valve tube 232 can project from the base portion 232b of the valve tube 232 toward the first end 212 of the luer connector 210. Further, as illustrated, the end portion of the valve tube 232 can define an angled, ovular, or other non-circular shape such that the distal end surface 232d of the valve tube 232 defines an ovular or other non-circular perimeter. Similarly, in some embodiments, the opening 238 formed in the end of the luer tip 226 can define an ovular, or other non-circular shape.

In some embodiments, the luer tip 226 can be axially and radially supported by the housing 222 in a manner that permits the luer tip 226 to rotate freely relative to the housing 222 preferably within a defined angular range, but in a manner that substantially prevents axial movement of the luer tip 226 relative to the housing 222. In some embodiments, the luer tip 226 can be configured to move axially relative to the housing 222. With reference to FIGS. 5A and 5D, the luer tip 226 can be axially supported by an internal wall 242 that can be formed on the inside of the housing 222 so as to prevent the luer tip 226 from translating axially toward the first end 212 of the luer connector 210 relative to the housing 222. Similarly, the luer tip 226 can be axially supported by an internal wall 243 that can be formed on the inside of the port member 224 so as to prevent the luer tip 226 from translating axially toward the second end 214 of the luer connector 210 relative to the housing 222. In some embodiments, the port member 224 can be adhered, fused, welded, or otherwise attached to the housing 222 along the part line surface 225 after the luer tip 226 has been assembled within the housing 222. In some embodiments, the housing 222 can define additional or different part lines so that all of the internal components such as the valve tube 232, the seal 218, and the luer tip 226 can be assembled therein.

The valve tube 232 can be supported within the housing 222 as shown in FIGS. 5A, 5B, and 5E. As illustrated therein, the valve tube 232 can be axially supported within an opening 241 that can be formed in the internal wall 243 of the housing 222 to laterally constrain the valve tube 232. As illustrated, a seal can be supported by the internal wall 243 to seal the opening 241. In the illustrated embodiment, the internal wall 243 can prevent the valve tube 232 from translating axially toward the first end 212 of the luer connector 210 relative to the housing 222. Additionally, the luer connector 210 can be configured so as to prevent the valve tube 232 from rotating relative to the housing 222 or port member 224. In particular, in some embodiments, the port member 224 and the base portion 232b of the valve tube 232 can define splines, channels, protrusions, tabs, pins, or other indexing features configured to prevent the valve tube 232 from rotating relative to the housing 222 or port member 224. As will be discussed in greater detail below, in some embodiments, the valve tube 232 can be prevented from rotating relative to the port member 224 or housing 222 so that the luer tip 226 can rotate relative to the valve tube 232 and cause the valve tube 232 to open and close in response to the rotation of the luer tip 226.

Additionally, with reference to FIGS. 5A and 5E, a seal 218 can be attached to the inside surface 224a of the port member 224 and to the base portion 232b of the valve tube 232. In some embodiments, the seal 218 can define an annular or cylindrical shape so that generally all of the fluid or medicament flowing through the port member 224 is caused to flow through the axial opening 264 and the transverse opening 264a in the valve tube 232 (e.g., so as to generally prevent fluid or medicament from flowing around the base portion 232b of the valve tube 232). Additionally, in some embodiments, the seal 218 can be formed from a resilient material that exerts a biasing force on the valve tube 232 that biases the valve tube 232 toward the first end 212 of the luer connector 210 (e.g., biases the valve tube 232 toward the closed position relative to the luer tip 226). In some embodiments, seal 218 can be a spring or other biasing device that biases the valve tube 232 towards the first end 212 of the luer connector 210, but does not contain fluid flowing through the connector 210. Rather, fluid would be prevented from flowing around the valve tube 232 toward the first end 212 by seal 241.

As will now be described in greater detail below, in the assembled configuration as illustrated in FIGS. 5A, 5D, and 5E, rotation of the luer tip 226 relative to the valve tube 232 can cause the valve member 220 of the luer connector 210 to move between the open position and the closed position. As mentioned above, in some embodiments, the seal 218 can exert a biasing force on the valve tube 232 that can cause the valve tube 232 to remain in contact with the luer tip 226. In particular, the seal 218 can cause the surface 232c of the valve tube 232 to abut against the surface 226c, as is illustrated in FIGS. 5A, 5D and 5E. In some embodiments, the luer connector 210 can be configured such that when the luer tip 226 is rotated, the valve tube 232 moves from an open to a closed, or from a closed to an open position, depending on the direction that the luer tip 226 is rotated. In particular, in some embodiments, the luer tip 226 can define an angled surface 226c that can have an ovular cross-section and the valve tube 232 can define an angled surface 232c that can also have an ovular cross-section. As with the other embodiments disclosed in FIGS. 1-11B and the associated written disclosure, in some embodiments, the luer tip 226 and the valve tube 232 can be manufactured at least in part from a rigid, medically neutral material such as plastic or metal. Preferably, rotation of the luer tip will cause the luer tip 226 and the valve tube 232 to translate relative to each other rather than deform and maintain their sealing relationship. As the luer tip 226 rotates in a first direction relative to the valve tube 232, the respective angled, ovular surfaces can cause the valve tube 232 to move toward the second end 214 of the luer connector 210. Similarly, when the valve tube 232 is an open position, as the luer tip 226 rotates in a second direction relative to the valve tube 232 that is opposite from the first direction, as the ovular shaped angled surface 232*c* of the valve tube 232 aligns with the ovular shaped angled surface 226*c* of the luer tip 226, the resilient seal 218 can cause the end portion of the valve tube 232 to become engaged with and, hence, substantially seal the opening 238 formed in the end portion of the luer tip 226.

Accordingly, the relative rotation of the luer tip 226 with respect to the valve tube 232 can cause the valve tube 232 to move between the opened and closed position. In some embodiments, the luer tip 226 can be configured so as to define rotational limits or stops arranged to ensure that, as a female connector 76 is threadedly engaged with the luer connector 210 as described in greater detail below, the luer tip 226 rotates to a desired radial position that causes the valve tube 232 to open a sufficient amount to permit fluid or medicament to flow through the luer connector 210. Similarly, the rotational limits or stops can be arranged to ensure that, as the female connector 76 is threadedly disengaged from the luer connector 210, the luer tip 226 rotates to a desired radial position allows the valve tube 232 to sealingly close against the inside surface of the luer tip 226 by the bias force provided by the resilient seal 218. In particular, in some embodiments, the luer tip 226 and the housing 222 can define splines, channels, protrusions, tabs, pins, or other indexing features configured to control the range of rotation of the luer tip 226 relative to the housing 222. When the luer connector 210 is in the closed position, the outer surface of the distal portion of the valve tube 232 can be sealingly closed against the inner surface of the distal portion 226*a* of the luer tip 226 such that fluid can be generally prevented from flowing through the opening 238 formed in the distal end portion of the luer tip 226.

As mentioned, in the illustrated embodiment, the tube 232 can be slidably supported so as to translate axially within the luer tip 226. Further, an annular sealing member 244 can be positioned between the outside surface of the valve tube 232 and the inside surface of the luer tip 226 to prevent fluid from flowing into the chamber 246. The sealing member 244 can comprise any of the materials, geometries, sizes, or other details of configurations of any other seal or a sealing member disclosed in FIGS. 1-11B and the associated written disclosure. In some embodiments, the sealing member 244 can be formed from the same material as the valve tube 232 and can be formed integrally with the valve tube 232. In some embodiments, the sealing member 244 can be formed from a different material as compared to the valve tube 232 and can be sealably attached thereto. In some embodiments, the sealing member 244 can be formed separately from the valve tube 232 and positioned at the desired axial location of either the valve tube 232 or the inside surface of the luer tip 226. In some embodiments, either the inside surface of the luer tip 226 or the outside surface of valve tube 232 can comprise features such as channels or depressions to secure the sealing member 244 in the desired location.

In some embodiments, as mentioned, the seal 218 can be resilient and biased toward an expanded position, as illustrated in FIG. 5A, so as to exert a force on the valve tube 232 that biases the valve tube 232 toward the closed position. In particular, in the illustrated embodiment, the seal 218 can bias the valve tube 232 to sealably close against the inside surface of the luer tip 226. Further, the seal 218 can be configured so that the volume generally contained within the interior portion of the seal 218 when the valve member 220 is in the closed position (which is represented by V1 in FIG. 5A) can be greater than the volume contained within the interior portion of the seal 218 when the valve member 220 is in the open position (which is represented by V2 in FIG. 5D). Thus, the volume of fluid contained within the interior portion of the seal 218 can decrease when the valve member 220 moves from the closed position to the open position and can increase when the valve member 220 moves from the open position to the closed position. By increasing the volume of space within the seal 218 as the valve member 220 moves to the closed position, the seal 218 can create a force of suction that can reduce the amount of fluid or medicament that can flow through or drip out of the opening 238 as the valve member 220 is in the process of closing by drawing such fluid back into the volume of space within the interior of the seal 218.

Embodiments wherein seal 218 does not substantially enclose a volume, for example when seal 218 is a spring, function in a similar manner. Chamber 246 is configured so that its volume when the valve member 220 is in the closed position is greater than its volume when the valve member 220 is in the open position. The change in volumes can draw fluid from the first end 212 of the luer connector 210 into the connector 210 as the connector 210 moves from the open to the closed positions.

In some embodiments, the seal 218, the tube 232, and the sealing member 244 can all be integrally formed from the same material. In some embodiments, however, any of these features can be formed separately and supported or attached in the desired position as described above or in any other suitable manner. The housing 222 can generally be a tube-like structure with a passageway 254 that can extend from the second end 214 of the connector 210 through the axial center of the luer connector 210. As such, in some embodiments, when the luer connector 210 is in the open configuration as illustrated in FIG. 5B, the passageway 254 can permit fluid to flow from the second end 214 through the port member 224, the seal 218, the opening 264 in the tube 232, and out through the opening 238 in the luer tip 226 positioned at the first end 212 of the luer connector 210.

With reference to FIGS. 5A and 5D, near the second end 214 of the luer connector 210, the port member 224 and the corresponding section of the fluid passageway 254 can be sufficiently wide so as to accommodate a section of standard-diameter medical tubing or a standard male luer inserted therein. The length, diameter, or other features and of the housing 222 (or any housing disclosed in FIGS. 1-11B and the associated written disclosure) can be the same as any other housing disclosed in FIGS. 1-11B and the associated written disclosure.

Additionally, the shroud 228 can be sized and configured as described above or as desired to securely or removably attached the luer connector 210 to another medical implement. Further, the housing 222, tip 226, seal 218, or any other components or features of the luer connector 210 can have or be made from any of the materials, shapes, features, sizes, or other configurations or details described with regard to any other tip member disclosed in FIGS. 1-11B and the associated written disclosure. As with other embodiments of the luer tip, the luer tip 226 can be made to comply with applicable standards and/or regulations, such as the ANSI and/or ISO standards.

With reference to FIG. 5D, as the male luer connector 210 and female connector 76 move towards each other into threaded engagement, the inside surface 86 of the female connector 76 can contact the outside surface of the luer tip 226. This can cause a fluid tight seal between the inside surface 86 of the female connector 76 and the outside surface of the luer tip 226. As the male luer connector 210 and female connector 76 move further into threaded engagement, the contact force between the inside surface 86 of the female connector 76 and the outside surface of the luer tip 226 can cause the luer tip 226 to rotate substantially in unison with the female connector 76. This can cause in the luer tip 226 to rotate relative to the valve tube 232 as described above, causing the distal end portion 232a of the valve tube 232 to move away from the interior distal end portion 226a of the luer tip 226, as described above. As the valve tube 232 and luer tip 226 move apart from one another, a gap can form between the outside surface of the end portion of valve tube 232 and the inside surface of the end portion of the luer tip 226, permitting fluid to pass through the opening 238 into the fluid passageway 80 of the female connector 76, or vice versa.

As discussed above, as the valve tube 232 opens and causes the seal 218 to be compressed, the volume of fluid that can be contained within the seal 218 can decrease. In some embodiments, when a constant source of positive pressure is imparted on the passageway 254 at the second end 214 of the luer connector 210, while the seal 218 is being compressed (which decreases the volume of fluid in the seal 218), the fluid within the seal 218 will be subjected to an increased pressure due to the compression of the seal 218. In some embodiments, this increased pressure can cause the fluid within the seal 218 to flow through the passageway 254 toward the first end 212 of the luer connector 210 at an increased rate, until the seal 218 is no longer being compressed.

Conversely, in some embodiments, when the female connector 76 is removed from the luer connector 210, the interaction between the inside surface 86 of the female connector 76 and the outside surface of the luer tip 226 can cause the luer tip 226 to rotate relative to the valve tube 232, causing the valve tube 232 to move to the closed position relative to the luer tip 226. As the valve tube 232 moves toward the closed position, the volume within the seal 218 can increase back to volume V1. The expansion of the interior volume of the seal 218 can cause a reduced pressure or suction to be generated within the seal 218. As mentioned, this reduced pressure or suction can cause the luer connector 210 to draw at least some of the fluid that is within the opening 264 back into the volume of space within the seal 218. In some embodiments, the luer connector 210 may be used to control the flow of fluids or medicaments that are harmful or corrosive, such that preventing even a few drops from dripping out of the opening 238 as the female connector 76 is being removed can be beneficial.

Figure 6F:
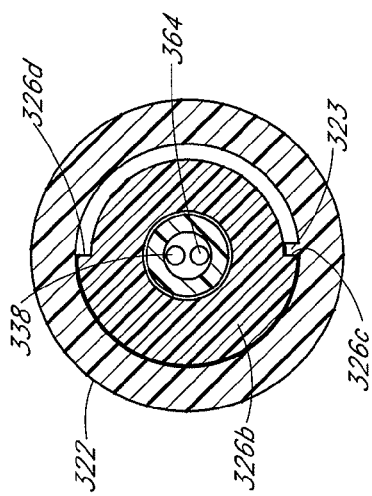
FIG. 6F is a cross-sectional view of the embodiment of the luer connector shown in FIG. 6A taken through line 6F-6F and in FIG. 6A.
Figure 6G:
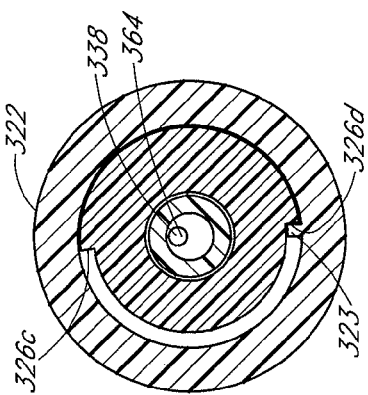
FIG. 6G is a cross-sectional view of the embodiment of the luer connector shown in FIG. 6A taken through line 6G-6G and in FIG. 6B.
Figure 6E:
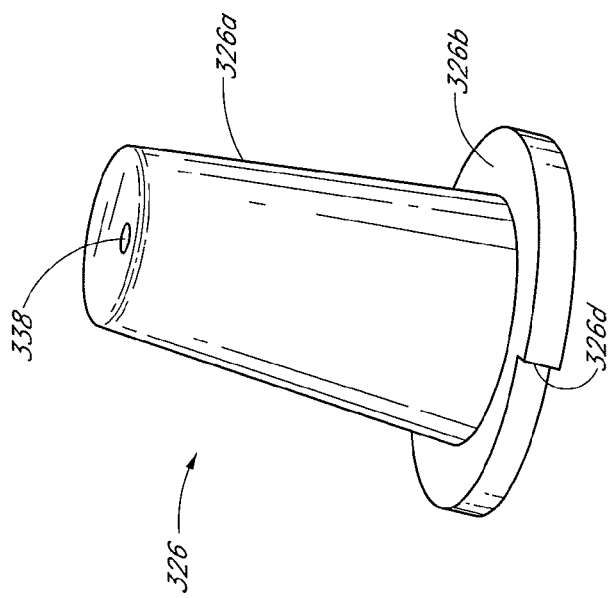
FIG. 6E is a perspective view of an embodiment of a luer tip of the embodiment of the luer connector shown in FIG. 6A.

Referring now to FIGS. 6A-6G, another embodiment of a closeable luer connector 310 will be described. FIG. 6A is a cross-sectional view of the luer connector 310, showing the luer connector 310 in a first or closed position. FIG. 6B is a cross-sectional view of the luer connector 310, showing the luer connector 310 in a second or open position. FIG. 6C is an end view of the embodiment of the luer connector 310, showing the luer connector 310 in a closed position. FIG. 6D is an end view of the luer connector 310, showing the luer connector 310 in an open position. FIG. 6E is a perspective view of an embodiment of a luer tip 326. FIG. 6F is a cross-sectional view of the luer connector 310 taken through line 6F-6F and in FIG. 6A, showing the luer connector 310 in a closed position. FIG. 6G is a cross-sectional view of the luer connector 310 taken through line 6G-6G and in FIG. 6B, showing the luer connector 310 in an open position.

In some embodiments, the luer connector 310 can have or be made from any of the components, features, materials, sizes, geometries, details, or configurations of any of the other luer connectors disclosed in FIGS. 1-11B and the associated written disclosure. FIG. 6A is a cross-sectional view of the luer connector 310 in a closed position so that fluid is generally prevented from flowing through the luer connector 310. FIG. 6B is a cross-sectional view of the embodiment of the luer connector 310 in an open position due to the engagement of a female connector 76 with the luer connector. The flow of fluid or medicament through the luer connector 310 is represented by arrows in FIG. 6B. As described above with reference to other luer connectors, when the valve tube 332 (also referred to as an internal member) of the luer connector 310 is in the open position, fluid can be generally permitted to flow through the luer connector 310. Similarly, when the valve tube 332 is in a closed position, fluid can be generally prevented from flowing through the luer connector 310. As with any embodiment of the luer connector disclosed in FIGS. 1-11B and the associated written disclosure, a perfect seal by the valve member is not required, although such a seal may be preferred in some embodiments.

In some embodiments, the luer connector 310 can be the same or similar to the luer connector 210 described above, except for or in addition to the features and components illustrated and/or described below. Accordingly, in some respects, the luer connector 310 can operate in the same or similar manner as compared to the luer connector 210 described above. As illustrated in FIG. 6A, some embodiments of the assembled luer connector 310 can comprise a housing 322, a port member 324 positioned near the second end 314 of the luer connector 310, a luer tip 326 positioned near the first end 312 of the luer connector 310, a shroud 328 surrounding at least a portion of the luer tip 326, and a valve member 320. As illustrated, the valve tube 332 can be integrally formed with the housing 322, or can be separately formed and attached to the housing 322 by any of the bonding or fusing techniques described in this disclosure or known in the art. The luer tip 326 can be supported within the housing 322. In the illustrated embodiment, the valve member 320 can comprise a luer tip 326 and a valve tube 332. In some embodiments, the valve tube 332 can be positioned at least partially within the opening 360 that can be formed in the luer tip 326.

In some embodiments, as in the illustrated embodiment, the housing 322 can define an opening 340 through which the luer tip 326 can project. With reference to FIG. 6A, the luer connector 310 can be configured so that the luer tip 326 projects toward the first end 312 of the luer connector 310. The luer tip 326 is preferably co-axially aligned with the centerline of the housing 322, port member 324, and the shroud 328. The opening 340 can be sized and configured so as to provide radial support to the luer tip 326 so that the luer tip 326 remains generally co-axially aligned with the centerline of the housing 322. The opening 340 can be sized and configured so as to not restrict the rotation of the luer tip 326 relative to the housing 322. The luer connector 310 also can be configured so that the luer tip 326 is axially supported within the housing 322. Additionally, for reasons that will be described in greater detail below, the housing 322 and opening 340 can be sized and configured so that the luer tip 326 can freely rotate within a predetermined angular range relative to the housing 322, the shroud 328, and the valve tube 332.

With reference to FIG. 6E, in some embodiments, the luer tip 326 can be formed so as to define a generally conical, tapered outside surface 326a projecting from a planar base portion 326b toward the first end 312 of the luer connector 310. With reference to FIG. 6F, in some embodiments, the planar base portion 326b can be formed so as to define a first abutment surface 326c and a second abutment surface 326d. Additionally, in some embodiments, the housing 322 can define a protrusion or tab 323 that can be generally longitudinally aligned with the first and second abutment surfaces 326c, 326d. As will be described in greater detail below, the tab 323 and the first and second abutment surfaces 326c, 326d can be configured to define or limit the angular range of rotation between the luer tip 326 and the housing 322. The luer tip 326 can also be configured to define a generally cylindrical opening 360 through at least a portion of the luer tip 326, with the opening 360 being generally aligned with the axial centerline of the luer tip 326.

In some embodiments, the valve tube 332 can be formed so as to define a generally cylindrical outside surface 332a that is sized and configured to be received within a generally cylindrically shaped opening 360 that can be formed in the luer tip 326. The outside surface 332a of the valve tube 332 can project from the housing 322 toward the first end 312 of the luer connector 310.

As mentioned, the luer tip 326 can be axially and radially supported by the housing 322 in a manner that permits the luer tip 326 to rotate substantially freely relative to the housing 322 in response to coupling to another connector or other manipulation, preferably within a defined angular range, but in a manner that substantially prevents axial movement of the luer tip 326 relative to the housing 322. As illustrated in other embodiments, opening 340 may include a resilient seal, for example an o-ring, which engages the rotating luer tip 326. In some embodiments, the port member 324 can be adhered, fused, welded, or otherwise attached to the housing 322 along the part line surface 325 after the luer tip 326 has been assembled within the housing 322. In some embodiments, the housing 322 can define additional or different part lines so that all of the internal components such as the valve tube 332, the seal 318, and the valve tube 326, and can be assembled therein.

As will now be described in greater detail below, in the assembled configuration, as illustrated in FIGS. 6A and 6B, rotation of the luer tip 326 relative to the valve tube 332 can cause the valve member 320 of the luer connector 310 to move between a second, open position and a first, closed position. In the open position, as illustrated in FIGS. 6B and 6D, the opening 338 in the luer tip 326 is generally aligned with the opening 364 in the valve tube 332. In the closed position, as illustrated in FIGS. 6A and 6C, the opening 338 in the luer tip 326 is generally out of alignment with respect to the opening 364 in the valve tube 332. In some embodiments, the luer connector 310 can be configured such that, when the luer tip 326 is rotated, the valve tube 332 moves from an open to a closed position, or from a close to an open position, depending on the direction that the luer tip 326 is rotated. The first and second abutment surfaces 326c, 326d can be configured so as to stop the rotation of the luer tip 326 in either a first or second direction so that the luer tip 326 is either aligned in an open position or a closed position relative to the valve tube 332 at the stop positions.

Accordingly, the relative rotation of the luer tip 326 with respect to the valve tube 332 can cause the valve member 320 to move between the opened and closed position. As mentioned, in some embodiments, the luer tip 326 can be configured so as to define a rotational limits or stops arranged to ensure that, as a female connector 76 is threadedly engaged with the luer connector 310 as described in greater detail below, the luer tip 326 rotates to a desired angular orientation that causes the valve tube 332 to open a sufficient amount to permit fluid or medicament to flow through the luer connector 310. Similarly, the rotational limits or stops can be arranged to ensure that, as the female connector 76 is threadedly disengaged from the luer connector 310, the luer tip 326 rotates to a desired radial position allows the valve tube 332 to sealingly close against the inside surface of the luer tip 326.

An annular sealing member 344 can be positioned between the outside surface of the valve tube 332 and the inside surface of the luer tip 326 to prevent fluid from flowing through the opening 360 toward the base portion 326b of the luer tip 326 and out through the opening 340. The sealing member 344 can comprise any of the materials, geometries, sizes, or other details or configurations of any other seal or a sealing member disclosed in FIGS. 1-11B and the associated written disclosure. In some embodiments, the sealing member 344 can be formed from the same material as the valve tube 332 or the luer tip 326 and can be formed integrally with the valve tube 332 or the luer tip 326. In some embodiments, the sealing member 344 can be formed independently and can be sealably attached to either the valve tube 332 or the luer tip 326. In some embodiments, the sealing member 344 can be formed separately from the valve tube 332 and positioned at the desired axial location of either the valve tube 332 or the inside surface of the luer tip 326. In some embodiments, either the inside surface of the luer tip 326 or the outside surface of valve tube 332 can comprise features such as channels or depressions to secure the sealing member 344 in the desired location.

The housing 322 can be generally a tube-like structure with a passageway 354 that can extend from the second end 314 of the connector 310 through the axial center of the luer connector 310. As such, in some embodiments, when the luer connector 310 is in the open configuration as illustrated in FIG. 6B, the passageway 354 can permit fluid to flow from the second end 314 through the port member 324, the seal 318, the opening 364a in the tube 332, and out through the opening 338 in the luer tip 326 positioned at the first end 312 of the luer connector 310. The length, diameter, or other features of the housing 32 can be the same as any other housing disclosed in FIGS. 1-11B and the associated written disclosure.

Additionally, the shroud 328 can be sized and configured as described above or as desired to securely or removably attached the luer connector 310 to another medical implement. Further, the housing 322, tip 326, seal 318, or any other components or features of the luer connector 310 can have or be made from any of the materials, shapes, features, sizes, or other configurations or details described with regard to any other tip member disclosed in FIGS. 1-11B and the associated written disclosure. As with other embodiments of the luer tip, the luer tip 326 can be made to comply with applicable standards and/or regulations, such as the ANSI and/or ISO standards.

With reference to FIG. 6B, as the male luer connector 310 and female connector 76 move towards each other into threaded engagement, the inside surface 86 of the female connector 76 can contact the outside surface of the luer tip 326. This can cause a fluid tight seal between the inside surface 86 of the female connector 76 and the outside surface of the luer tip 326. As the male luer connector 310 and female connector 76 move further into threaded engagement, the contact force between the inside surface 86 of the female connector 76 and the outside surface of the luer tip 326 can cause the luer tip 326 to rotate substantially in unison with the female connector 76. This can cause in the luer tip 326 to rotate relative to the valve tube 332 as described above, causing the opening 338 in the luer tip 326 to move relative to the opening 364 in the valve tube 332, as described above.

In some embodiments, the luer connector 310 can be configured to substantially prevent accidental rotational movement of the luer tip 326 from the first, closed position to prevent accidental opening of the connector 310 and, consequently, accidental discharge of fluid in the luer connector 310. For example, some embodiments of the luer connector 310 can have detents, notches, tabs, resilient members, or other features that inhibit the rotational movement of the luer tip 326 relative to the valve tube 332.

Figure 7A:
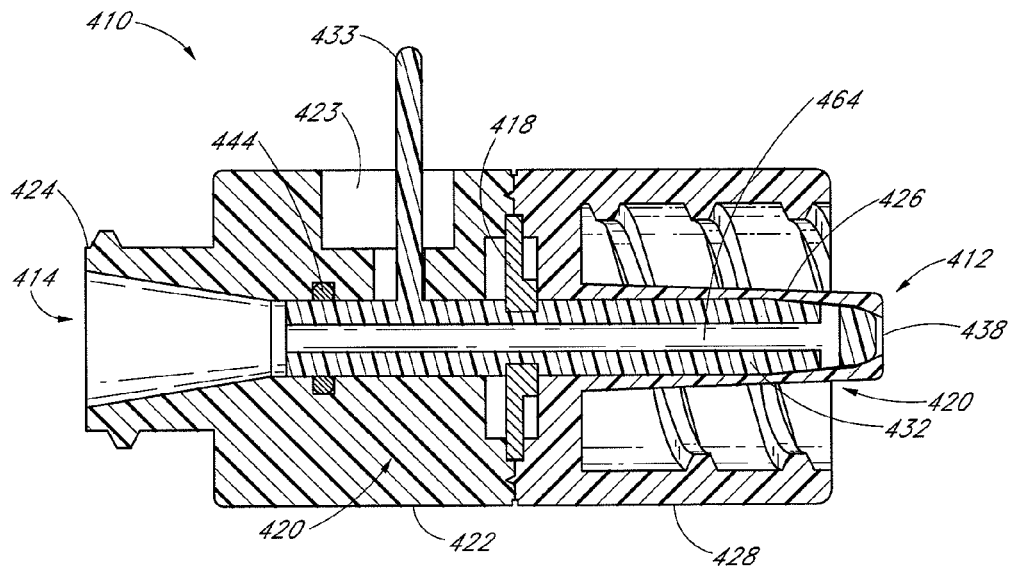
FIG. 7A is a cross-sectional view of another embodiment of a luer connector in a closed position.
Figure 7B:
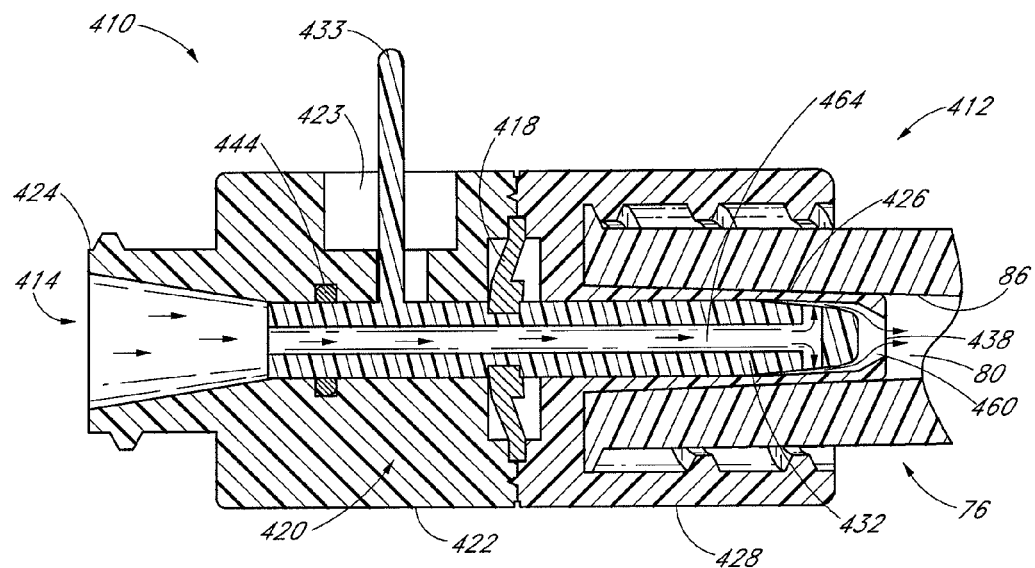
FIG. 7B is a cross-sectional view of the embodiment of the luer connector shown in FIG. 7A in an open position.

Referring now to FIGS. 7A-7B, another embodiment of a closeable luer connector 410 will be described. In some embodiments, the luer connector 410 can have or be made from any of the components, features, materials, sizes, geometries, details, or configurations of any of the other luer connectors disclosed in FIGS. 1-11B and the associated written disclosure. FIG. 7A is a cross-sectional view of the luer connector 410, showing the luer connector 410 in a closed position so that fluid is generally prevented from flowing through the luer connector 410. FIG. 7B is a cross-sectional view of the luer connector 410, showing the luer connector 410 in an open position so that fluid is generally permitted to flow through the luer connector 410. As will be described, in some embodiments, the luer connector 410 can be configured so that the luer connector 410 is manually changed between an open and a closed position, and is not automatically changed to an open position when the luer connector 410 is engaged with a female connector. The flow of fluid or medicament through the luer connector 410 is represented by arrows in FIG. 7B. As with any embodiment of the luer connector disclosed in FIGS. 1-11B and the associated written disclosure, a perfect seal by the valve member is not required, although such a seal may be preferred in some embodiments.

In some embodiments, the luer connector 410 can be the same or similar to the luer connector 10 described above, except for or in addition to the features and components illustrated in FIGS. 7A and 7B, and/or described below. Accordingly, in some respects, the luer connector 410 can operate in the same or similar manner as compared to the luer connector 10 described above. As illustrated in FIG. 7A, some embodiments of the assembled luer connector 410 can comprise a housing 422, a port member 424 positioned near the second end 414 of the luer connector 410, a luer tip 426 positioned near the first end 412 of the luer connector 410, a shroud 428 surrounding at least a portion of the luer tip 426, and a valve member 420. As illustrated, the luer tip 426 can be integrally formed with the housing 422 or, in some embodiments, the luer tip 426 can be separately formed and attached to the housing 422 by any of the bonding or fusing techniques disclosed in FIGS. 1-11B and the associated written disclosure or known in the art.

In the illustrated embodiment, the valve member 420 can comprise the luer tip 426, a valve tube 432 (also referred to as an internal member) supported within the luer tip 426, and a handle 433. In some embodiments, the valve tube 432 and the handle 433 can be integrally formed. In some embodiments, the handle 433 can be separately formed as compared to the valve tube 432 and attached to the valve tube 432 by any of the bonding or fusing techniques disclosed in FIGS. 1-11B and the associated written disclosure or known in the art. In some embodiments, the valve tube 432 can be positioned at least partially within the opening 460 that can be formed in the luer tip 426.

Similar to other luer connectors disclosed in FIGS. 1-11B and the associated written disclosure, the end portion of the valve tube 432 can be configured to create a substantially fluid tight seal with respect to the luer tip 426 when the valve member 420 is in the closed position. Additionally, when the valve member 420 is in the open position, fluid can be permitted to flow through the opening 464 formed in the valve tube 432 and out through the opening 438 formed in the luer tip 426. In some embodiments, the valve member 420 can be moved between the opened and closed positions by manually exerting a force on the handle 433 that can project through an opening or openings 423 in the housing 422. In particular, the valve member 420 can be opened by moving the handle 433 toward the second end 414 of the luer connector 410. Similarly, the valve member 420 can be closed by moving the handle 433 toward the first end 412 of the luer connector 410.

In some embodiments, the resilient seal member 418 can be supported by the housing 422 and configured to create a fluid tight seal around the outside surface of a portion of the valve tube 432. Additionally, the resilient seal number 418 can be configured to exert a biasing force on the valve tube 432 that biases the valve member 420 to the closed position. In some embodiments, the resilient seal member 418 can define a substantially planar, annular shape, having a circular opening therein that can constrict around the outside surface of a portion of the valve tube 432. An additional seal 444 can be positioned around a portion of the valve tube 432 near the second end 414 of the luer connector to substantially prevent fluid from leaking through the opening or openings 423 and the housing 422.

In some embodiments, the valve tube 432 and/or the housing 422 can be configured to define detents, stops, or other features to cause the valve member 420 to remain in the open or partially open position against the biasing force of the seal member 418, after the user has moved the valve member 420 to the open position. This can allow the valve member 420 to remain in the open position without requiring the user to hold the handle 433 in the open position. In some embodiments, exerting a force on the handle member in the direction of the first end 412 of the luer connector 410 can cause the valve member 420 to close. In some embodiments, the valve tube 432 and the housing 422 can be configured so that the user can hold the handle 433 in the open position to cause the valve member 420 to remain open.

Figure 8A:
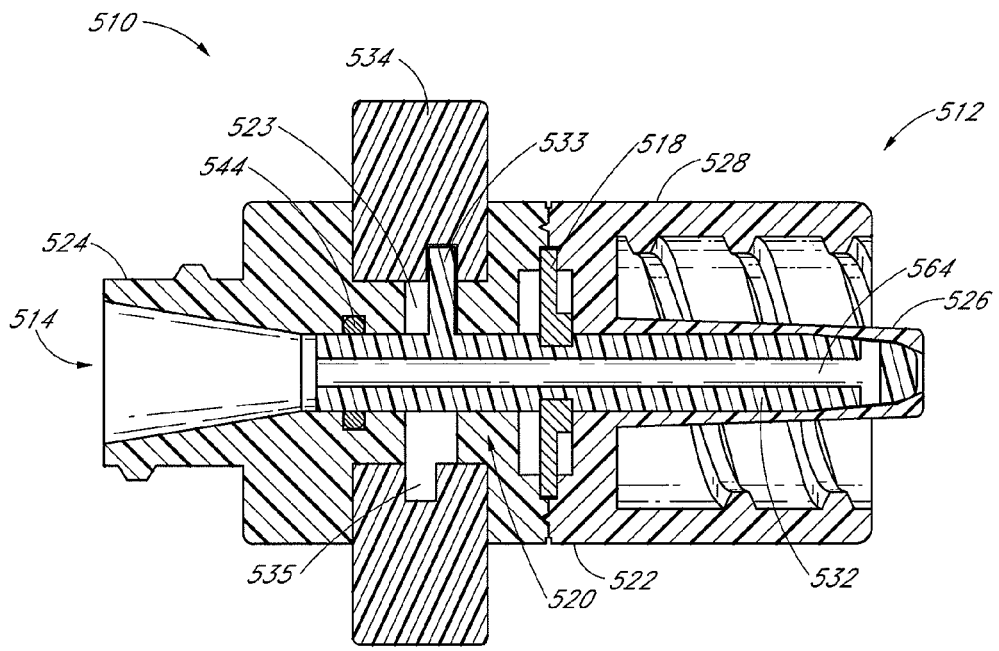
FIG. 8A is a cross-sectional view of another embodiment of a luer connector in a closed position.
Figure 8B:
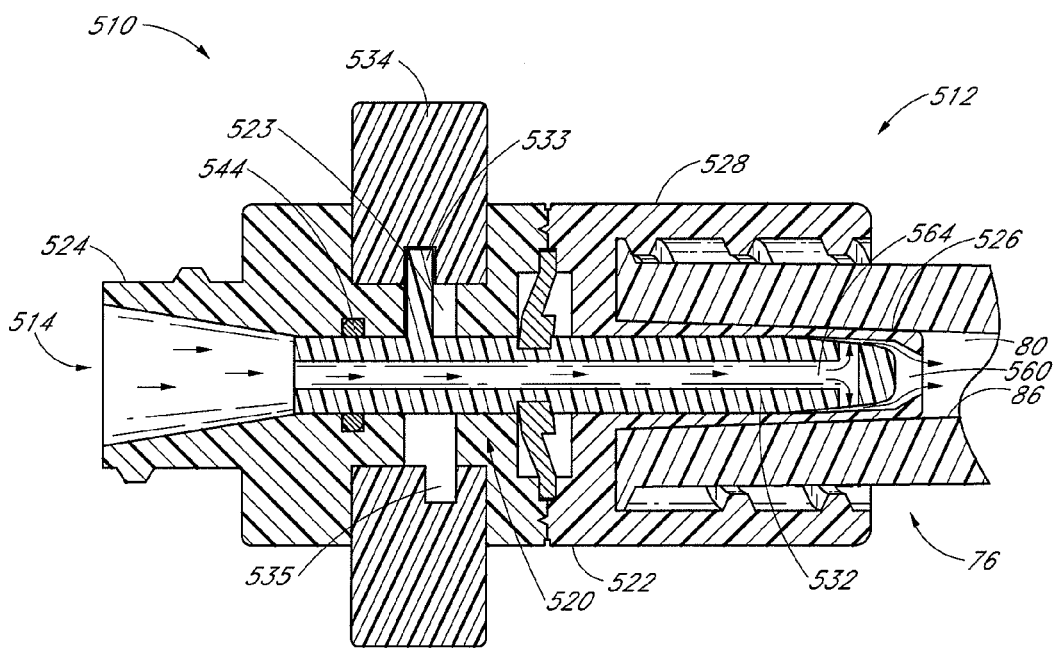
FIG. 8B is a cross-sectional view of the embodiment of the luer connector shown in FIG. 8A in an open position.

Referring now to FIGS. 8A-8B, another embodiment of a closeable luer connector 510 will be described. In some embodiments, the luer connector 510 can have or be made from any of the components, features, materials, sizes, geometries, details, or configurations of any of the other luer connectors disclosed in FIGS. 1-11B and the associated written disclosure. FIG. 8A is a cross-sectional view of the luer connector 510, showing the luer connector 510 in a closed position so that fluid is generally prevented from flowing through the luer connector 510. FIG. 8B is a cross-sectional view of the luer connector 510, showing the luer connector 510 in an open position so that fluid is generally permitted to flow through the luer connector 510. As will be described, in some embodiments, the luer connector 510 can be configured so that the luer connector 510 is manually changed between an open and a closed position, and is not automatically changed to an open position when the luer connector 510 is engaged with a female connector. The flow of fluid or medicament through the luer connector 510 is represented by arrows in FIG. 8B. As with any embodiment of the luer connector disclosed in FIGS. 1-11B and the associated written disclosure, a perfect seal by the valve member is not required, although such a seal may be preferred in some embodiments.

In some embodiments, the luer connector 510 can be the same or similar to the luer connector 410 described above, except for or in addition to the features and components illustrated in FIGS. 8A and 8B and/or disclosed in FIGS. 1-11B and the associated written disclosure. Accordingly, in some respects, the luer connector 510 can operate in the same or similar manner as compared to the luer connector 410 described above. As illustrated in FIG. 8A, some embodiments of the assembled luer connector 510 can comprise a housing 522, a port member 524 positioned near the second end 514 of the luer connector 510, a luer tip 526 positioned near the first end 512 of the luer connector 510, a shroud 528 surrounding at least a portion of the luer tip 526, and a valve member 520. As illustrated, the luer tip 526 can be integrally formed with the housing 522 or, in some embodiments, the luer tip 526 can be separately formed and attached to the housing 522 by any of the bonding or fusing techniques disclosed in FIGS. 1-11B and the associated written disclosure or known in the art.

In the illustrated embodiment, the valve member 520 can comprise the luer tip 526, a valve tube 532 (also referred to as an internal member) supported within the luer tip 526, a protrusion or tab 533, and a dial member 534. In some embodiments, the valve tube 532 and the tab 533 can be integrally formed. In some embodiments, the tab 533 can be separately formed as compared to the valve tube 532 and attached to the valve tube 532 by any of the bonding or fusing techniques disclosed in FIGS. 1-11B and the associated written disclosure or known in the art. The valve tube 532 can be positioned at least partially within the opening 560 that can be formed in the luer tip 526. In some embodiments, the valve tube 532 and the housing 522 can be configured to permit the valve tube 532 to translate axially within a predetermined range relative to the housing 522 so that the valve tube 532 can move between the open and closed positions. Additionally, the valve tube 532 and the housing 522 can define channels, notches, protrusions, indexing features, or otherwise be configured to substantially prevent the valve tube 532 from rotating relative to the housing 522.

Similar to other luer connectors disclosed in FIGS. 1-11B and the associated written disclosure, the end portion of the valve tube 532 can be configured to create a substantially fluid tight seal with respect to the luer tip 526 when the valve member 520 is in the closed position. Additionally, when the valve member 520 is in the open position, fluid can be permitted to flow through the opening 564 formed in the valve tube 532 and out through the opening 538 formed in the luer tip 526. In some embodiments, the valve member 520 can be moved between the opened and closed positions by manually exerting a force on the tab 533 that can project through an opening or series of openings 523 in the housing 522. In particular, the valve member 520 can be opened by moving the tab 533 toward the second end 514 of the luer connector 510, as will be described below. Similarly, the valve member 520 can be closed by moving the tab 533 toward the first end 512 of the luer connector 510.

In some embodiments, the resilient seal member 518 can be supported by the housing 522 and configured to create a fluid tight seal around the outside surface of a portion of the valve tube 532. Additionally, the resilient seal number 518 can be configured to exert a biasing force on the valve tube 532 that biases the valve member 522 to the closed position. In some embodiments, the resilient seal member 518 can define a substantially planar, annular shape, having a circular opening therein that can constrict around the outside surface of a portion of the valve tube 532. An additional seal 544 can be positioned around a portion of the valve tube 532 near the second end 514 of the luer connector to substantially prevent fluid from leaking through the opening or series of openings 523 and the housing 522.

In some embodiments, the dial member 534 can be formed from two or more pieces and snapped together or otherwise joined together around the housing 522 and the tab 533. The dial member 534 can be supported by the housing 522 in a manner that allows the dial to freely rotate relative to the housing 522 and the valve tube 532, while being axially supported by the housing 522 so that the dial member 534 is substantially prevented from translating in either axial direction relative to the housing 522. Additionally, the dial member 534 and/or the housing 522 can be configured to define detents, stops, or other features to bias or stop the dial member 534 at particular predetermined locations corresponding to desired positions of the valve member 520 such as, but not limited to, open, closed, and priming positions.

In some embodiments, the dial member 534 can define a helically shaped channel 535 configured to slidingly receive the tab 533. In this configuration, in some embodiments, because the valve tube 532 and tab 533 are substantially prevented from rotating relative to the housing, as the dial 534 is rotated, the helical shape of the channel 535 can cause the tab 533 and, hence, the valve tube 532, to move in either axial direction relative to the housing, depending on the direction that the dial 534 is rotated. In this manner, the valve member 520 can be caused to be moved between open and closed positions.

In some embodiments, as mentioned, the dial member 534 and/or the housing 522 can be configured to define detents, stops, or other features to cause the valve member 520 to remain in the open or partially open position against the biasing force of the seal member 518, after the user has moved the valve member 520 to the open position. This can allow the valve member 520 to remain in the open position without requiring the user to hold the dial member 534 in the desired position.

Figure 9A:
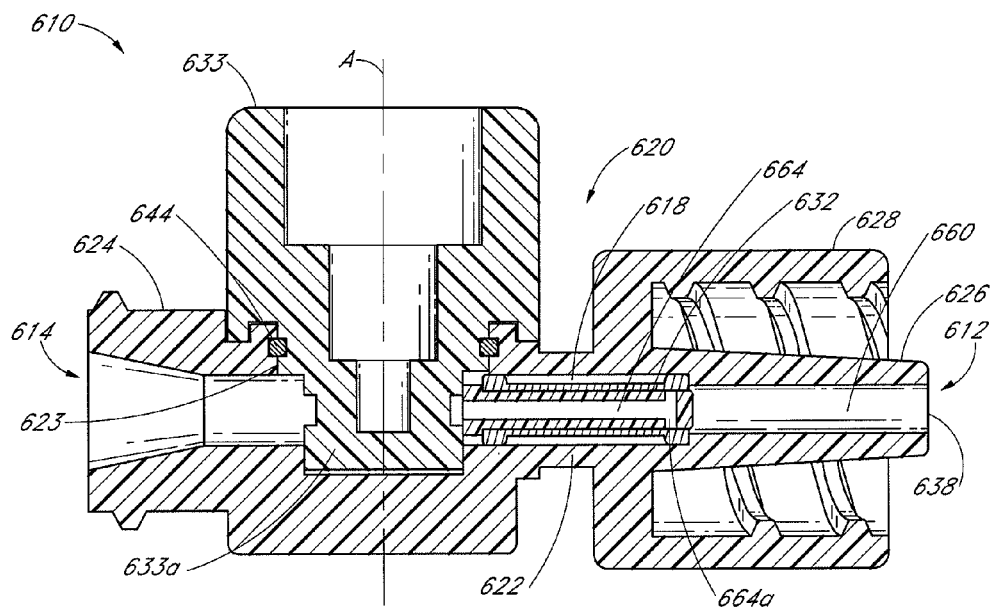
FIG. 9A is a cross-sectional view of another embodiment of a luer connector in a closed position.
Figure 9B:
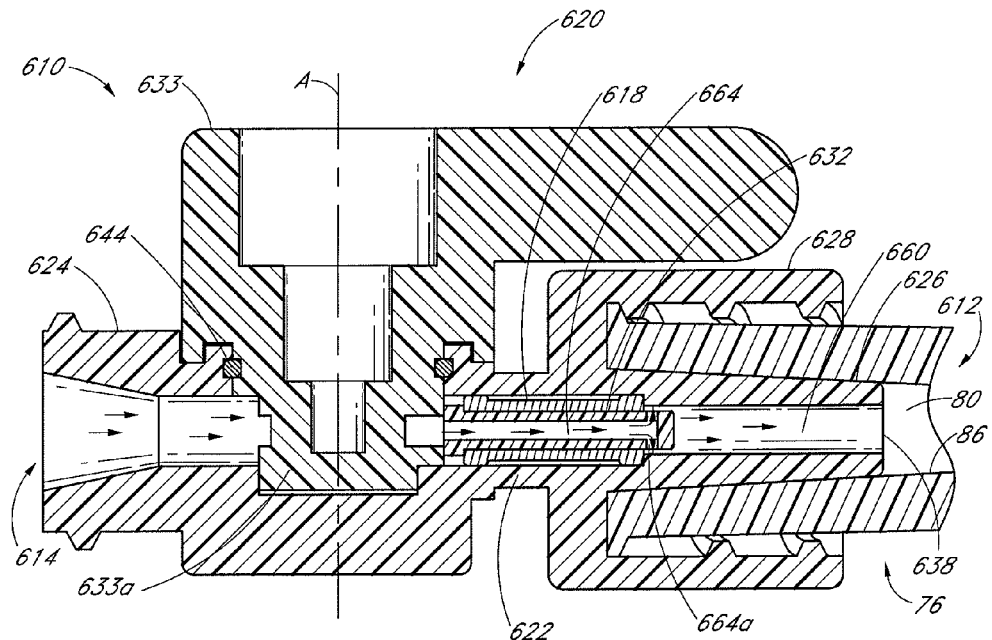
FIG. 9B is a cross-sectional view of the embodiment of the luer connector shown in FIG. 9A in an open position.

Referring now to FIGS. 9A-9B, another embodiment of a closeable luer connector 610 will be described. In some embodiments, the luer connector 610 can have or be made from any of the components, features, materials, sizes, geometries, details, or configurations of any of the other luer connectors disclosed in FIGS. 1-11B and the associated written disclosure. FIG. 9A is a cross-sectional view of the luer connector 610, showing the luer connector 610 in a closed position so that fluid is generally prevented from flowing through the luer connector 610. FIG. 9B is a cross-sectional view of the luer connector 610, showing the luer connector 610 in an open position so that fluid is generally permitted to flow through the luer connector 610. As will be described, in some embodiments, the luer connector 610 can be configured so that the luer connector 610 is manually changed between an open and a closed position, and is not automatically changed to an open position when the luer connector 610 is engaged with a female connector. The flow of fluid or medicament through the luer connector 610 is represented by arrows in FIG. 9B. As with any embodiment of the luer connector disclosed in FIGS. 1-11B and the associated written disclosure, a perfect seal by the valve member is not required, although such a seal may be preferred in some embodiments.

In some embodiments, the luer connector 610 can be the same or similar to the luer connector 510 described above, except for or in addition to the features and components illustrated in FIGS. 9A and 9B and/or described below. Accordingly, in some respects, the luer connector 610 can operate in the same or similar manner as compared to the luer connector 510 described above. As illustrated in FIG. 9A, some embodiments of the assembled luer connector 610 can comprise a housing 622, a port member 624 positioned near the second end 614 of the luer connector 610, a luer tip 626 positioned near the first end 612 of the luer connector 610, a shroud 628 surrounding at least a portion of the luer tip 626, and a valve member 620. As illustrated, the luer tip 626 can be integrally formed with the housing 622 or, in some embodiments, the luer tip 626 can be separately formed and attached to the housing 622 by any of the bonding or fusing techniques disclosed in FIGS. 1-11B and the associated written disclosure or known in the art.

In the illustrated embodiment, the valve member 620 can comprise the luer tip 626, a valve tube 632 (also referred to as an internal member) supported within the luer tip 626, and a stopcock or handle member 633. The valve tube 632 can be positioned at least partially within the opening 660 that can be formed in the luer tip 626. In some embodiments, the luer connector 610 can be configured to permit the valve tube 632 to translate axially within a predetermined range relative to the housing 622 and luer tip 626 so that the valve tube 632 can move between the open and closed positions.

A generally cylindrically shaped, resilient sealing member 618 can be supported within the housing 622 and/or luer tip 626. The sealing member 618 can be configured to sealingly cover the opening or openings 664a of the passageway 664 in the valve tube 632 so that, when the valve tube 632 is in the closed position as illustrated in FIG. 9A, the sealing member 618 substantially prevents any fluid or medicament from flowing out of the opening or openings 664a formed in the valve tube 632. Further, the sealing member 618 can be sized and configured to permit fluid or medicament to flow through the opening or openings 664a in the valve tube 632 and out through the opening 638 in the luer tip 626 when the valve member 620 is in the open position.

Additionally, the sealing member 618 can be supported within the housing 622 and configured to exert a biasing force on the valve tube 632 that biases the valve tube 632 to the closed position. In particular, the sealing member 618 can be supported by the luer tip 626 and/or housing 622 so that the sealing member 618 is in at least a slightly compressed state, so as to exert a biasing force on the valve tube 632 in the direction of the second end 614 of the luer connector 610. When the handle 633 is moved to the open position, as illustrated in FIG. 9B, the valve tube 632 can be moved toward the first end 612 of the luer connector 610 against the biasing force of the sealing member 618. As the handle 633 is moved from the open position to the closed position (illustrated in FIG. 9A), the biasing force of the sealing member 618 can restore the valve tube 632 to the closed position, preventing additional fluid from flowing through the valve member 620. In some embodiments, fluid can flow around the base of the handle 633 in either the open or closed position. An additional seal 644 can be positioned around a portion of the valve tube 632 near the second end 614 of the luer connector to substantially prevent fluid from leaking through the opening or series of openings 623 and the housing 622.

In some embodiments, the handle 633 can be supported by the housing 622 in a manner that allows the handle to rotate substantially freely relative to the housing 622 and the valve tube 632, while being supported by the housing 622 so that the handle 633 does not become inadvertently detached from the housing 622. Additionally, the handle 633 and/or the housing 622 can be configured to define detents, stops, or other features to bias or stop the handle 633 at particular rotational positions corresponding to desired positions of the valve member 620 such as, but not limited to, open, closed, and priming positions.

The base portion 633a of the handle 633 can define an ovular or otherwise non-circular cross-section or otherwise be configured so as to axially displace the valve tube 632 as the handle 633 is turned. As such, the radial distance from the axial centerline or center of rotation (represented by the axis A in FIGS. 9A and 9B) to the surface of the base portion 633a can vary from one point to another on the surface of the base portion 633a. In particular, in some embodiments, the distance between the center of rotation A to the point on the surface of the base portion 633a in contact with the valve tube 632 when the valve tube 632 is in the open position (as illustrated in FIG. 9B) can be greater than the distance between the center of rotation A to the point on the surface of the base portion 633a in contact with the valve tube 632 when the valve tube 632 is in the closed position (as illustrated in FIG. 9A). In this configuration, the valve member 620 can be moved between the open and closed position by rotating the handle 633 relative to the housing 622, thus causing the valve 620 to move between the opened and closed position.

In some embodiments, as mentioned, the handle 633 and/or the housing 622 can be configured to define detents, stops, or other features to cause the valve member 620 to remain in the open or partially open position against the biasing force of the seal member 618, after the user has moved the valve member 620 to the open position. This can allow the valve member 620 to remain in the open position without requiring the user to hold the handle 633 in the desired position.

Figure 10A:
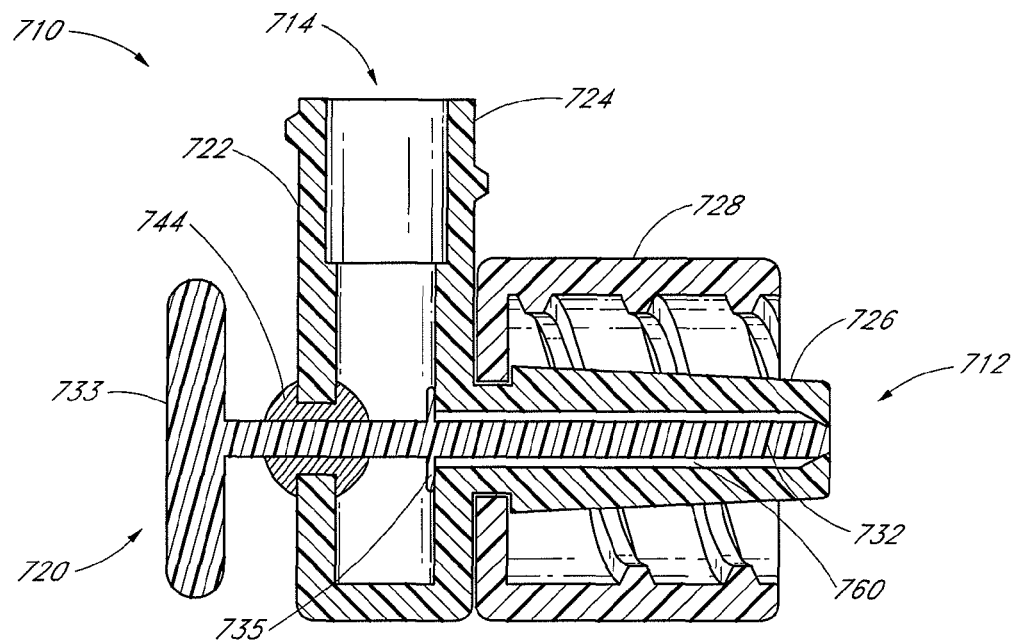
FIG. 10A is a cross-sectional view of another embodiment of a luer connector in a closed position.
Figure 10B:
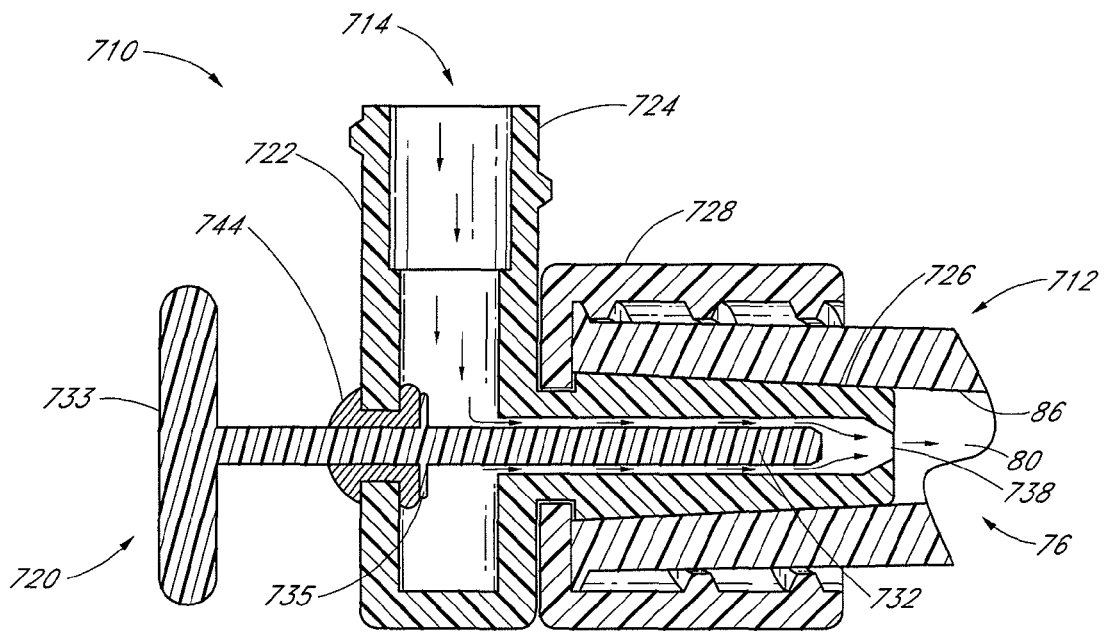
FIG. 10B is a cross-sectional view of the embodiment of the luer connector shown in FIG. 10A in an open position.

Referring now to FIGS. 10A-10B, another embodiment of a closeable luer connector 710 will be described. In some embodiments, the luer connector 710 can have or be made from any of the components, features, materials, sizes, geometries, details, or configurations of any of the other luer connectors disclosed in FIGS. 1-11B and the associated written disclosure. FIG. 10A is a cross-sectional view of the luer connector 710, showing the luer connector 710 in a closed position so that fluid is generally prevented from flowing through the luer connector 710. FIG. 10B is a cross-sectional view of the luer connector 710, showing the luer connector 710 in an open position so that fluid is generally permitted to flow through the luer connector 710. As will be described, in some embodiments, the luer connector 710 can be configured so that the luer connector 710 is manually changed between an open and a closed position, and is not automatically changed to an open position when the luer connector 710 is engaged with a female connector. The flow of fluid or medicament through the luer connector 710 is represented by arrows in FIG. 10B. As with any embodiment of the luer connector disclosed in FIGS. 1-11B and the associated written disclosure, a perfect seal by the valve member is not required, although such a seal may be preferred in some embodiments.

In some embodiments, the luer connector 710 can be the same or similar to the luer connector 10 described above, except for or in addition to the features and components illustrated in FIGS. 10A and 10B and/or described below. Accordingly, in some respects, the luer connector 710 can operate in the same or similar manner as compared to the luer connector 10 described above. As illustrated in FIG. 10A, some embodiments of the assembled luer connector 710 can comprise a housing 722, a port member 724 positioned near the second end 714 of the luer connector 710, a luer tip 726 positioned near the first end 712 of the luer connector 710, a shroud 728 surrounding at least a portion of the luer tip 726, and a valve member 720. As illustrated, the luer tip 726 can be integrally formed with the housing 722 or, in some embodiments, the luer tip 726 can be separately formed and attached to the housing 722 by any of the bonding or fusing techniques described in this disclosure or known in the art.

In the illustrated embodiment, the valve member 720 can comprise the luer tip 726, a valve tube 732 (also referred to as an internal member) supported within the luer tip 726, and a handle member 733. The valve tube 732 can be positioned at least partially within the opening 760 that can be formed in the luer tip 726. In some embodiments, the valve tube 732 and the housing 722 can be configured to permit the valve tube 732 to translate axially within a predetermined range relative to the housing 722 and luer tip 726 so that the valve tube 732 can move between the open and closed positions. In some embodiments, the valve tube 732 can define tabs, protrusions, or other features 735 to limit the axial displacement of the valve tube 732 away from the housing 722, so that the valve tube 732 is not inadvertently removed from the housing 722 as the valve tube 732 is being withdrawn. As such, the valve tube 732 can be moved between the opened and closed positions by manually pulling or pushing, respectively, on the handle 733 that can be integrally formed with or attached to the valve tube 732.

A generally fluid-tight sealing member 744 can be supported by the housing 722 and can be configured to seal the opening in the housing 722 through which the valve tube 732 can pass. In some embodiments, the sealing member 744 can be configured to provide a radial inward force on the outside surface of the valve tube 732 to impede the axial movement of the valve tube 732 relative to the housing 722. In some embodiments, the sealing member 744 can be configured to exert a biasing force on the valve tube 732 that biases the valve tube 732 to the closed position. The sealing member 744 can be designed so that a magnitude of the radial inward force is sufficient to prevent the valve member 720 from inadvertently opening from the closed position. Additionally, the sealing member 744 can be configured to substantially prevent any fluid or medicament from flowing out of the opening formed in the housing 722 through which the valve tube 732 can pass. In some embodiments, the valve tube 732, the seal 744, and/or the housing 722 can be configured to define detents, stops, or other features to bias the valve member 720 to remain in predetermined axial positions relative to the housing 722.

Referring now to FIGS. 11A-11B, another embodiment of a closeable luer connector 810 will be described. In some embodiments, the luer connector 810 can have or be made from any of the components, features, materials, sizes, geometries, details, or configurations of any of the other luer connectors disclosed in FIGS. 1-11B and the associated written disclosure. FIG. 11A is a cross-sectional view of the luer connector 810, showing the luer connector 810 in a closed position so that fluid is generally prevented from flowing through the luer connector 810. FIG. 11B is a cross-sectional view of the luer connector 810, showing the luer connector 810 in an open position so that fluid is generally permitted to flow through the luer connector 810. As will be described, in some embodiments, the luer connector 810 can be configured so that the valve member 820 of the luer connector 810 can be automatically changed between an open and a closed position. The flow of fluid or medicament through the luer connector 810 is represented by arrows in FIG. 11B. When the valve tube 832 (also referred to as an internal member) of the luer connector 810 is in the open position, fluid can be generally permitted to flow through the luer connector 810. Similarly, when the valve tube 832 is in a closed position, fluid can be generally prevented from flowing through the luer connector 810. As with any embodiment of the luer connector disclosed in FIGS. 1-11B and the associated written disclosure, a perfect seal by the valve member is not required, although such a seal may be preferred in some embodiments.

In some embodiments, the luer connector 810 can be the same or similar to the luer connector 10 described above, except for or in addition to the features and components illustrated in FIGS. 11A and 11B and/or described below. Accordingly, in some respects, the luer connector 810 can operate in the same or similar manner as compared to the luer connector 10 described above. As illustrated in FIG. 11A, some embodiments of the assembled luer connector 810 can comprise a housing 822, a port member 824 positioned near the second end 814 of the luer connector 810, a luer tip 826 positioned near the first end 812 of the luer connector 810, a shroud 828 surrounding at least a portion of the luer tip 826, and a valve member 820. As illustrated, the valve tube 832 can be integrally formed with the port member 824 or, in some embodiments, the valve tube 832 can be separately formed and attached to the port member 824 by any of the bonding or fusing techniques described in this disclosure or known in the art.

In the illustrated embodiment, the valve member 820 can comprise the luer tip 826 and the valve tube 832 supported within the luer tip 826. The valve tube 832 can be positioned at least partially within the opening 860 that can be formed in the luer tip 826. In some embodiments, the luer tip 826 and the housing 822 can be configured to permit the luer tip 826 to translate axially within a predetermined range relative to the housing 822 and valve tube 832 so that the valve member 820 can move between the open and closed positions. In some embodiments, the luer tip 826 can define tabs, protrusions, or other features 835 to engage the end portion of the female connector 76 so that luer tip 826 can be retracted when the female connector 76 is threadedly engaged with the luer connector 810, as will be described below. As will be described, the luer tip 826 can be moved between the opened and closed positions by threadedly engaging or disengaging, respectively, a female connector 76 with the luer connector 810.

A generally fluid-tight sealing member 844 can be supported by the valve tube 832 and can be configured to seal the opening 860 between the outside surface of the valve tube 832 and the inside surface of the luer tip 826 so that fluid is generally prevented from flowing into the chamber 856 and inside the housing 822. In some embodiments, the luer tip 826 can be configured to be biased toward a closed position such that, as the female connector 76 is removed from the luer connector 810, the luer tip 826 automatically returns to the closed position.

With reference to FIG. 11B, as the male luer connector 810 and female connector 76 move towards each other into threaded engagement, the inside surface 86 of the female connector 76 can contact the outside surface of the luer tip 826 or the end portion of the female connector 76 can contact the tabs 835 formed on the outside surface of the luer tip 826. This can cause a fluid tight seal between the inside surface 86 of the female connector 76 and the outside surface of the luer tip 826. As the male luer connector 810 and female connector 76 move further into threaded engagement, the contact force between the female connector 76 and the luer tip 826 can force the luer tip 826 to retract so that the pliable end portion 826a of the luer tip 826 is stretched around the valve tube 832 and the opening or slit 838 in the pliable end portion 826a of the luer tip 826 is caused to be opened, thus exposing the openings 864a in the valve tube 832 and allowing fluid to flow into the female connector 76. As the female connector 76 is removed from the luer connector 810, the luer tip 826 preferably returns to its closed position.

Any features of the embodiments shown and/or described in FIGS. 1-11B that have not been expressly described in this text, such as distances, proportions of components, etc. are also intended to form part of this disclosure. Additionally, although this invention has been disclosed in the context of various embodiments, features, aspects, and examples, it will be understood by those skilled in the art that the present invention extends beyond the specifically disclosed embodiments to other alternative embodiments and/or uses of the invention and obvious modifications and equivalents thereof. Accordingly, it should be understood that various features and aspects of the disclosed embodiments can be combined with, or substituted for, one another in order to perform varying modes of the disclosed inventions. Thus, it is intended that the scope of the present invention disclosed in FIGS. 1-11B and the associated written disclosure should not be limited by the particular disclosed embodiments described above.

In some embodiments, the male luer includes closing mechanisms which function to prevent and/or impede fluid from escaping from or entering into the male luer, while allowing fluid flow when the male luer is manually opened or engaged with a corresponding female luer. As used herein in describing FIGS. 12A-19D, terms such as "closed" or "sealed" should be understood as obstructions or barriers to fluid flow. These terms should not be understood to require that a particular structure or configuration achieves a complete fluid closure in all circumstances.

Some medications, including those used during chemotherapy, can be harmful to a patient in certain applications. For example, exposure to the skin can sometimes result in a chemical burn. Inhalation of aerosolized forms of some medications also can be harmful. Thus, control over the containment of the medication is highly desirable.

At present, some potentially harmful medications are distributed in sealed vials. The medication can be removed from the vial by inserting a needle and drawing the medication into a syringe. The needle can be then withdrawn from the vial and the medication can be dispensed. However, when the needle is inserted into the medication for drawing into the syringe, the needle may be withdrawn with a residue of medication disposed on the outside of the needle. This medication can inadvertently come in contact with the skin and cause harm. Or, if a vial adapter is used to penetrate the vial with a withdrawal mechanism, the medication can be drawn through the mechanism and passed directly to a syringe for injection without the additional step of withdrawing the mechanism from the vial. However, even if such a vial adapter is used, there is still the possibility of latent medication remaining on the end of the syringe used to inject the medication, on the mechanism after the vial is decoupled, or on the mechanism after the syringe is decoupled.

Figure 12A:
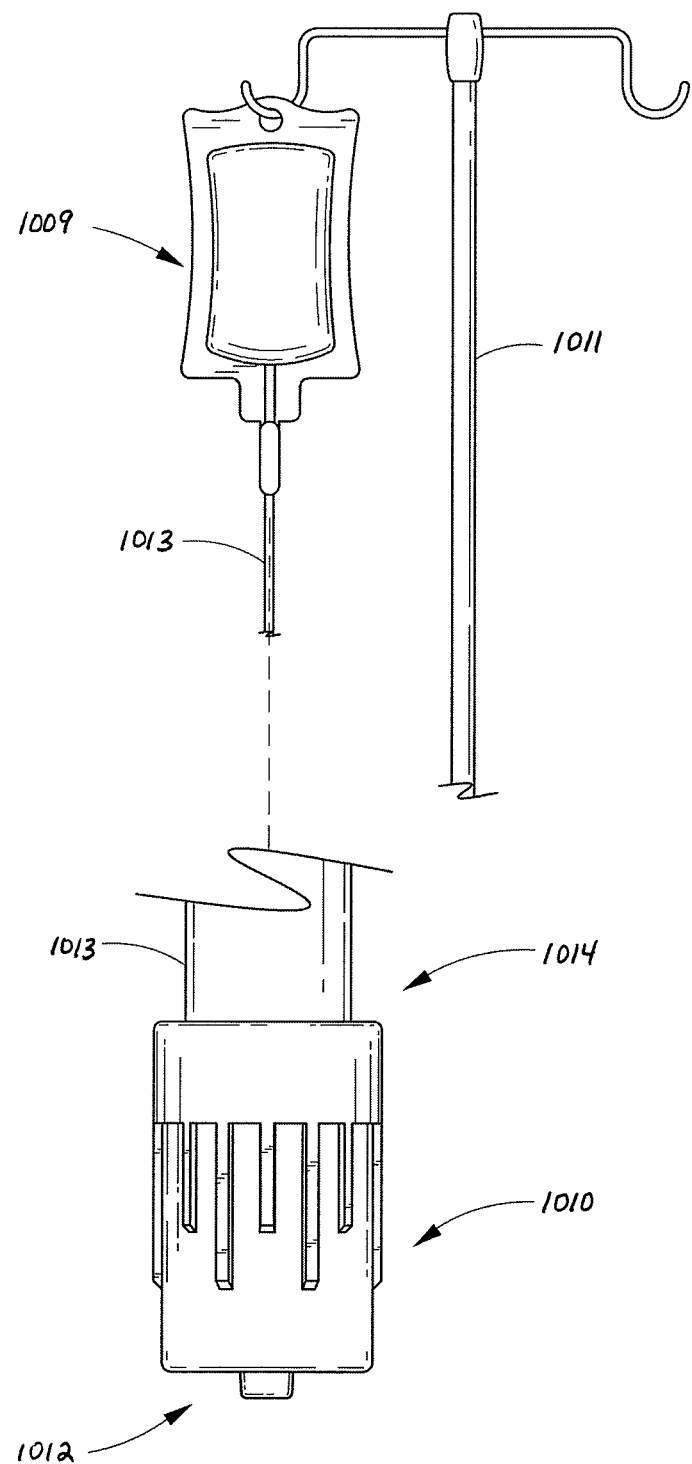
FIG. 12A is a perspective view of an embodiment of a male luer connector attached to tubing configured to receive fluid from a hanging gravity-fed IV bag. In this and other figures, the relative size of the connector and attached tubing is increased in comparison to other objects to facilitate viewing certain details.

FIG. 12A is a perspective view of an embodiment of a male luer connector in an example of use in which it is attached to tubing configured to receive fluid from a hanging gravity-fed IV bag. In FIG. 12A, an embodiment of a closeable male luer connector 1010 is shown in a closed position. The luer connector 1010 can be attached to a gravity-fed IV bag 1009 filled with fluid hanging from a pole stand 1011. At the bottom of the bag 1009, a section of tubing 1013 can be attached. The opposite end of the tubing 1013 can be connected to the second or distal end 1014 of the luer connector 1010. A closing mechanism on the interior of the first or proximal end 1012 of the luer connector 1010 can prevent the fluid contained within the bag 1009 from flowing through the tubing 1013 and leaking out of the luer connector 1010, as long as the luer connector 1010 remains in a closed configuration.

The IV delivery system illustrated in FIG. 12A can be easily readied for fluid communication with a patient. In most circumstances, the tubing 1013 is filled with air when it is initially connected to the IV bag 1009. If the other end of the tubing 1013 can be connected to a closed connector, as illustrated in FIG. 12A, the air cannot escape and fluid cannot enter the tubing 1013 from the IV bag 1009. In some embodiments, the luer connector 1010 can be manipulated so as to be in the open position until all of the air has been purged through the luer 1010 and the fluid in the IV bag 1009 fills the tubing 1013 and connector 1010. This procedure is known as "priming." As soon as the fluid line and connector are properly primed, the health care provider can then manipulate the luer connector 1010 to the closed position to stop the flow of fluid through the luer connector 1010.

Figure 12B:
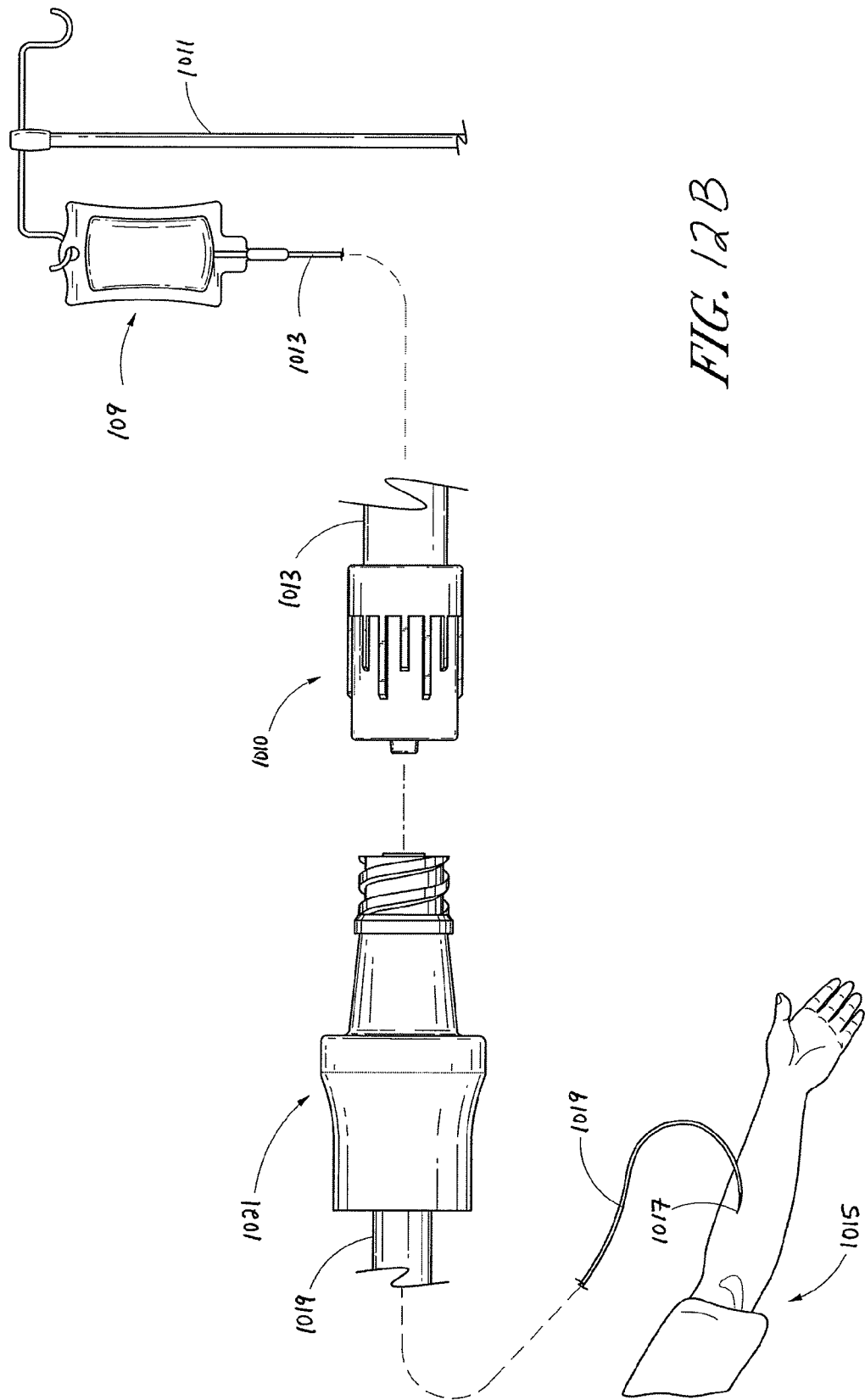
FIG. 12B shows a perspective view of an embodiment of the male luer connector of FIG. 12A being connected to an example of a female connector attached to tubing inserted into a patient.

FIG. 12B shows a perspective view of an embodiment of the male luer connector of FIG. 12A being connected to an example of a female connector attached to tubing inserted into a patient. Referring now to FIG. 12B, a catheter 1017 has been inserted into a patient's arm 1015. The catheter 1017 penetrates the skin of the arm 1015 and can be fluidly connected with the patient's bloodstream. The catheter 1017 can also be connected to a length of medical tubing 1019 attached to a female medical connector 1021. The example of a female medical connector 1021 illustrated in FIG. 12B is a version of the Clave® connector manufactured by ICU Medical, Inc., San Clemente, California. Various embodiments of a connector of this type are illustrated and described in U.S. Pat. No. 5,685,866, which is incorporated by reference herein its entirety. It is contemplated that many of the male luer embodiments disclosed in FIGS. 12A-19D and the associated written disclosure can be used with other types of female connectors. The tubing 1019, catheter 1017, and female connector 1021 were preferably previously primed with fluid using standard procedures. The luer connector 1010 can be primed as described previously and brought into engagement with the female connector 1021. As described in further detail below, when the male connector 1010 and female connector 1021 are engaged, fluid can be permitted to flow from the IV bag 1009 into the patient. When the male connector 1010 and female connector 1021 are disengaged, fluid can be once again prevented from flowing out of the first end 1012 of the male connector 1010. In general, fluid can also be prevented from flowing out of the opening in the female connector 1021.

The embodiment illustrated in FIGS. 12A-12B is described in further detail below. Each of the other embodiments disclosed in FIGS. 12A-19D and the associated written disclosure can be used in the illustrated fluid system, and in various modifications and alternatives thereof. Further, it is contemplated that the various embodiments of connectors can be used in a wide variety of additional medical fluid systems. For example, the disclosed connectors can also be used to transfer bodily fluids such as blood, urine, or insulin, nourishing fluids, and/or therapeutic fluids such as fluids used in chemotherapy treatments. The disclosed connectors can also be used to interconnect various other components of fluid transfer systems.

Figure 13A:
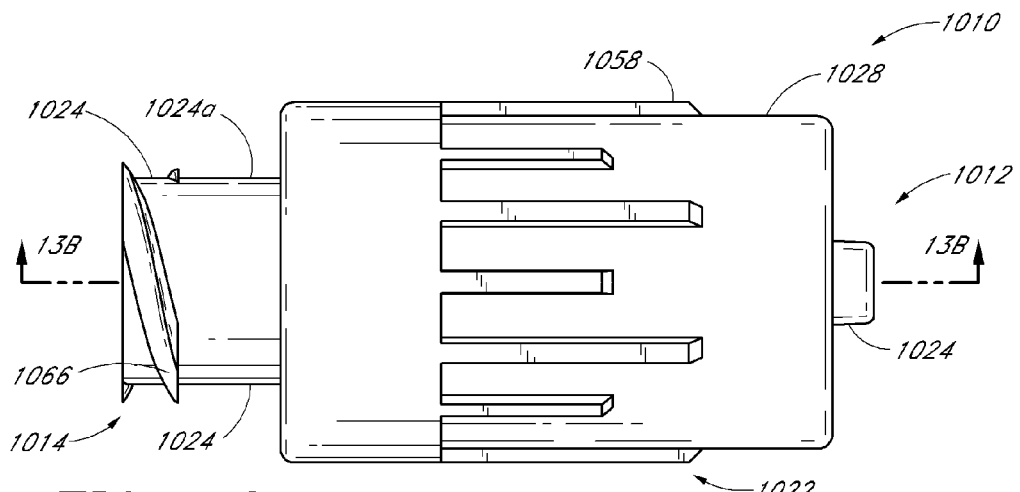
FIG. 13A is a side view of the outside of the embodiment of the luer connector shown in FIG. 12A.
Figure 13B:
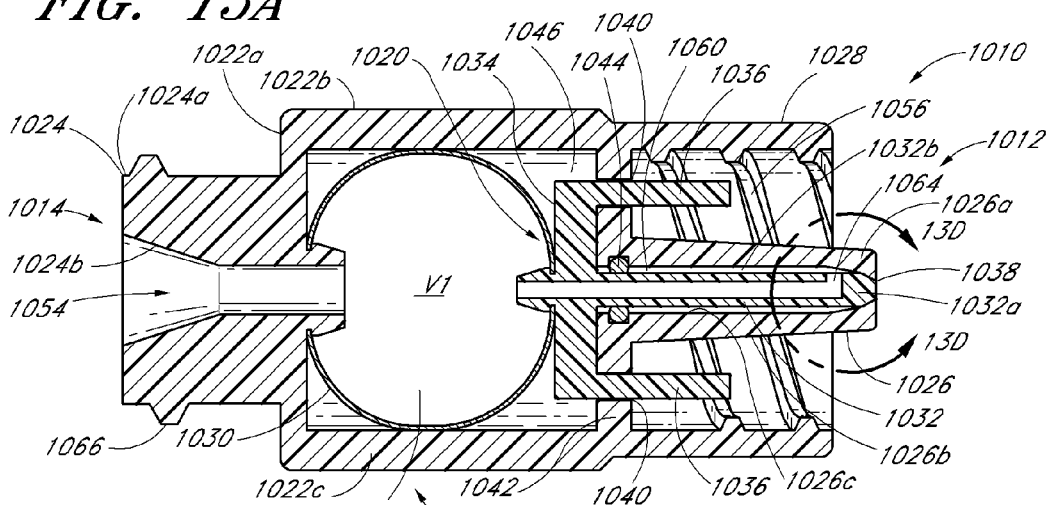
FIG. 13B is a cross-sectional view of the embodiment of the luer connector shown in FIG. 12A in a closed position.
Figure 13C:
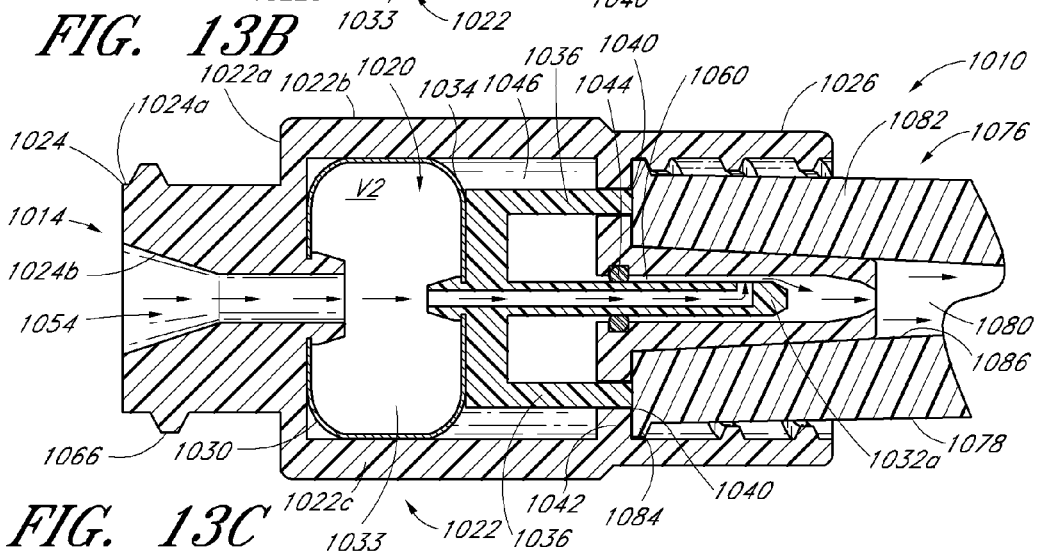
FIG. 13C is a cross-sectional view of the embodiment of the luer connector shown in FIG. 12A in an open position.
Figure 13:
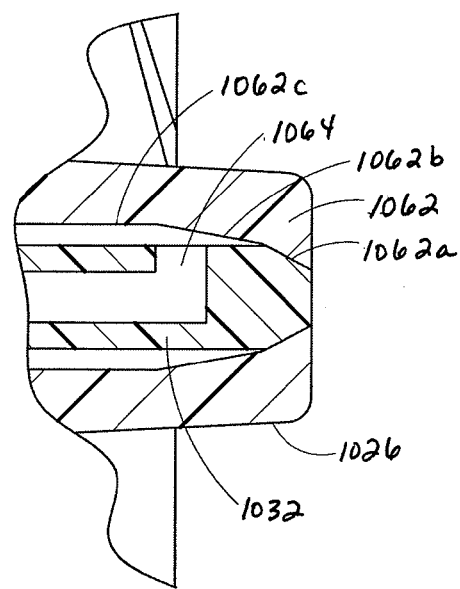
FIG. 13D is an enlarged section view of a portion of the embodiment of the luer connector shown in FIG. 13C, defined by the curve 13D-13D in FIG. 13B.
FIG. 13E is a cross-sectional view of another embodiment of a luer connector in a closed position.
FIG. 13F is a cross-sectional view of the embodiment of the luer connector shown in FIG. 13E in an open position.
FIG. 13G is a cross-sectional view of another embodiment of a luer connector in a closed position.
FIG. 13H is a cross-sectional view of the embodiment of the luer connector shown in FIG. 13G in an open position.
FIG. 13I is a cross-sectional view of another embodiment of a luer connector in a closed position.
FIG. 13J is a cross-sectional view of the embodiment of the luer connector shown in FIG. 13I in an open position.

Referring now to FIGS. 13A-13C, an embodiment of the closeable male luer 1010 of FIGS. 12A-12B is illustrated in greater detail. FIG. 13A is a side view of the outside of the luer connector 1010. FIG. 13B is a cross-sectional view of the luer connector 1010 in a closed position so that fluid is generally prevented from flowing through the luer connector 1010.

When the luer connector 1010 is in the closed position, fluid can be significantly prevented by the valve member 1020 from flowing through the luer connector 1010. In general, the valve member 1020 can be configured to prevent fluid under system pressures from flowing through the connector 1020. FIG. 13B is a cross-sectional view of the luer connector 1010, showing the valve member 1020 in an open position. In the open position, the valve member 1020 can be positioned so as to not significantly impede the flow of fluid through the luer connector 1010.

As illustrated in FIG. 13A, some embodiments of the assembled luer connector 1010 can comprise a housing 1022, a port 1024 positioned near the second end 1014 of the luer connector 1010, a luer tip 1026 positioned near the first end 1012 of the luer connector 1010, a shroud 1028 surrounding at least a portion of the luer tip 1026, a diaphragm 1030 supported within the housing 1022, and the valve member 1020 mentioned above also supported within the housing 1022. In some embodiments, the diaphragm 1030 can be formed from a generally fluid impervious, suitably resilient material and may be separately or integrally formed with the valve member 1020. The diaphragm 1030 can generally define an internal cavity 1033.

In the illustrated embodiment, the valve member 1020 can comprise a tube 1032 projecting from a valve base 1034 toward the first end 1012 of the connector 1010, and one or more valve arms or struts 1036 can also project from and be supported by the valve base 1034. In some embodiments, in an assembled configuration, the valve struts 1036 can be positioned so as to be adjacent to the tip 1026 along the sides of the tip 1026. When the luer connector 1010 is in the closed position, the outer surface of at least the distal portion 1032a of the valve tube 1032 can be sealingly closed against the inner surface of at least the distal portion 1026a of the luer tip 1026 such that fluid is generally prevented from flowing through the opening 1038 formed in the distal end 1026a of the luer tip 1026.

Generally, luer tip 1026 corresponds to ANSI standards for medical connectors to facilitate use with various standard medical implements. In some embodiments, the diameters of the opening 1038 in the distal tip portion 1026a of the luer tip 1026 can be in the ranges of approximately 0.4 mm to approximately 1.8 mm, approximately 0.5 mm to approximately 1.5 mm, and approximately 0.5 to approximately 1.0 mm. Other diameters, either inside or outside the listed ranges can also be used. Additionally, as described above and relating to FIG. 12A and higher, the second end of the valve member 1020 can be sized appropriately to occupy the space in the opening 1038 of the distal end portion 1026a of the luer tip 1026.

In the illustrated embodiment, the tube 1032 can be slidable so as to translate axially within the luer tip 1026. Further, the valve struts 1036 can be supported in a cantilevered disposition by the valve base 1034 and can be configured so as to slide within the openings 1040 formed through the internal wall 1042 of the housing 1022. The number of openings 1040 through the internal wall 1042 can be equal to the number of the valve struts 1036 supported by the valve base 1034. An annular sealing member 1044 can be positioned between the outside surface of the valve tube 1032 and the inside surface of the luer tip 1026 so as to prevent any fluid from flowing into the chamber 1046. In the illustrated embodiment, the chamber 1046 is the space outside the internal cavity 1033 generally defined by diaphragm 1030 that is generally confined by the end wall 1022a of the housing 1022, the sidewall 1022b (which can be cylindrically shaped) of the housing 1022, and the internal wall 1042 formed on the housing 1022.

In the illustrated embodiment, the diaphragm 1030 can be supported near the second end 1014 of the luer connector 1010 by the end wall 1022a of the housing 1022, laterally by the sidewall 1022b (which can be cylindrically shaped) of the housing 1022, and by the valve member 1020. In the illustrated embodiment, the diaphragm 1030 can comprise a pair of generally opposing openings 1048a, 1048b, through which fluid can pass. The first opening 1048a formed in the diaphragm 1030 can be sealably supported by a protrusion 1050 formed on the end wall 1022a of the housing 1022. The second opening 1048b formed in the diaphragm 1030 can be sealably supported by a protrusion 1052 formed on the valve base 1034. The first and second openings 1048a, 1048b can be supported by the protrusions 1050, 1052 so that fluid can be generally prevented from leaking into the chamber 1046.

In some embodiments, the diaphragm 1030 can be resilient and biased toward an expanded position, as illustrated in FIG. 13B, so as to exert a force on the valve member 1020 that biases the valve member 1020 toward the closed position. Further, the diaphragm 1030 can be configured so that the volume of the cavity 1033 within the diaphragm 1030 when the valve member 1020 is in the closed position (which is represented by V1 in FIG. 13B) can be greater than the volume of the cavity 1033 within the diaphragm 1030 when the valve member 1020 is in the open position (which is represented by V2 in FIG. 13C). Thus, the volume of the cavity 1033 within the diaphragm 1030 can decrease when the valve member 1020 moves from the closed position to the open position and can increase when the valve member 1020 moves from the open position to the closed position. By increasing the volume of the cavity 1033 within the diaphragm 1030 as the valve member 1020 moves to the closed position, the diaphragm 1030 can create a force of suction that reduces the amount of fluid or medicament that can flow through or drip out of the opening 1038 as the valve member 1020 is in the process of closing, by drawing such fluid back towards the diaphragm 1030.

In some embodiments, the valve 1020, the valve base 1034, the valve struts 1036, and the protrusion 1052 can be integrally formed. In some embodiments, any of the features of the valve member 1020, including the valve tube 1032, the valve base 1034, the valve struts 1036, and the protrusion 1052, can be separately formed and adhered or otherwise joined together in subsequent manufacturing steps. In some embodiments, the end wall 1022a can be formed integrally with at least the sidewalls 1022b of the housing 1022. In some embodiments, the end wall 1022a can be formed separately as compared to at least the sidewalls 1022b and joined or adhered to the housing 1022 in a subsequent manufacturing step, preferably after other components such as the valve member 1020, the diaphragm 1030, and the seals are properly positioned within the housing.

In some embodiments, the housing 1022 can generally be a tube-like structure with a passageway 1054 that can extend from the second end 1014 of the connector 1010 and preferably through the axial center of the luer connector 1010. As a result, in some embodiments, when the luer connector 1010 is in the open state or position, as illustrated in FIG. 13C, the passageway 1054 can permit fluid to flow from the second end 1014 through the port 1024, the diaphragm 1030, the tube 1032, and out through the opening 1038 in the luer tip 1026 positioned at the first end 1012 of the luer connector 1010. Near the second end 1014 of the luer connector 1010, the port 1024 and the corresponding section of the fluid passageway 1054 can be sized and configured so as to accommodate a section of standard-diameter medical tubing inserted therein.

In some embodiments, the port 1024 is configured to accept a standard male luer corresponding to ANSI standards for medical valves.

In some embodiments, the length of the housing 1022 (or any housing disclosed in FIGS. 12A-19D and the associated written disclosure) from the second end 1014 to the distal end of the luer tip 1026 can be approximately 0.75 inch. However, the housing 1022 can have many other sizes. In some embodiments, the length of the housing 1022 (or any housing disclosed in FIGS. 12A-19D and the associated written disclosure) from the second end 1014 to the distal end of the luer tip 1026 can be from approximately 0.5 inch to approximately 0.75 inch, or from approximately 0.75 inch to approximately 1.0 inch, or from approximately 1.0 inch to approximately 1.25 inches or more, or from or to any value within these ranges. Thus, the housing 1022 can be less than or equal to approximately 1.50 inches from the second end 1014 to the distal end of the luer tip 1026 so that the weight and bulk of the connector can be minimized. However, the housing 1022 can have any suitable length for a particular application.

The shroud 1028 can have inner threads 1056 on an interior wall that help securely attach the connector 1010 in a removable fashion to another medical implement. In other embodiments, the shroud 1028 can include other structures or materials for providing a releasable connection, including quick-release mechanisms and other means. As illustrated, the housing 1022 and shroud 1028 can define a plurality of protrusions 1058 or other suitable features on an outer surface to assist the user in firmly grasping and twisting the shroud 1028 and the housing 1022 with the user's fingers so as to prevent the luer connector 1010 from slipping within the user's grasp when the luer connector 1010 is twisted. In other embodiments (not illustrated) the housing 1022 or shroud 1028 may alternatively or additionally define depressions that have upwardly tapering sidewalls that provide additional support to help prevent the fingers from sliding off the connector 1010, or any other features or materials that substantially prevent the fingers from sliding relative to the connector 1010. The protrusions 1058 may extend around substantially the entire outer surface of the housing 1020 or shroud 1028 so that the user's fingers, when positioned on opposite sides of the connector 1010, will likely encounter a depression, regardless of the orientation of the connector 1010, during use.

With reference to FIGS. 13A-13C, the tip 1026 can have a tapered external wall. The diameter of the tip 1026 can become gradually smaller from the valve base 1034 towards the distal end portion 1026a of the tip 1026. As described above, the tip 1026 can define an opening 1038 positioned at the distal end portion 1026a of the luer tip 1026. At the base of the luer tip 1026, which can be the internal wall 1042, an interior space 1060 (see FIG. 13B) communicates with the fluid passageway 1054 of the luer connector 1010 and with the opening 1038 so as to provide a fluid flow path through the entire luer connector 1010. In some embodiments, the term fluid passageway can refer to the entire fluid pathway through the luer connector. With regard to any of the luer connectors disclosed in FIGS. 12A-19D and the associated written disclosure, the dimensions of the luer tip and the end cap (i.e., the male and female ends) can be made to comply with applicable standards and/or regulations, such as the ANSI standards.

FIG. 13D is an enlarged section view of a portion of the luer connector 1010, defined by the curve 13D-13D in FIG. 13B. As shown in FIG. 13D, the interior wall of the luer tip 1026 can include a constricted portion 1062 that extends radially inwardly toward the axis of the fluid passageway 1054 surrounded by the luer tip 1026, making the fluid passageway 1054 narrower at the distal end portion 1026a of the luer tip 1026 than in the region adjacent to the constricted portion 1062. In the illustrated embodiment, the constricted portion 1062 can define a generally cylindrically shaped surface 1062a and a generally sloped or tapered surface 1062b. In some embodiments, as in the illustrated embodiment, the constricted portion 1062 can further define a second sloped or tapered surface 1062c that can be configured to match a similarly sloped or tapered surface on the distal end portion 1032a of the tube 1032.

As illustrated in FIG. 13D, in some embodiments, the distal end portion 1032a of the tube 1032 can be sized and configured so as to complement the size and shape of the constricted portion 1062 of the luer tip 1026 so as to define a sealable closing mechanism. The closing mechanism can be adapted to close the fluid passage extending through the closeable male luer 1010 from fluid communication with the external environment, such as when the male luer 1010 is not engaged with a female connector. In particular, in some embodiments the distal end portion 1032a of the tube 1032 can be sized and configured so as to complement the generally cylindrically shaped, sloped surface 1062a. In some embodiments, the tube 1032 can be further configured to complement the generally sloped surface 1062b and the second sloped surface 1062c of the constricted portion 1062. The inner diameter of the constricted portion 1062 can become narrower so as to generally block and/or impede fluid flow through the connector 1010 when the distal end portion 1032a of the tube 1032 is abutted against it. Thus, as the distal end portion 1032a of the tube 1032 abuts against the inside surface of the luer tip 1026, a closure can be formed at or near the first end 1012 of the male luer 1010. Further, the distal end portion 1032a of the tube 1032 can be made from, or covered by, a different material than is used to form the tube 1032. For example, in some embodiments, the distal end portion 1032a can be covered with a softer, more malleable or deformable material as compared to the material used to form the tube 1032 so as to provide better sealing properties between the distal end portion 1032a of the tube 1032 and the luer tip 1026.

Any of the luer connectors disclosed in FIGS. 12A-19D and the associated written disclosure may be configured to comprise the features of the constricted portion 1062 described above. Finally, the opening 1064 in the distal end portion that can be in fluid communication with the passageway 1054 can be of any suitable size or shape to improve manufacturability or to most effectively channel the fluid through the luer connector 1010 when the valve member 1020 is in the open position. For example, the holes 1052 can be formed with a tear-drop shape (e.g., narrow on one end and wider on an opposite end), which may facilitate an injection molding process of manufacture. Further, in some embodiments, the valve member 1020 can be constructed without a fluid path and function as a blocking plunger for fluid flowing around the valve member 1020 rather than as a means for conveying fluid between the first and second ends of the luer connector 1010.

In some embodiments, the housing 1022 can be formed in two halves that each define a planar joining surface, such as, but not limited to, a surface 1022c that defines the planar section surface in FIG. 13B. In this configuration, the end portion 1022a of the housing 1022 can be formed in a separate step as compared to the rest of the housing, and subsequently adhered to or otherwise joined to the housing after the two halves described above are adhered or otherwise joined together.

The housing 1022 of the illustrated embodiment, or the housing of any embodiment disclosed in FIGS. 12A-19D and the associated written disclosure, can be constructed from any of a number of different materials or combination of materials. In some embodiments, the housing 1022 or any housing disclosed in FIGS. 12A-19D and the associated written disclosure, can be constructed from a relatively rigid material, such as polycarbonate or other polymeric material. The housing 1022 and/or valve member 1020 of this embodiment, or the housing and/or the valve member of any embodiment disclosed in FIGS. 12A-19D and the associated written disclosure, or any of the components of this or any other embodiment disclosed in FIGS. 12A-19D and the associated written disclosure, can also be constructed of a medical grade, hydrophobic material, such as Bayer Makrolon, or any other suitable material.

In some embodiments, the diaphragm 1030 can comprise a resilient material such that the diaphragm 1030 can be compressed into an open position and resiliently return to its original closed position, as described above and relating to FIG. 12A and higher. In some embodiments, the diaphragm 1030 may be formed from a non-rubber silicone or other suitable material depending at least on the medicament or fluid to be passed through the luer connector 1010. Further, in some embodiments, the diaphragm 1030 can be generally fluid impermeable so as to generally prevent any fluid from permeating therethrough into the chamber 1046. The valve member 1020 or any valve member disclosed in FIGS. 12A-19D and the associated written disclosure, like the housing 1022, may be constructed from a number of different materials or combinations of different materials, including the material that is used to form the housing 1022. Examples of such materials include polycarbonate or other polymeric materials. In certain applications, for example, semi-rigid or even more flexible materials may be desirable for use in the valve member 1020, and more particularly for the distal end portion 1032a of the tube 1032.

The length of the valve member 1020 can be shorter than the length of the housing 1022. Any of the valve assemblies disclosed in FIGS. 12A-19D and the associated written disclosure, including but not limited to the valve member 1020, may be manufactured through injection molding. Finally, although the valve member 1020 of the illustrated embodiment can be configured as shown in FIGS. 13B-13C, many other configurations are possible.

In some embodiments, as in the embodiments illustrated in FIGS. 13A-13C, one or more protrusions or raised tabs 1066 (such as, but not limited to, threads) can be formed on an exterior surface 1024a of the port 1024 to facilitate removably attaching a medical implement (not shown) with the second end 1014 of the valve member 1020. Accordingly, in some embodiments, the exterior surface 1024a can be cylindrical except for the protrusions, raised tabs, or other features formed thereon. In some embodiments, the interior surface 1024b of the port 1024 can be conically shaped, such that the diameter of the interior surface 1024b can be greatest at the portion of the interior surface 1024b adjacent to the second end 1014 of the luer connector 1010. The internal taper of the interior surface 1024b can compliment and closely fit with the taper of a typical male luer. Such an internal taper can conform to ANSI standards and/or regulations, such as the standard for medical syringes.

Similarly, the outside surface 1026b of the luer tip 1026 can also be tapered to conform to ANSI standards and/or regulations, such as the standard for medical syringes. In some embodiments, the inside surface 1026c of the luer tip 1026 and the outside surface 1032b of the tube 1032 can either be straight or can also be tapered. Tapering the inside surface 1026c of the luer tip 1026 and the outside surface 1032b of the tube 1032 can help minimize the amount of fluid that flows into and is trapped in the interior space 1060 between the tube 1032 in the luer tip 1026, since the distance between the tapered inside surface 1026c of the luer tip 1026 and the outside surface 1032b of the tube 1032 would be reduced as the tube 1032 moves toward a closed position. In these configurations, the sealing member 1044 can be configured so as to provide an effective seal between the tube 1032 and the luer tip 1026 even when the distance of the gap therebetween increases.

As shown in FIGS. 13A-13D, the closeable luer connector 1010 can have a female mating end at the second end 1014 of the luer connector 1010 and a male luer mating end at the first end 1012 of the luer connector 1010. The closeable female connector 1021 of FIG. 12B (referenced above), as well as other standard female connectors with similar external structure, can also have both female and male ends. In many embodiments, such female connectors can utilize seals or other fluid barriers to impede the flow of fluid on the female end but do not typically do so on the male end. In many of the embodiments of the closeable male luer connectors illustrated and disclosed in FIGS. 12A-19D and the associated written disclosure there may be no seal or other fluid barrier shown on the female end. However, the female end of any of the closeable male luer connectors disclosed in FIGS. 12A-19D and the associated written disclosure can be configured to include a closeable female end. For example, the structure for selective fluid-impedance with the female connector 1021, or any of the other standard female connectors, could be included within the female end of any of the closeable male luer connectors disclosed in FIGS. 12A-19D and the associated written disclosure to provide a connector that selectively seals or impedes fluid flow on both ends. In some embodiments of this type with closeable female and male ends, it can be advantageous for a resilient seal element to be positioned at or near the female opening, as shown in U.S. Pat. No. 5,685,866 entitled Medical Valve and Method of Use, filed on Nov. 4, 1994, which disclosure is hereby incorporated by reference in its entirety. By positioning the seal element in this manner, it is possible to cleanse the female opening prior to use with antiseptic with a wiping motion to avoid a harmful accumulation of debris, bacteria, antiseptic, or other unwanted substances on the seal element and/or in the region between the seal element and the housing of the connector adjacent to the seal element.

Figure 14:
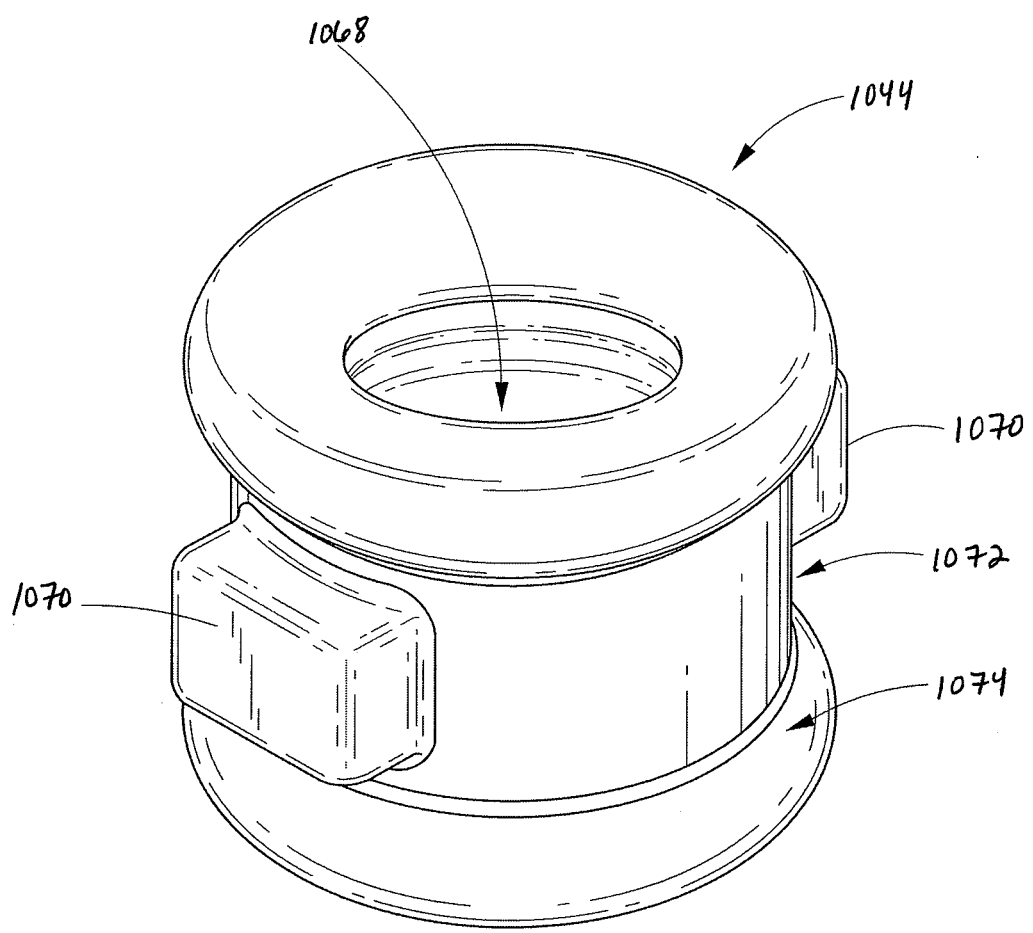
FIG. 14 is an enlarged perspective view of an embodiment of a sealing member.

With reference again to FIGS. 13B and 13C, the sealing member 1044 will now be described in greater detail. In some embodiments, the sealing member 1044 can define an annular cross-section, as illustrated in FIGS. 13B and 13C. In addition, in some embodiments, the luer connector 1010 can be configured such that an alternative sealing member 1044' can be used in place of the annular sealing member described above. FIG. 14 is an enlarged perspective view of an alternative sealing member 1044'. With reference to FIG. 14, the sealing member 1044' can be substantially cylindrical and can have a bore 1068 extending axially through the center thereof. In some embodiments, the sealing member 1044' can further comprise a pair of generally rectangular protrusions 1070 extending from the sidewalls of the cylindrical portion at diametrically opposed positions. In other embodiments, the protrusions 1070 can have different shapes and/or positions, and can assist with positioning and/or aligning the sealing member 1044' in the desired position. In some embodiments, the sealing member 1044' can also have a generally smaller-diameter middle portion 1072 surrounded by two rings 1074 at either end with larger diameters. The sealing member 1044 or 1044' can be constructed from a number of different materials. In some embodiments, the sealing member 1044 or 1044' can be made from a silicon-based deformable material. Silicon-based deformable materials are among those that can form fluid-tight closures with plastics and other rigid polymeric materials.

Thus, as shown in FIG. 13B, the housing 1022, the valve member 1020, and the sealing member 1044 are in an assembled configuration, in which the closing mechanism forms a closing engagement between the distal portion 1032*a* of the tube 1032 and the interior of the luer tip 1026. In addition, the sealing member 1044 can be in closing engagement between the valve member 1020 and the interior surface 1026*c* of the luer tip 1026. In this configuration, in the closed position, fluid flowing through the passageway 1054 may be able to flow through the opening 1064 adjacent to the distal portion 1032*a* of the tube 1032. In this position, the opening 1064 can communicate with the interior space 1060, but not with the external environment. As discussed above, it may be advantageous to configure the external surface of tube 1032 and the internal surface of 1026 to minimize the space 1060.

FIG. 13C is a cross-sectional view of the luer connector 1010 in an open position, so that fluid can be generally permitted to flow through the luer connector 1010. The flow of fluid through the luer connector 1010 is represented by arrows in FIG. 13C. The housing 1022, the valve member 1020, and the sealing member 1044 are illustrated in an assembled configuration. As shown, the valve member 1020 has been moved to the open position by the insertion of the female connector 1076. Thus, FIG. 13C illustrates a cross-section of an embodiment of the luer connector 1010 wherein the valve member 1020 has been caused to be opened by the insertion of an exemplifying female connector 1076. With reference to the embodiment illustrated in FIG. 13C, the structure of an exemplifying female connector 1076 will now be discussed in further detail. The female connector 1076 can comprise an elongate body 1078 having a fluid passageway 1080 therethrough, and the female connector 1076 can have a tip 1082 near its distal end. In some embodiments, the tip 1082 of the female connector 1076 can have a radially extending surface 1084 disposed on its external surface. The female connector 1076 can have a fluid conduit within the female connector 1076. The fluid conduit is not included or required in all female connectors compatible with the connectors 1010 disclosed in FIGS. 12A-19D and the associated written disclosure. Along a proximal inner surface 1086 of the female connector 1076, the fluid passageway 1080 can be tapered such that the diameter of the fluid passageway 1080 decreases in the distal direction.

As shown in FIG. 13B and discussed above, the struts 1036 of the valve member 1020 can extend through openings 1040 in the internal wall 1042 of the housing 1022 such that, in the closed position, the ends of the struts 1036 extend past the internal wall 1042 toward the first end 1012 of the connector 1010. The struts 1036 can be configured to engage the proximal end 1084 of the female connector 1076 as the female connector 1076 advances into engagement with the closeable male luer 1010. To engage the male luer 1010 and female connector 1076, as is shown in FIG. 13C, the radially extending surface or surfaces 1084 of the female connector 1076 can be threaded into the inner threads 1056 of the male luer 1010. As shown in FIG. 13C, the two luers 1010, 1076 can be threadedly engaged with one another until the taper of the inner surface 1086 of the female luer connector 1076 lies adjacent the correspondingly tapered external surface 1026*b* of the tip 1026.

As the male luer connector 1010 and female connector 1076 move towards each other into threaded engagement, the proximal end 1084 of the tip of the female connector 1076 can contact the struts 1036 of the valve member 1020. As the male luer connector 1010 and female connector 1076 move further into threaded engagement, the struts 1036, and thereby the valve member 1020, can be moved toward the second end 1014 of the male connector 1010 by the female connector 1076. Thus, the distal end portion 1032*a* can move away from the interior distal end portion 1026*a* of the tip 1026 in the direction of the second end 1014 of the male connector 1010 as the male luer connector 1010 and female connector 1076 move further into threaded engagement. As the tip 1026 and the tube 1032 move apart from one another, a space or gap can form between the tube 1032 and the luer tip 1026, permitting fluid to pass through the opening 1038 into the fluid passageway 1080 of the female connector 1076, or vice versa.

When used with certain alternative embodiments of the female connector 1076, an internal fluid conduit of the female connector 1076 may contact the distal end portion 1032*a* of the tube 1032 before the housing of the female connector 1076 contacts the struts 1036, thereby opening the male connector 1010. In some embodiments, the closure may remain intact until the inner surface 1086 of the tip of the female connector 1076 has formed a closing engagement with the outer surface of the tip 1026 of the male luer 1010, substantially limiting fluid within the passageway 1054 of the male luer 1010 from being exposed to the external environment.

In some embodiments, as the valve member 1020 moves relative to the housing 1022, the resilient diaphragm 1030 can compress, causing the diaphragm 1030 to exert a biasing force on the valve member 1020 toward the closed position or causing the diaphragm 1030 to increase the biasing force exerted on the valve member 1020. The biasing force from the diaphragm 1030 can be resisted by the radially extending surface 1084 of the female connector 1076 contacting the inner threads 1056 of the housing 1022. However, when the female connector 1076 is withdrawn from the male luer 1010, the diaphragm 1030 can return the sealing portion of the valve member 1020 to the closed position within the luer tip 1026.

Despite the relative movement between the housing 1022 and the valve member 1020, the sealing member 1044 can maintain a fluid barrier between the outer surface of the tube 1032 and the inner surface of the luer tip 1026. In some embodiments, where the sealing member 1044 comprises the generally rectangular protrusions 1070, the position of the sealing member 1044 can be maintained by the protrusions 1070. In some embodiments, the sealing member 1044 can be positioned by adhering the outer surface of the protrusions 1070 to an inner surface of the luer tip 1026. In some embodiments, the sealing member 1044 can be positioned by adhering the outer surface of the seal 1044 to an inner surface of the luer tip 1026 or to an outer surface of the valve tube 1032. Other suitable means of fixing the position of the sealing member 1044 can also be used.

As shown in FIG. 13C, in the opened configuration, the fluid passageway 1080 of the female connector 1076 can communicate with the passageway 1054 of the valve member 1020 so as to allow fluid to flow through the passageway 1054 and the fluid passageway 1080 of the female connector 1076 in either direction. Fluid can thereby flow from tubing (not shown) or another connector or conduit that can be attached to the luer connector 1010, into the passageway 1054 of the housing 1022, through the opening or openings 1064 into the interior space 1060 within the luer tip 1026, out from the interior space 1060 within the luer tip 1026 through the opening 1038 at the distal end portion 1026*a* of the luer tip 1026 and into the fluid passageway 1080 of the female connector 1076, and vice versa. A fluid-tight closure can also be formed between corresponding tapers of the outside surface of the tip 1026 and the inner surface 1086 of the female connector 1076.

As discussed above, as the valve member 1020 opens, it can cause the diaphragm 1030 to be compressed and the volume of fluid that can be contained within the cavity 1033 of the diaphragm 1030 can accordingly decrease. In some embodiments, while the diaphragm 1030 is being compressed (which can decrease the volume of fluid in the diaphragm 1030), the fluid within the diaphragm 1030 can be subjected to an increased pressure due to the compression of the diaphragm 1030. With the female connector 1076 fully connected, the volume of the cavity 1033 in the diaphragm 1030 can be reduced to V2. V1 can be larger than V2, and in some embodiments, the difference in volume between V1 and V2 can generally correspond to the volume of residual fluid, such as a drip, that is expected to remain on the outside of the male luer upon disconnection from the female luer.

Conversely, in some embodiments, when the female connector 1076 is removed from the luer connector 1010, and the valve member 1020 can move back toward the closed position, thereby causing the volume within the cavity 1033 of the diaphragm 1030 to expand back to the closed position volume V1. The expansion of the interior volume of the diaphragm 1030 can cause a reduced pressure or suction to be generated within the diaphragm 1030. This reduced pressure or suction can cause the cavity 1033 to draw at least some of the fluid that is within the passageway 1060 within the luer tube 1026 or on the outside surface of the end of the tube 1032*a* back into the diaphragm 1030. The suction or draw-back is beneficial in that it can prevent fluid from dripping out of the opening 1038 as the female connector 1076 is being removed. In some embodiments, the luer connector 1010 may be used to control the flow of fluids or medicaments that are harmful or corrosive, such as by substantially preventing one or more drops from dripping out of the opening 1038 as the female connector 1076 is being removed.

Figure 13E:
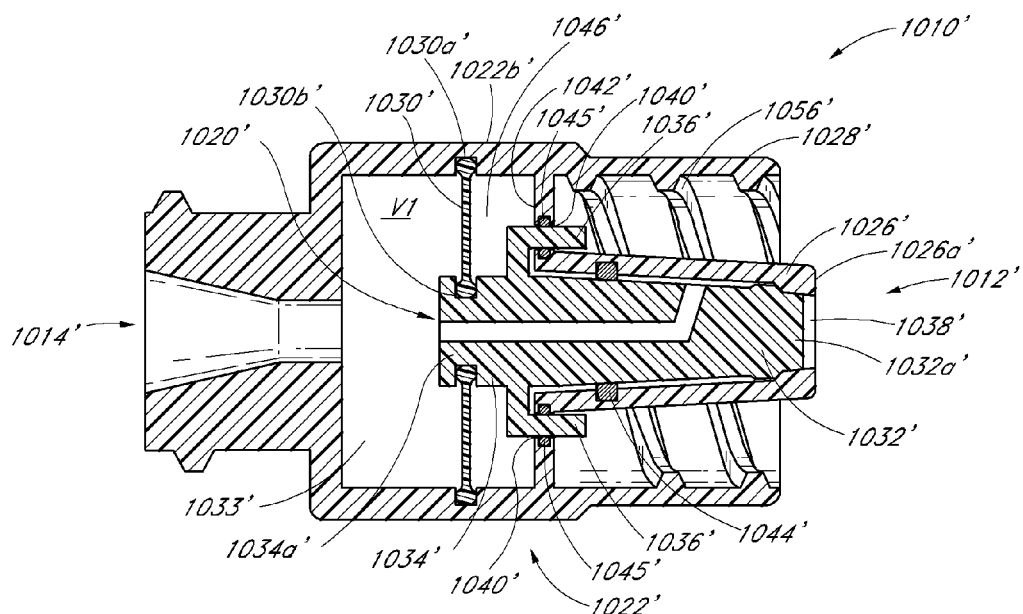
Figure 13F:
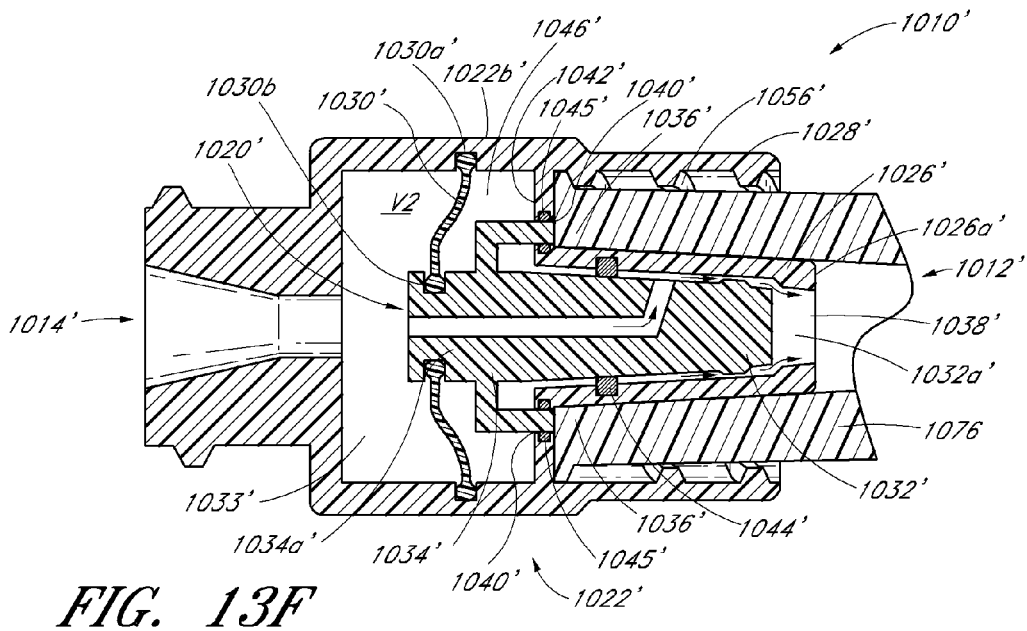

Referring now to FIGS. 13E-13F, other embodiments of the closeable luer connector 1010' will be described. In some embodiments, the luer connector 1010' may comprise any of the components, features, materials, sizes, geometries, details, or configurations of any of the other luer connectors disclosed in FIGS. 12A-19D and the associated written disclosure. FIG. 13E is a cross-sectional view of the luer connector 1010' in a closed position. As described above, when the valve member 1020' of the luer connector 1010' is in the closed position, fluid is generally prevented from flowing through the luer connector 1010'. FIG. 13F is a cross-sectional view of the embodiment of the luer connector 1010' taken through the longitudinal center of the luer connector 1010', showing the valve member 1020' in an open position due to the engagement of a female connector 1076 with the luer connector 1010'. The flow of fluid through the luer connector 1010' is represented by arrows in FIG. 13F. As described above, when the valve member 1020' of the luer connector 1010' is in the open position, fluid can be generally permitted to flow through the luer connector 1010'.

In some embodiments, the luer connector 1010' can be the same or similar to the luer connector 1010 described above, with certain differences as illustrated and/or described below. Accordingly, in some embodiments, the luer connector 1010' may operate in the same or similar manner as compared to the luer connector 1010 described above. In the illustrated embodiment, the valve member 1020' can comprise a tube 1032' projecting from a valve base 1034' toward the first end 1012' of the connector 1010', and one or more arms or struts 1036' supported by the valve base 1034' such that an axial force imparted on the valve struts 1036' is generally transferred directly to the valve base 1034'. As shown in FIG. 13E and discussed above, the struts 1036' of the valve member 1020' can extend through openings 1040' in the internal wall 1042' of the housing 1022' such that, in the closed position, the ends of the struts 1036' extend past the internal wall 1042' toward the first end 1012' of the connector 1010'. In the illustrated embodiment, an annular seal 1045' can seal each of the openings 1040' through which a valve strut 1036' passes.

The struts 1036' can be configured to engage the proximal end 1084 of the female connector 1076 as the female connector 1076 advances into engagement with the closeable male luer 1010'. To engage the male luer 1010' and female connector 1076, as is shown in FIG. 13F, the radially extending surface or surfaces 1084 of the female connector 1076 can be threaded into the inner threads 1056' of the male luer 1010'. In an assembled configuration, the valve struts 1036' can be positioned so as to be adjacent to the tip 1026'. In the illustrated embodiment, the tube 1032', the valve base 1034', and the valve struts 1036' can be integrally formed so as to be a unitary member. However, in some embodiments, the tube 1032', the valve base 1034', and the valve struts 1036' may be separately formed and bonded, fused, adhered, or otherwise attached together to form the valve member 1020' illustrated in FIGS. 13E and 13F. As with any of the valve struts described above and relating to FIG. 12A and higher, the valve struts 1036' can be suitably rigid and configured such that, when a female connector 1076 is threadingly engaged with the luer connector 1010', the struts 1036' can be axially depressed toward the diaphragm member 1030', causing the diaphragm 1030' to deflect toward the second end 1014' of the luer connector 1010', as illustrated in FIG. 13F.

In some embodiments, as in the illustrated embodiment, the diaphragm 1030' can be formed so as to define a pair of generally planar surfaces and so as to have an outside circular perimeter and an opening through the center thereof. In the illustrated embodiment, the outer portion 1030*a'* of the diaphragm 1030' (which can be generally spherical) can be sealably secured to the inside surface of the side wall 1022*b'* of the housing 1022'. In some embodiments, as in the illustrated embodiments, the housing 1022' may define an annular depression which supports or secures the outer portion 1030*a'* of the diaphragm 1030' so as to prevent the diaphragm 1030' from moving from its desired position. Similarly, in the illustrated embodiment, the inner portion 1030*b'* of the diaphragm 1030' can be sealably secured to the outside surface of the aft portion 1034*a'* of the valve base 1034'. In some embodiments, as in the illustrated embodiments, the aft portion 1034*a'* of the valve base 1034' may define an annular depression which is configured to support or secure the inner portion 1030*b'* of the diaphragm 1030' so as to prevent the diaphragm 1030' from moving from its desired position.

In some embodiments, as in the illustrated embodiment, the diaphragm 1030' can be resilient and biased toward its relaxed planar shape, as illustrated in FIG. 13E. The diaphragm 1030' can be positioned so as to exert a force on the valve member 1020' that biases the valve member 1020' toward the closed position. In particular, in the illustrated embodiment, the diaphragm 1030' can bias the tube member 1032' to sealably close against the inside surface of the luer tip 1026'. In some embodiments, the diaphragm 1030' can be positioned within the luer connector 1010' so that, when the valve member 1020' is in the closed position, the diaphragm 1030' is partially deflected from its relaxed state so as to increase the bias force that the diaphragm 1030' exerts on the valve member 1020'.

As shown in FIGS. 13E and 13F, the inner portion of the connector 1020' may be split into two portions, the inner cavity 1033' and the chamber 1046'. The diaphragm 1030' can be configured so that the volume within the cavity 1033' when the valve member 1020' is in the closed position (e.g. represented by V1 in FIG. 13E) is greater than volume within the cavity 1033' when the valve member 1020' is in the open position (e.g. represented by V2 in FIG. 13F). In this configuration, the volume of space within the cavity 1033' can increase when the valve member 1020' moves from the open position to the closed position, thereby creating a force of suction that can reduce the amount of fluid or medicament that can flow through or drip out of the opening 1038' as the valve member 1020' closes, by drawing such fluid back toward the cavity 1033'.

As described, in some embodiments, the valve member 1020' may be configured such that the valve struts 1036' can be directly attached to either the tube 1032' or the valve base 1034' so that an axial force imparted on the valve struts 1036' is also generally imparted on the tube 1032' or the valve base 1034'.

Figure 13G:
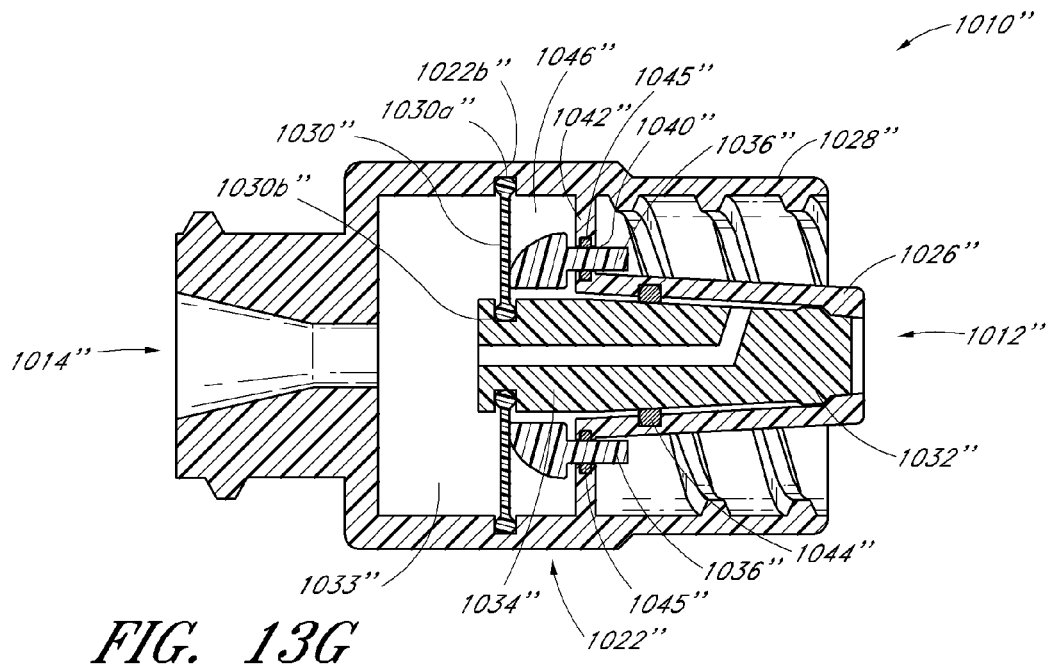
Figure 13H:
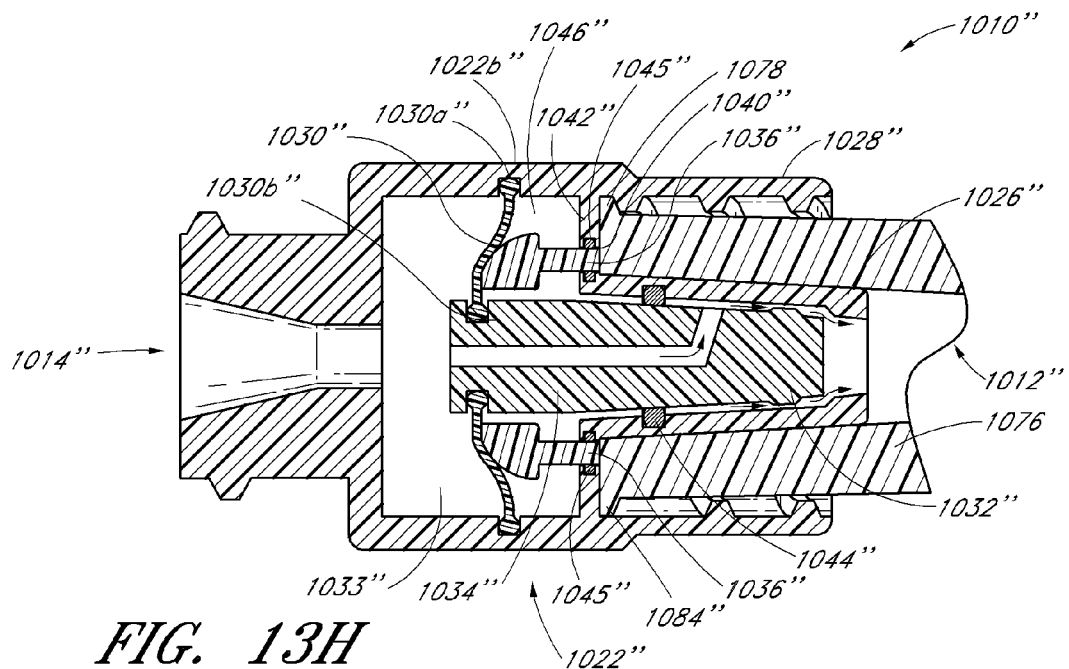

However, in other embodiments, as in the embodiment of the luer connector 1010" illustrated in FIGS. 13G and 13H, the tube 1032" and the valve base 1034" may be integrally formed while the struts 1036" can be separately formed and independently movable relative to the tube 1032" and the valve base 1034". In the embodiment illustrated in FIGS. 13G and 13H, the struts 1036" each can exert an axial force on at least a portion of the diaphragm 1030" when struts 1036" are displaced from the insertion of a female connector 1076 into the shroud 1028" as described above, thereby deflecting the diaphragm 1030". In this configuration, as the diaphragm 1030" is deflected, the valve member 1020" can be moved toward the open position because the diaphragm 1030" can be secured to the valve base 1034".

Figure 13I:
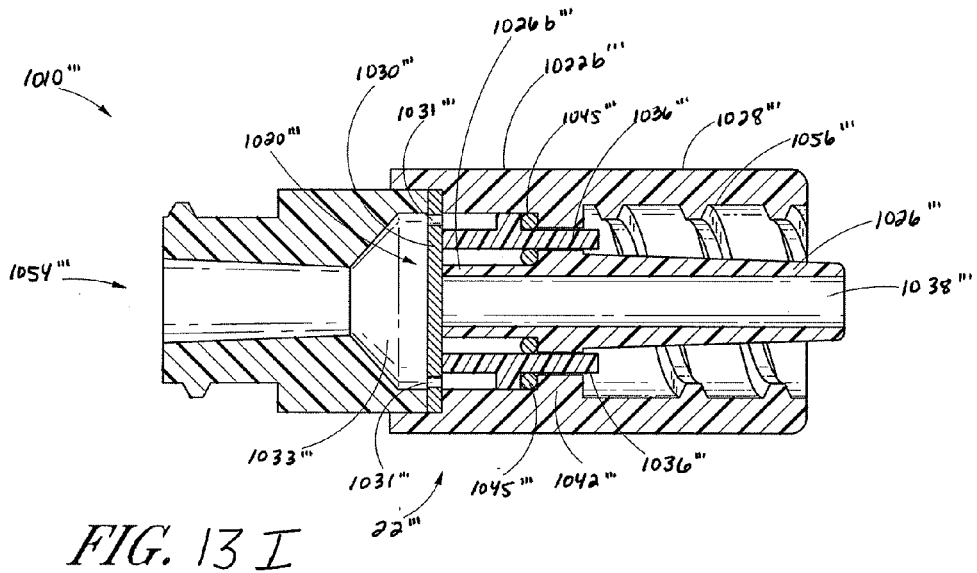
Figure 13J:
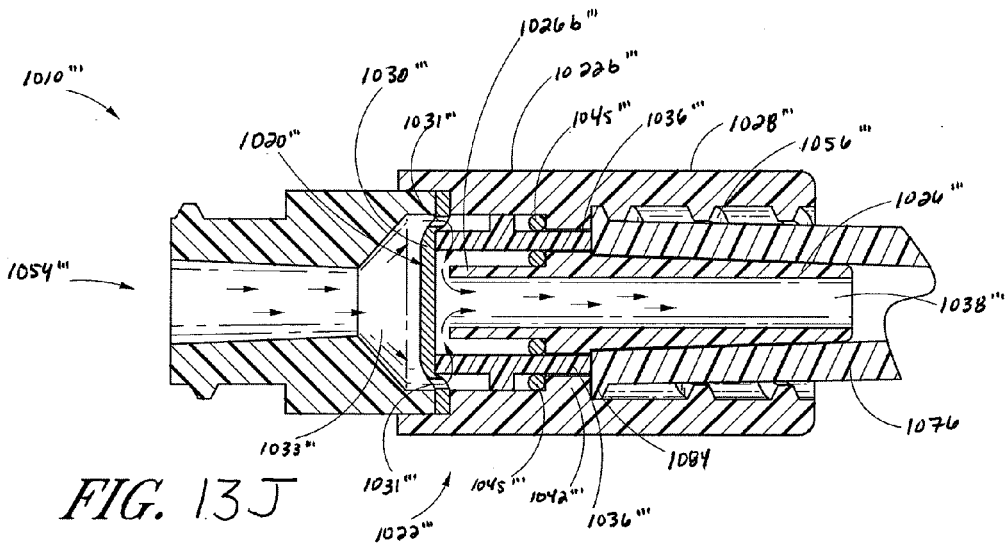

Referring now to FIGS. 13I-13J, some embodiments of the closeable luer connector 1010''' will be described. In some embodiments, the luer connector 1010''' may comprise any of the components, features, materials, sizes, geometries, details, or configurations of any of the other luer connectors disclosed in FIGS. 12A-19D and the associated written disclosure. FIG. 13I is a cross-sectional view of the luer connector 1010''' in a closed position. As described above, when the valve member 1020''' of the luer connector 1010''' is in a closed position, fluid is generally prevented from flowing through the luer connector 1010'''. FIG. 13J is a cross-sectional view of the embodiment of the luer connector 1010''' in an open position due to the engagement of a female connector 1076 with the luer connector. The flow of fluid through the luer connector 1010''' is represented by arrows in FIG. 13J. As described above, when the valve member 1020''' of the luer connector 1010''' is in the open position, fluid can be generally permitted to flow through the luer connector 1010'''.

In some embodiments, the luer connector 1010''' can be the same or similar to the luer connector 1010 described above, with certain differences in some versions as illustrated and/or described below. Accordingly, in some embodiments, the luer connector 1010''' may operate in the same or similar manner as compared to the luer connector 1010 described above. The valve member 1020''' can comprise one or more valve arms or struts 1036''' (two are shown), each of which can extend through an opening 1040''' in the internal wall 42''' of the housing 1022''' toward the first end 1012''' of the connector 1010'''. In the illustrated embodiment, two or more annular seals 1045''' can seal the openings 1040'''. The struts 1036''' can be configured to engage the proximal ends 1084 of the female connector 1076 as the female connector 1076 advances into engagement with the closeable male luer 1010'''. To engage the male luer 1010''' and female connector 1076, as is shown in FIG. 13J, the radially extending surface or surfaces 1084 of the female connector 1076 can be threaded into the inner threads 1056''' of the luer connector 1010'''.

The luer connector 1010''' can also comprise a resilient diaphragm 1030''' that, in some embodiments, can be generally planar with a circular perimeter. In some embodiments, as in the illustrated embodiment, the outer, peripheral portion of the diaphragm 1030''' may be supported by the housing 1022''', while the middle portion of the diaphragm 1030''' can be generally unsupported. In some embodiments, the diaphragm 1030''' can be positioned within the housing 1022''' so that, when the valve member 1020''' is in the closed position, the middle portion of the diaphragm 1030''' can sealably contact the aft or rear portion 1026b''' of the luer tip 1026'''. With reference to FIGS. 13I and 13J, the diaphragm 1030''' can comprise two or more openings 1031''' therethrough that allow fluid flowing through the passageway 1054''' to flow through the diaphragm 1030''', particularly when the valve member 1020''' is in an open position. In some embodiments, the openings 1031''' can be positioned on the diaphragm 1030''' at locations that can be radially outward from the position where the diaphragm 1030''' makes contact with the aft portion 1026b''' of the luer tip 1026'''. In this embodiment, the luer tip 1026''' can be stationary with regard to the housing 1022''', even when the luer connector 1010''' is changed from the open to the closed position. Therefore, in this configuration, when the valve member 1020''' is in the closed position, fluid flowing through the openings 1031''' in the diaphragm 1030''' can be prevented from flowing from the inner cavity 1033''' into the inside portion of the luer tip 1026''' by the seal that is created between the diaphragm 1030''' and the aft portion 1026b''' of the luer tip 1026'''.

The valve struts 1036''' can be suitably rigid and configured such that, when a female connector 176 is threadingly engaged with the luer connector 1010''', the struts 1036''' can be axially displaced toward the diaphragm 1030''', causing the diaphragm 1030''' to deflect toward the second end 1014''' of the luer connector 1010''', as illustrated in FIG. 13J. When the diaphragm 1030''' is displaced by the struts 1036''', fluid passing through the passageway 1054''' and the openings 1031''' can then flow between the resilient member 1030''' and the aft portion 1026b''' of the luer tip 1026''', and out through the opening 1038'''.

In some embodiments, as in the illustrated embodiment, the diaphragm 1030''' can be resilient and biased toward a planar shape, as illustrated in FIG. 13I, so as to exert a force against the aft portion 1026b''' of the luer tip 1026''' sufficient to bias the valve struts 1036''' to the closed position and to seal the diaphragm 1030''' against the aft portion 1026b''' of the luer tip 1026'''. In some embodiments, the diaphragm 1030''' can be positioned within the luer connector 1010''' so that, when the valve member 1020''' is in the closed position, the diaphragm 1030''' is partially deflected from its relaxed state so as to increase the spring force that the diaphragm 1030''' exerts on the valve struts 1036''' and the aft portion 1026b''' of the luer tip 1026'''.

Figure 15A:
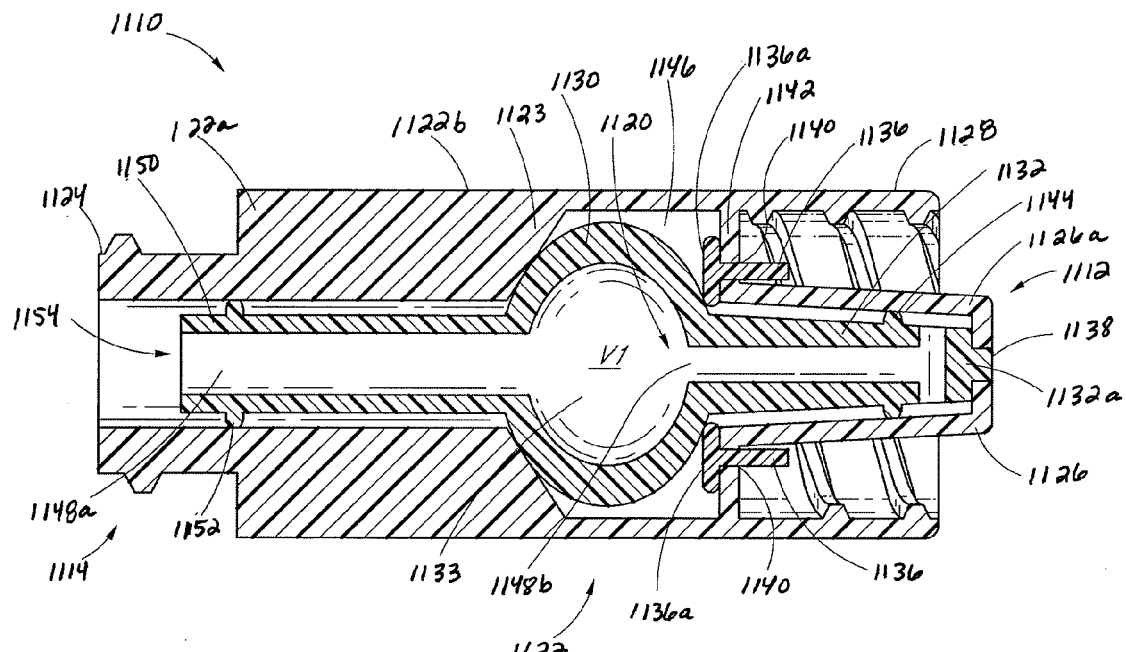
FIG. 15A is a cross-sectional view of another embodiment of a luer connector in a closed position.
Figure 15B:
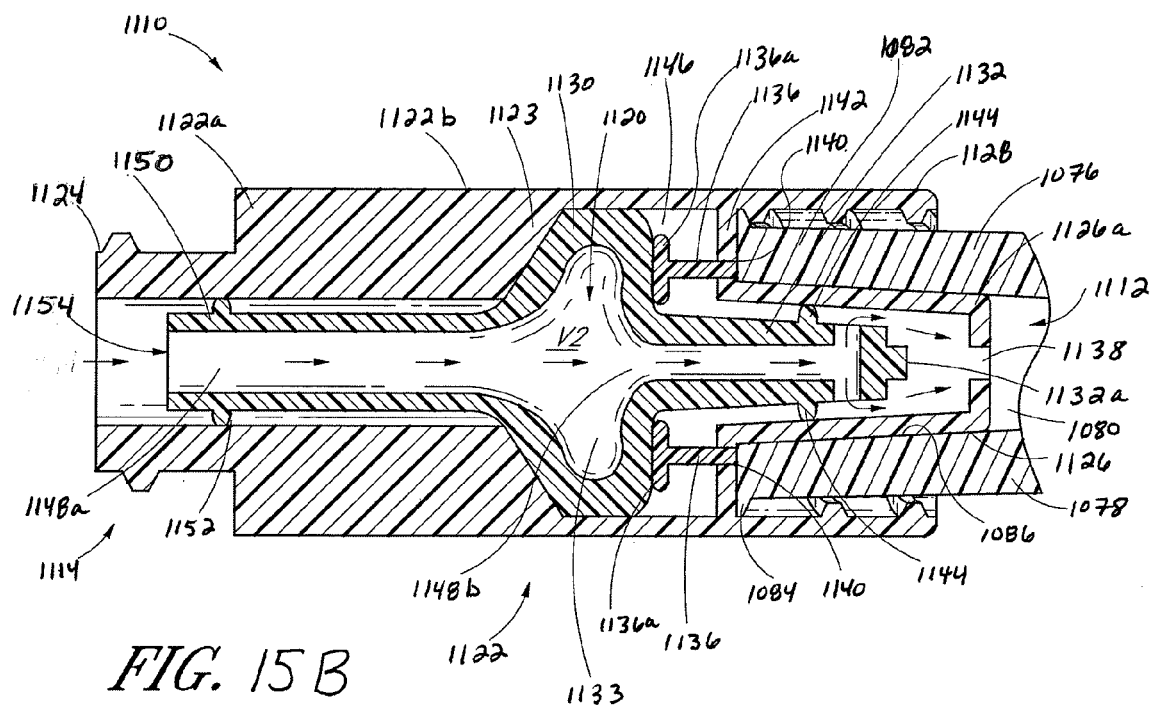
FIG. 15B is a cross-sectional view of the embodiment of the luer connector shown in FIG. 15A in an open position.

Referring now to FIGS. 15A-15B, some embodiments of the closeable luer connector 1110 will be described. In some embodiments, the luer connector 1110 may comprise any of the components, features, materials, sizes, geometries, details, or configurations of any of the other luer connectors disclosed in FIGS. 12A-19D and the associated written disclosure. FIG. 15A is a cross-sectional view of the luer connector 1110 in a closed position. As described above, when the valve member 1120 of the luer connector 1110 is in the closed position, fluid is generally prevented from flowing through the luer connector 1110. FIG. 15B is a cross-sectional view of the embodiment of the luer connector 1110 in an open position due to the engagement of a female connector 1076 with the luer connector. The flow of fluid through the luer connector 1110 is represented by arrows in FIG. 15B. As described above, when the valve member 1120 of the luer connector 1110 is in the open position, fluid can be generally permitted to flow through the luer connector 1110. As with any embodiment of the luer connector disclosed in FIGS. 12A-19D and the associated written disclosure, the seal or seals formed in the housing by the valve member is generally sufficient to resist fluid flow during normal operating conditions.

As illustrated in FIG. 15A, some embodiments of the assembled luer connector 1110 can comprise a housing 1122, a port 1124 positioned near the second end 1114 of the luer connector 1110, a luer tip 1126 positioned near the first end 1112 of the luer connector 1110, a shroud 1128 surrounding at least a portion of the luer tip 1126, a bladder member 1130, and the valve member 1120 mentioned above. The bladder member 1130 can be formed from a generally fluid impervious, suitable resilient material and may define an internal cavity 1133. In some embodiments, the bladder member 1130 may be ovular such that a cross section of the bladder member 1130 taken along a longitudinal axis of the connector 1110 is substantially ovular with the major axis of the bladder member 1130 being substantially perpendicular to the longitudinal axis of the connector 1110 when the connector 1110 is in the closed position. In some embodiments, the wall portion of the bladder member 1130 is concave toward the longitudinal axis of the connector so as to form a substantially ovular inner cavity. In some embodiments, the cavity is substantially circular. Other wall shapes may also be incorporated to enhance or adjust the rebound bias of the tube 1132 toward the first end 1112 of the connector 1110.

As illustrated, the bladder member 1130 and the valve member 1120 can be disposed within the housing 1122. The valve member 1120 can comprise a tube 1132 positioned within the inside surface of the luer tip 1126 and one or more valve struts 1136 (two are shown), that can be in engaging communication with the bladder member 1130. In some embodiments, in an assembled configuration, the valve struts 1136 can be positioned so as to be adjacent to the tip 1126 along the side of the tip 1126. In some embodiments, each of the valve struts 1136 can define a planar base portion 1136a on the end of the valve strut 1136 closest to the second end 1114 of the luer connector 1110.

In some embodiments, the valve member 1120 can comprise only one valve strut 1136, or two, three or more valve struts 1136. When the luer connector 1110 is in the closed position, the outer surface of the distal portion 1132a of the valve tube 1132 can be sealingly closed against the inner surface of the distal portion 1126a of the luer tip 1126 such that fluid can be generally prevented from flowing through the opening 1138 formed in the distal end 1126a of the luer tip 1126. In some embodiments, the base portion 1136a of each of the valve struts 1136 can be interconnected, so as to form in the annular ring around the tube 1132. In some embodiments, therefore, each of the valve struts 1136 can be interconnected by the base portion 1136a. In some embodiments, however, each of the valve struts 1136 can be independent so as to translate independently relative to the bladder member 1130 and relative to the other valve struts 1136, if any, that can be supported within the housing 1120. In some embodiments, where the valve struts 1136 are each independently movable, the base portion 1136a can therefore be disconnected from the base portion 1136a of the other valve struts 1136. In some embodiments, where the valve struts 1136 are each independently movable, the base portion 1136a can define a circular, square, triangular, ovular, arcuate, or other suitable shape.

As mentioned, in the illustrated embodiment, the tube 1132 can be slidably supported so as to translate axially within the luer tip 1126. Further, the valve struts 1136 can be configured so as to slide within the openings 1140 formed through the internal wall 1142 of the housing 1122. The number of openings 1140 through the internal wall 1142 can be equal to the number of the valve struts 1136 that can be supported within the housing 1122. An annular sealing member 1144 can be positioned between the outside surface of the valve tube 1132 and the inside surface of the luer tip 1126 so as to prevent any fluid from flowing into the chamber 1146 during normal use. In the illustrated embodiment, the chamber 1146 is the space that is generally confined by the end wall 1122a of the housing 1122, the sidewall 1122b (which can be cylindrically shaped) of the housing 1122, and the internal wall 1142 formed on the housing 1122. Chamber 1146 generally extends around the bladder member 1130 and is generally isolated from any fluid flowing through the connector 1110. The sealing member 1144 can comprise any of the materials, geometries, sizes, or other details of configurations of any other seal disclosed in FIGS. 12A-19D and the associated written disclosure. In some embodiments, the sealing member 1144 can be formed from the same material as the valve tube 1132 and can be formed integrally with the valve tube 1132. In some embodiments, the sealing member 1144 can be formed from a different material as compared to the valve tube 1132. In some embodiments, the sealing member 1144 can be formed separately from the valve tube 1132 and positioned at the desired axial location of either the valve tube 1132 or the inside surface of the luer tip 1126. Accordingly, in some embodiments, either the inside surface of the luer tip 1126 or the valve tube 1132 can comprise features such as channels or depressions to secure the sealing member 1144 in the desired location. In some embodiments, the end wall 1122a can be formed integrally with at least the sidewalls 1122b of the housing 1122. In some embodiments, the end wall 1122a can be formed separately as compared to at least the sidewalls 1122b and adhered or attached thereto in a subsequent manufacturing step.

In the illustrated embodiment, the bladder member 1130 can be supported on one end by the projection 1123 (which can be annular), laterally by the sidewalls 1122b of the housing 1122 (which can be cylindrically shaped), and at an other end by the base portions 1136a of the valve struts 1136. In some embodiments, as with other components, the projection 1123 can be omitted from the housing such that the bladder member is supported by the end portion 1122a of the housing 1122 instead of by the projection 1123. In the illustrated embodiment, the projection 1123 can be formed so as to effectively allow the length of the housing 1122 to be increased without increasing the volume of the bladder member 1130. It may be desired to increase the length of the housing 1122 to provide a longer gripping surface for the user or medical practitioner. Accordingly, in some of the embodiments, such as those described above wherein the housing 1122 does not comprise the projection 1123 or comprises a shorter projection 1123, the length of the housing 1122 may be shorter than as illustrated in FIG. 15A. In some embodiments, the ratio of the radial thickness of the projection 1123 to the sidewall 1122b can be in the range of approximately 2 to 1 to approximately 10 to 1. In some embodiments, the ratio is approximately 7 to 1.

In the illustrated embodiment, the bladder member 1130 can comprise a pair of opposing openings 1148*a*, 1148*b* through which fluid can pass. In some embodiments, the bladder member 1130 can be resilient and biased toward an expanded position, as illustrated in FIG. 15A, so as to exert a force on the valve member 1120 that biases the valve member 1120 toward the closed position. In particular, in the illustrated embodiment, the bladder member 130 can bias the tube member 1132 to sealably close against the inside surface of the luer tip 1126. Further, the bladder member 1130 can be configured so that the volume within the inner cavity 1133 of the bladder member 1130 when the valve member 1120 is in the closed position (which is represented by V1 in FIG. 15A) can be greater than the volume of the cavity 1133 within the bladder member 1130 when the valve member 1120 is in the open position (which is represented by V2 in FIG. 15B). Thus, the volume of the cavity 1133 within the bladder member 1130 can decrease when the valve member 1120 moves from the closed position to the open position and can increase when the valve member 1120 moves from the open position to the closed position. By increasing the volume of the cavity 1133 within the bladder member 1130 as the valve member 1120 moves to the closed position, the bladder member 1130 can essentially create a force of suction that can reduce the amount of fluid or medicament that can flow through or drip out of the opening 1138 as the valve member 1120 is in the process of closing by drawing such fluid back toward the bladder member 1130.

In the illustrated embodiment, the luer connector 1110 can comprise a tube 1150 positioned within the inside surface of the port 1124 at the second end 1114 of the luer connector 1110. In the illustrated embodiment, the tube 1150 can be integrally formed with the bladder member 1130 and the tube 1132 at the first end 1112 of the luer connector 1110. Additionally, the luer connector 1110 can comprise a sealing member 1152 (which can be annular) configured to prevent fluid or medicament from entering into the chamber 1146 from the port 1124. The sealing member 1152 can comprise any of the materials, geometries, sizes, or other details of configurations of any other steel disclosed in FIGS. 12A-19D and the associated written disclosure. In some embodiments, the sealing member 1152 can be positioned between the outside surface of the tube 1150 and the inside surface of the port 1124 and can provide a generally fluid tight seal between the tube 1150 and the port 1124. In some embodiments, the sealing member 1152 can be formed from the same material as the tube 1150 and can be formed integrally with the tube 1150. In some embodiments, the sealing member 1152 can be formed separately from the tube 1150 and positioned at the desired axial location of either the tube 1150 or the inside surface of the port 1124. Accordingly, in some embodiments, either the inside surface of the port 1124 or the tube 1150 can comprise features such as channels or depressions to bias the sealing member 1152 to be secured in the desired location.

In some embodiments, as in the illustrated embodiment, the bladder member 1130, the tube 1132, sealing member 1144 and the tube 1150 in the sealing member 1152 can all be integrally formed from the same material. In some embodiments, however, any of these components can be formed separately and supported in the desired position as described above and relating to FIG. 12A and higher or in any other suitable manner. The housing 1122 can be generally a tube-like structure with a passageway 1154 that can extend from the second end 1114 of the connector 1110 through the axial center of the luer connector 1110. In some embodiments, when the luer connector 1110 is in the open configuration as illustrated in FIG. 15B, the passageway 1154 can permit fluid to flow from the second end 1114 through the port 1124, the tube 1150, the bladder member 1130, the tube 1132, and out through the opening 138 in the luer tip 1126 positioned at the first end 1112 of the luer connector 1110. With reference to FIGS. 15A and 15B, near the second end 1114 of the luer connector 1110, the port 1124 and the corresponding section of the fluid passageway 1154 can be sufficiently wide so as to accommodate a section of standard-diameter medical tubing inserted therein. The length, diameter, or other features and of the housing 1122 (or any housing disclosed in FIGS. 12A-19D and the associated written disclosure) can be the same as any other housing disclosed in FIGS. 12A-19D and the associated written disclosure. As with other embodiments of the connector, the port 1124 can be made to comply with applicable standards and/or regulations, such as the ANSI standards.

Additionally, the shroud 1128 can be sized and configured as described above and relating to FIG. 12A and higher or as desired to securely or removably attach the luer connector 1110 to another medical implement. Further, the housing 1122, tip 1126, bladder member 1130, or any other components or features of the luer connector 1110 may comprise any of the materials, shapes, features, sizes, or other configurations or details described with regard to any other tip member disclosed in FIGS. 12A-19D and the associated written disclosure. As with other embodiments, the luer tip 1126 can be made to comply with applicable standards and/or regulations, such as the ANSI standards.

With reference to FIG. 15B, as the male luer connector 1110 and female connector 1076 move towards each other into threaded engagement, the proximal end 1084 of the tip of the female connector 1076 contact the struts 1136 of the valve member 1120. As the male luer connector 1110 and female connector 1076 move further into threaded engagement, the struts 1136 can be moved toward the second end 1114 of the male connector 1110 by the female connector 1076, thereby displacing the valve member 1120 relative to the housing 1122. Thus, the distal end portion 1132*a* of the tube 1132 can move away from the interior distal end portion 1126*a* of the tip 1126 in the direction of the second end 1114 of the male connector 1110 as the male luer connector 1110 and female connector 1076 move further into threaded engagement. As these two surfaces move apart from one another, a gap can form between the tube 1132 and the luer tip 1126, permitting fluid to pass through the opening 1138 into the fluid passageway 1080 of the female connector 1076, or vice versa.

In some embodiments, as the valve member 1120 moves relative to the housing 1122, bladder member 1130 compresses, causing the bladder member 1130 to exert a force on the valve member 1120 biasing the valve member 1120 toward the closed position. The biasing force from the bladder member 1130 can be resisted by the radially extending surface 1078 of the female connector 1076 contacting the inner threads 1156 of the housing 1122. However, when the female connector 1076 is withdrawn from the male luer 1110, the bladder member 1130 can return the sealing portion of the valve member 1120 to the closed position within the luer tip 1126.

As shown in FIG. 15B, in the opened configuration, the fluid passageway 1080 of the female connector 1076 can communicate with the passageway 1154 of the valve member 1120 so as to allow fluid to flow through the passageway 1154 and the fluid passageway 1080 of the female connector 1076 in either direction. Fluid can thereby flow from tubing (not shown) or another connector or conduit that can be attached to the male luer 1110, into the passageway 1154 of the valve member 1120, through the opening or openings 1064 into the interior space 1060 within the luer tip 1126, out from the interior space 1060 within the luer tip 1126 through the opening 1138 at the distal end portion 1126a of the luer tip 1126 and into the fluid passageway 1080 of the female connector 1076, and vice versa. A fluid-tight closure can also be formed between corresponding tapers of the outside surface of the tip 1126 and the inner surface 1086 of the female connector 1076.

As discussed above, as the valve member 1120 opens, causing the bladder member 1130 to be compressed, the volume of fluid that can be contained within the cavity 1133 of the bladder member 1130 accordingly decreases. In some embodiments, a constant source of positive pressure can be imparted on the passageway 1154 at the second end 1114 of the luer connector 1110 while the bladder member 1130 is being compressed (which decreases the volume of fluid in the cavity 1133 of the bladder member 1130), and the fluid within the bladder member 1130 can be subjected to an increased pressure due to the compression of the bladder member 1130. In some embodiments, this increased pressure can cause the fluid within the bladder member 1130 to flow through the passageway 1154 toward the first end 1112 of the luer connector 1110 at an increased rate, until the pressure within the bladder member 1130 is equilibrated.

Conversely, in some embodiments, when the female connector 1076 is removed from the luer connector 1110, the valve member 1120 can move back toward the closed position, thereby causing the volume of the cavity 1133 within the bladder member 1130 to transition from volume V2 back to volume V1. The expansion of the interior volume of the bladder member 1130 can cause a reduced pressure or suction to be generated within the bladder member 1130, in effect a vacuum. This reduced pressure or suction can cause the bladder member 1130 to draw at least some of the fluid that is within the passageway 1154 near the first end 1112, and fluid on the outer surface of the tip 1132a, back toward the bladder member 1130. In some embodiments, the luer connector 1110 may be used to control the flow of fluids or medicaments that are harmful or corrosive. In these circumstances, preventing even a few drops from dripping out of the opening 1138 upon removal of the female connector 1076 can be especially beneficial.

Figure 15C:
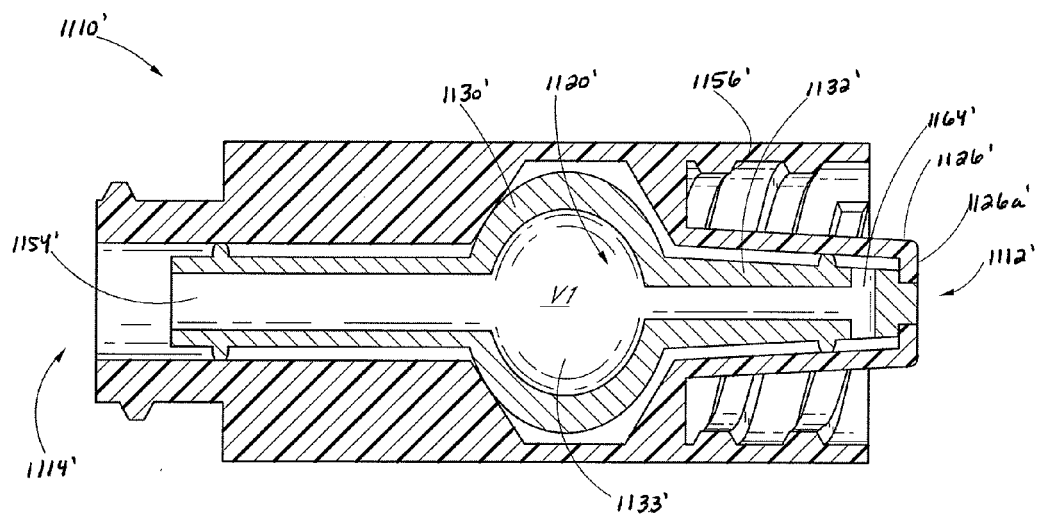
FIG. 15C is a cross-sectional view of another embodiment of a luer connector in a closed position.
Figure 15D:
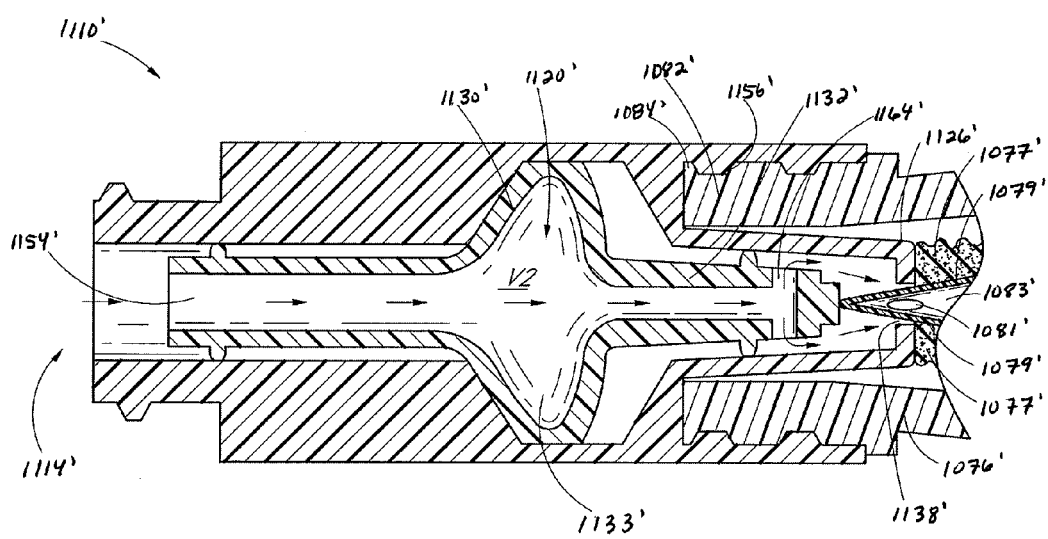
FIG. 15D is a cross-sectional view of the embodiment of the luer connector shown in FIG. 15C in an open position.

Referring now to FIGS. 15C-15D, some embodiments of the closeable luer connector 1110' will be described in greater detail. In some embodiments, the luer connector 1110' may comprise any of the components, features, materials, sizes, geometries, details, or configurations of any of the other luer connectors disclosed in FIGS. 12A-19D and the associated written disclosure. FIG. 15C is a cross-sectional view of the luer connector 1110' in a closed position. As described above, when the valve member 1120' of the luer connector 1110' fluid is in the closed position, fluid is generally prevented from flowing through the luer connector 1110'. FIG. 15D is a cross-sectional view of the embodiment of the luer connector 1110' in an open position due to the engagement of a female connector 1076' with the luer connector. The flow of fluid or medicament through the luer connector 1110' is represented by arrows in FIG. 15D. As described above, when the valve member 1120' of the luer connector 1110' is in the open position, fluid can be generally permitted to flow through the luer connector 1110'. As with any embodiment of the luer connector disclosed in FIGS. 12A-19D and the associated written disclosure, the seal or seals formed in the housing by the valve member is generally sufficient to resist fluid flow during normal operating conditions for medical valves.

In some embodiments, the luer connector 1110' can be the same or similar to the luer connector 1110' described above, with certain differences in some versions as illustrated and/or described below. First, in some embodiments, as in the illustrated embodiment, the valve member 1120' can be moved from the closed position (as illustrated in FIG. 15C) to the open position (as illustrated in FIG. 15D) without the use of the actuators or struts 1136 as described above with respect to luer connector 1110. With reference to FIG. 15D, the luer connector 110' can be threadedly engaged with the closeable female connector 1076'. The closeable female connector tip 1082' of the female connector 1076' can have a radially extending surface 1084' disposed on its external surface that can engage with the inner threads 1156' formed on the inside surface of the shroud 1128' of the luer connector 1110' to engage the connectors 1110', 1076' as illustrated. In the illustrated engagement, the fluid conduit 1079' of the female connector 1076' can advance through the opening 1138' in the luer tip 1126' by displacing the tube 1132' toward the second end 1114' of the luer connector 1110'. The tube 1132' can be configured so as to compress the bladder member 1130' when the tube 1132' is displaced (as illustrated in FIG. 15D), and to return to its closed position within luer tip 1126' (as illustrated in FIG. 15C) when the female connector 1076' is disengaged from the luer connector 1110'. As the bladder member 1130' is compressed, the volume within the cavity 1133' of the bladder member 1130' can decrease and exert a force on the tube 1132' so as to return the tube 1132' to the closed position within luer tip 1126' (as illustrated in FIG. 15C) when the female connector 1076' is disengaged from the luer connector 1110'.

Further, as illustrated, as the fluid conduit 1079' of the female connector 1076' advances through the opening 1138' in the luer tip 1126', a compressible seal element 1077' surrounding the fluid conduit 1079' can be compressed so as to allow the fluid conduit 1079' to protrude therethrough. The force exerted while engaging the connectors 1110', 1076' can be sufficient to compress the seal element 1077' to expose the one or more openings 1081' in the fluid conduit 1079'. With the seal element 1077' compressed, the fluid passageway 1083' can be in fluid communication with the interior space of the luer tip 1132'. As can be seen in FIG. 15D, the front surface of the fore portion 1126a' can contact the front surface of the sealing member 1077' so as to create and maintain a generally fluid tight seal therewith. The compressed seal element 1077' can inhibit fluid flowing into the interior of the closeable female connector 1076' beyond the luer tip 1132'. In this configuration, fluid can flow from the second end 1114' of the luer connector 1110', through at least the fluid passageway 1154', the bladder member 1130', the tube 1132', the one or more openings 1164' in the tube 1132', the opening 1138' in the luer tip 1126', through the one or more openings 1081' in the female connector 1076', and through the fluid passageway 1083'. Thus, in the engaged position, the fluid conduit 1079' can protrude through the compressible seal element 1077' to a sufficient extent so that the fluid passageway 1083' of the female connector 1076' is in fluid communication fluid passageway 1154' of the luer connector 1110'. In some embodiments, the luer connector 1110' can also comprise struts (not shown) as described above to allow the valve 1120' to be opened and closed, even if a female connector of the type illustrated in FIG. 15D is used.

Figure 16A:
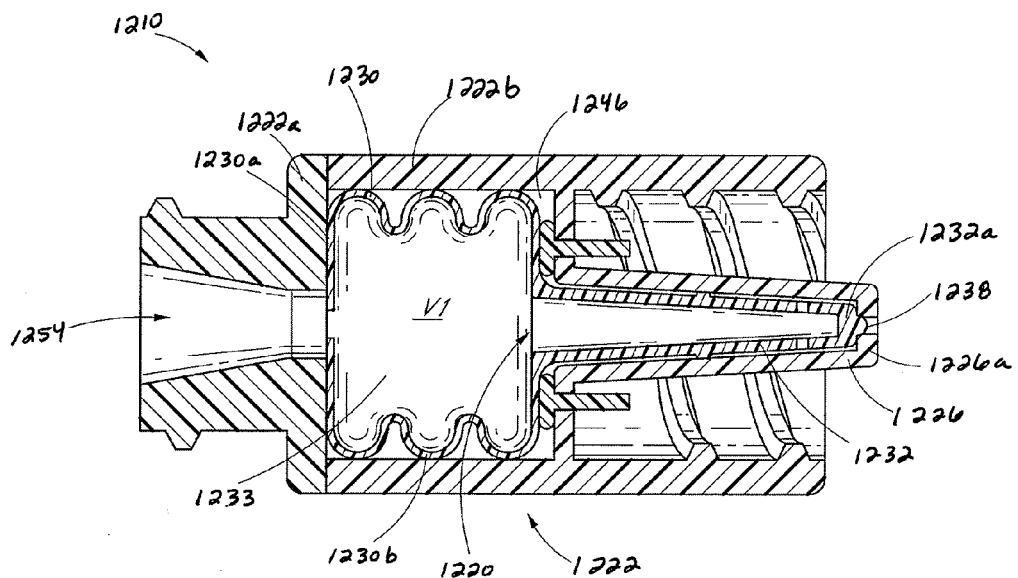
FIG. 16A is a cross-sectional view of another embodiment of a luer connector in a closed position.
Figure 16B:
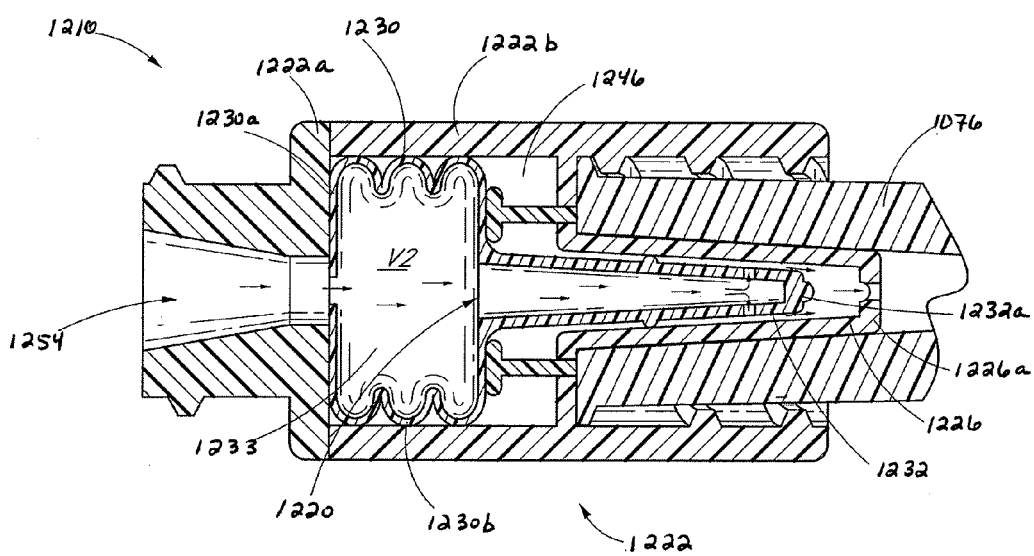
FIG. 16B is a cross-sectional view of the embodiment of the luer connector shown in FIG. 16A in an open position.

Referring now to FIGS. 16A-16B, some embodiments of the closeable luer connector 1210 will be described. In some embodiments, the luer connector 1210 may comprise any of the components, features, materials, sizes, geometries, details, or configurations of any of the other luer connectors disclosed in FIGS. 12A-19D and the associated written disclosure. FIG. 16A is a cross-sectional view of the luer connector 1210 in a closed position so that fluid is generally prevented from flowing through the luer connector 1210. FIG. 16B is a cross-sectional view of the embodiment of the luer connector 1210 in an open position, which can be caused by engagement of a female connector 1076 with the luer connector. The flow of fluid or medicament through the luer connector 10210 is represented by arrows in FIG. 16B. As described above, when the valve member 1210 of the luer connector 1210 is in the open position, fluid can be generally permitted to flow through the luer connector 1210.

In some embodiments, the luer connector 1210 can be the same or similar to the luer connector 1110 described above, with certain differences in some versions as illustrated and/or described below. Accordingly, in some embodiments, the luer connector 1210 may operate in the same or similar manner as compared to the luer connector 1110 described above. In some embodiments, as in the illustrated embodiment, the connector 1210 can include a valve member 1220 including a tube 1232 configured to generally complement the inner surface of the male luer 1226. At least a portion of the tube 1232 is configured to engage the inner surface of the male luer 1226 as discussed with other embodiments disclosed in FIGS. 12A-19D and the associated written disclosure.

A bladder member 1230 generally encloses an internal cavity 1233. The wall 1230b of the bladder member 1230 can define a corrugated shape, which can have multiple inward and outward folds in the side portion 1230b of the bladder member 1230. In some embodiments, the multiple inward and outward folds of the corrugated bladder member 1230 may facilitate compression of the bladder member 1230 as the female connector 1076 is threaded into the luer connector 1210. As with other connectors disclosed in FIGS. 12A-19D and the associated written disclosure, the volume of cavity 1233 can vary as the connector 1210 moves to and from the open and closed positions. Specifically, the cavity 1233 is preferably configured to change from a first large volume V1 when in the connector 1210 is in the closed position to a second smaller volume V2 when the connector 1210 is in the open position. The expansion of the interior volume of the bladder member 1230 when moving from the open to the closed position can cause a reduced pressure or suction to be generated within the bladder member 1230, in effect a vacuum. This reduced pressure or suction can cause the bladder member 1230 to draw at least some of the fluid that is within the passageway 1254 near the first end 1212, and fluid on the outer surface of the tip 1232a of tube 1232, back toward the bladder member 1230.

Additionally, in some embodiments, the aft portion 1230a of the bellows 1230 can be sealed to the aft portion 1222a of the housing to 1222 so as to prevent fluid or medicament that is passing through the luer connector 1210 from leaking between the aft portion 1230a of the bellows 1230 and the end portion 1222a of the housing 1222 into the chamber 1246 within the housing 1222. Additionally, the complementary mating surfaces of the end portion 1232a of the tube 1232 as well as the end portion 1226a of the luer tip 1226 can define alternative shapes and sizes as compared to other portions of the luer connectors disclosed in FIGS. 12A-19D and the associated written disclosure, as illustrated in FIGS. 16A and 16B. The shapes, sizes, features, or any other aspects of the luer connector 1210 illustrated in FIGS. 16A and 16B can be implemented in any luer connector disclosed in FIGS. 12A-19D and the associated written disclosure.

Figure 16C:
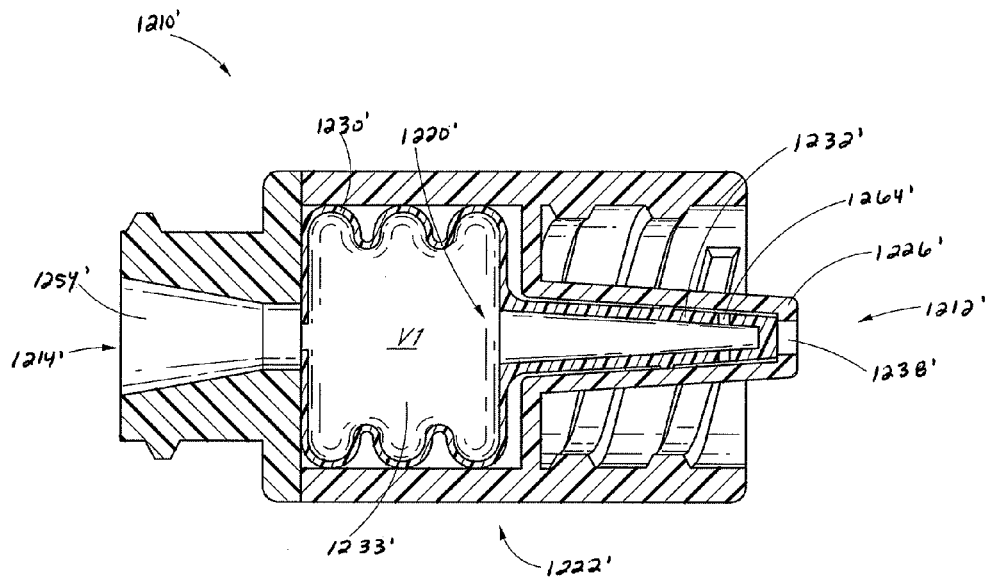
FIG. 16C is a cross-sectional view of another embodiment of a luer connector in a closed position.
Figure 16D:
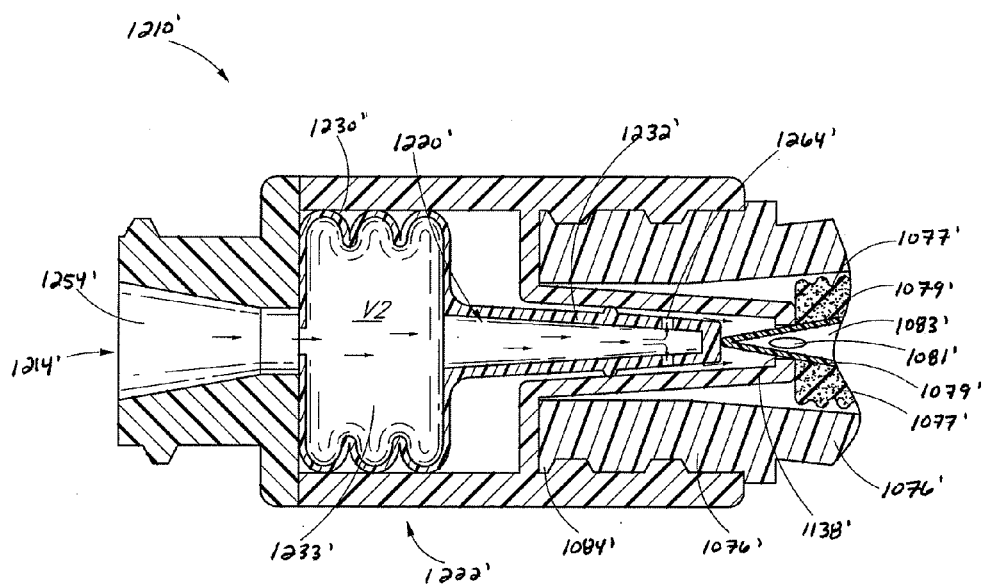
FIG. 16D is a cross-sectional view of the embodiment of the luer connector shown in FIG. 16C in an open position.

Referring now to FIGS. 16C-16D, some embodiments of the closeable luer connector 1210' will be described. In some embodiments, the luer connector 1210' may comprise any of the components, features, materials, sizes, geometries, details, or configurations of any of the other luer connectors disclosed in FIGS. 12A-19D and the associated written disclosure. FIG. 16C is a cross-sectional view of the luer connector 1210' in a closed position such that fluid is generally prevented from flowing through the luer connector 1210'. FIG. 16D is a cross-sectional view of the embodiment of the luer connector 1210' in an open position due to the engagement of a female connector 1076' with the luer connector. The flow of fluid or medicament through the luer connector 1210' is represented by arrows in FIG. 16D. As described above, when the valve member 1210' of the luer connector 1210' is in the open position, fluid can be generally permitted to flow through the luer connector 1210'.

In some embodiments, the luer connector 1210' can be the same or similar to the luer connector 1210' described above, with certain differences in some version as illustrated and/or described below. In some embodiments, as in the illustrated embodiment, the valve member 1220' can be moved from the closed position (as illustrated in FIG. 16C) to the open position (as illustrated in FIG. 16D) without the use of the actuators or struts 1236 as described above with respect to luer connector 1210. With reference to FIG. 16D, the luer connector 1210' can be threadedly engaged with the closeable female connector 1076'. The closeable female connector tip 1082' of the female connector 1076' can have a radially extending surface 1084' disposed on its external surface that can engage with the inner threads formed on the inside surface of the shroud 1228' of the luer connector 1210' to engage the connectors 1210', 1076' as illustrated. In the illustrated engagement, the fluid conduit 1079' of the female connector 1076' can advance through the opening 1238' in the luer tip 1226' by displacing the tube 1232' toward the second end 1214' of the luer connector 1210'. The tube 1232' can be configured so as to compress the bladder member 1230' when the tube 1232' is displaced as illustrated in FIG. 16D, and to return to its closed position within luer tip 1226' (as illustrated in FIG. 16C) when the female connector 1076' is disengaged from the luer connector 1210'. As the bladder member 1230' is compressed, the volume of the cavity 1233' within the bladder member 1230' can decrease and exert a force on the tube 1232' so as to return the tube 1232' to the closed position within luer tip 1226' (as illustrated in FIG. 16C) when the female connector 1076' can be disengaged from the luer connector 1210'. The change in volume can further result in a vacuum like effect, as discussed in connection with other embodiments disclosed in FIGS. 12A-19D and the associated written disclosure, that can draw fluid from the first end 1212' toward the bladder member 1230'.

Further, as illustrated, as the fluid conduit 1079' of the female connector 1076' advances through the opening 1238' in the luer tip 1226', a compressible seal element 1077' surrounding the fluid conduit 1079' can be compressed so as to allow the fluid conduit 1079' to protrude therethrough. The force exerted while engaging the connectors 1210', 1076' can be sufficient to compress the seal element 1077' to expose the one or more openings 1081' in the fluid conduit 1079'. With the seal element 1077' compressed, the fluid passageway 1083' can be in fluid communication with the interior space of the luer tip 1232'. As can be seen in FIG. 16D, the front surface of the fore portion 1226a' can contact the front surface of the sealing member 1077' so as to create and maintain a generally fluid tight seal therewith. The compressed seal element 1077' can inhibit fluid flowing into the interior of the closeable female connector 1076' beyond the luer tip 1232'. In this configuration, fluid can flow from the second end 1214' of the luer connector 1210', through at least the fluid passageway 1254', the bladder member 1230', the tube 1232', the one or more openings 1264' in the tube 1232', the opening 1238' in the luer tip 1226', through the one or more openings 1081' in the female connector 1076', and through the fluid passageway 1083'. Thus, in the engaged position, the fluid conduit 1079' can protrude through the compressible seal element 1077' to a sufficient extent so that the fluid passageway 1083' of the female connector 1076' can be in fluid communication with the fluid passageway 1254' of the luer connector 1210'. In some embodiments, the luer connector 1210' may also comprise struts (not shown) as described above and relating to FIG. 12A and higher to allow the valve 1220' to be opened and closed, even if a female connector of the type illustrated in FIG. 16D is used.

Figure 17A:
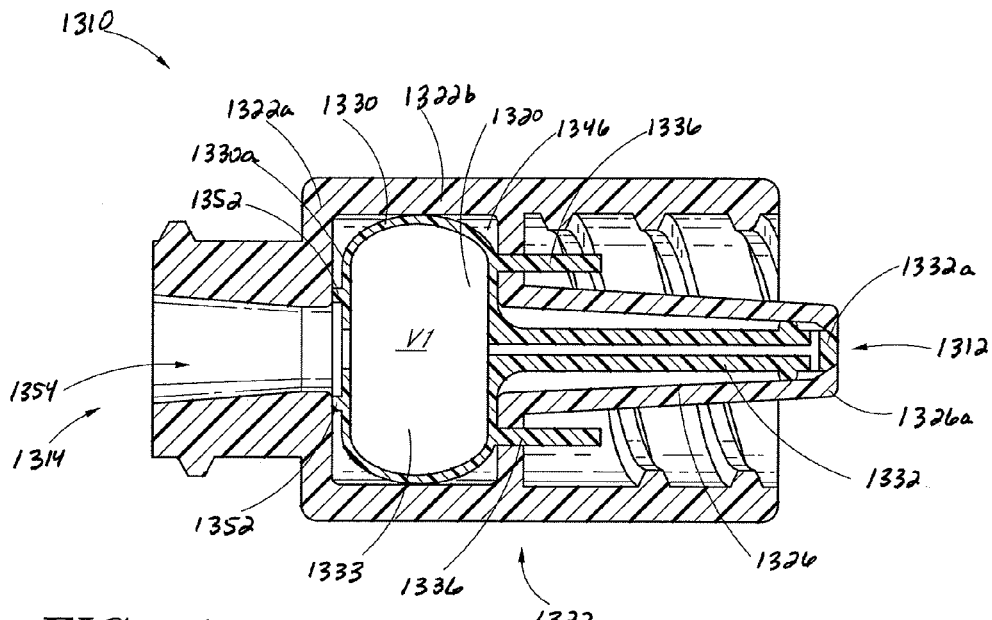
FIG. 17A is a cross-sectional view of another embodiment of a luer connector in a closed position.
Figure 17B:
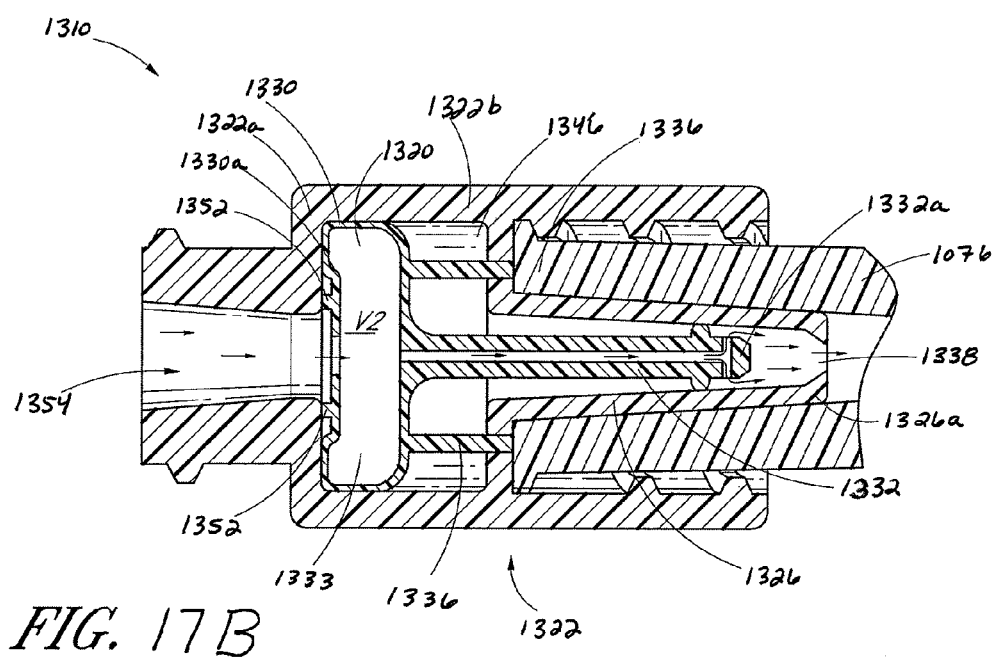
FIG. 17B is a cross-sectional view of the embodiment of the luer connector shown in FIG. 17A in an open position.

Referring now to FIGS. 17A-17B, some embodiments of the closeable luer connector 1310 will be described. In some embodiments, the luer connector 1310 may comprise any of the components, features, materials, sizes, geometries, details, or configurations of any of the other luer connectors disclosed in FIGS. 12A-19D and the associated written disclosure. FIG. 17A is a cross-sectional view of the luer connector 1310 in a closed position such that fluid is generally prevented from flowing through the luer connector 1310. FIG. 17B is a cross-sectional view of the embodiment of the luer connector 1310 in an open position due to the engagement of a female connector 1076 with the luer connector. The flow of fluid or medicament through the luer connector 1310 is represented by arrows in FIG. 17B. As described above, when the valve member 1320 of the luer connector 1310 is in the open position, fluid can be generally permitted to flow through the luer connector 1310.

In some embodiments, the luer connector 1310 can be the same or similar to the luer connector 1110 described above, with certain differences in some versions as illustrated and/or described below. Accordingly, in some embodiments, the luer connector 1310 may operate in the same or similar manner as compared to the luer connector 1110 described above. In some embodiments, the bladder member 1330, the tube 1332, and the valve struts 1336 may all be integrally formed. In some embodiments, the bladder member 1330, the tube 1332, and the valve struts 1336 may be all formed from the same material, such as a resilient rubber material like silicone, or may each be formed from a different material and adhered, bonded, fused, or otherwise attached together in a suitable manner. As with any of the valve struts described above and relating to FIG. 12A and higher, the valve struts 1336 can be suitably rigid and otherwise configured such that, when a female connector 1076 is threadingly engaged with the luer connector 1310, the struts 1336 can be axially depressed toward the bladder member 1330, causing the bladder member 1330 to compress. Additionally, in some embodiments, the bladder member 1330 may define a bellows-type shape, as illustrated in FIGS. 16A and 16B above. In some embodiments, the bladder member 1330 preferably defines an internal cavity 1333 with a volume that increases as the valve member 1320 moves from the open position to the closed position to effect a suction of fluid from the first end 1312 toward the second end 1314 of the connector.

In some embodiments, the aft portion 1330a of the bellows 1330 may define a sealing member 1352 that can be configured to seal the aft portion 1330a of the bladder member 1330 to the aft portion 1322a of the housing to 1322 so as to prevent any fluid or medicaments passing through the luer connector 1310 from leaking into the chamber 1346 within the housing 1322 during operation. In some embodiments, the sealing member 1352 may define an annular shape and may be positioned between the bladder member 1330 and the aft portion 1322a of the housing 1322. In some embodiments, the sealing member 1352 may be integrally formed with the bladder member 1330. Additionally, the complementary mating surfaces of the end portion 1332a of the tube 1332 as well as the end portion 1326a of the luer tip 1326 can define alternative shapes and sizes as compared to other portions of the luer connectors disclosed in FIGS. 12A-19D and the associated written disclosure, as illustrated in FIGS. 17A and 17B. The shapes, sizes, features, or any other aspects of the luer connector 1310 illustrated in FIGS. 17A and 17B can be implemented in any luer connector disclosed in FIGS. 12A-19D and the associated written disclosure.

Figure 17C:
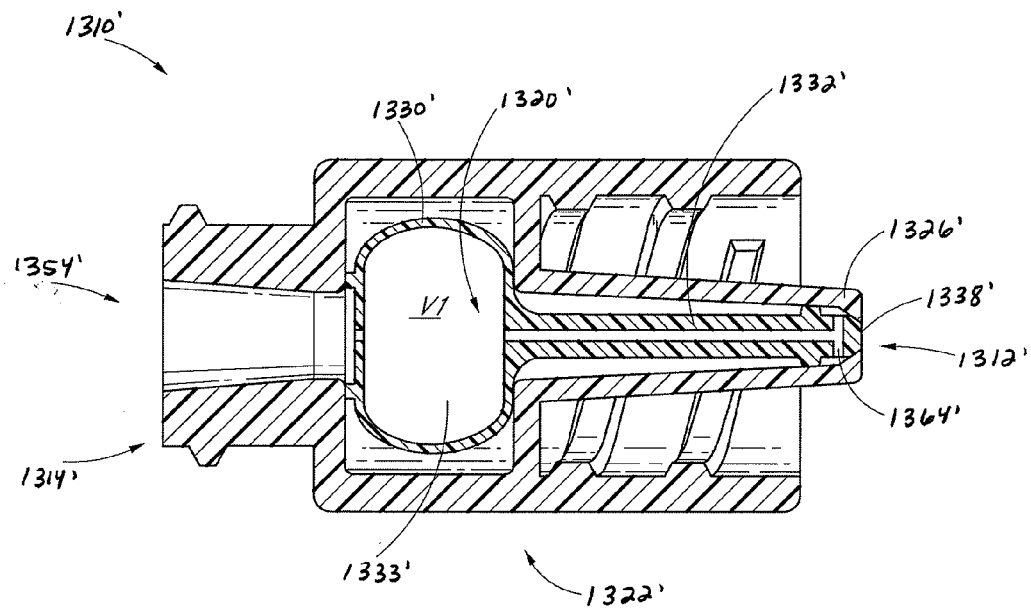
FIG. 17C is a cross-sectional view of another embodiment of a luer connector in a closed position.
Figure 17D:
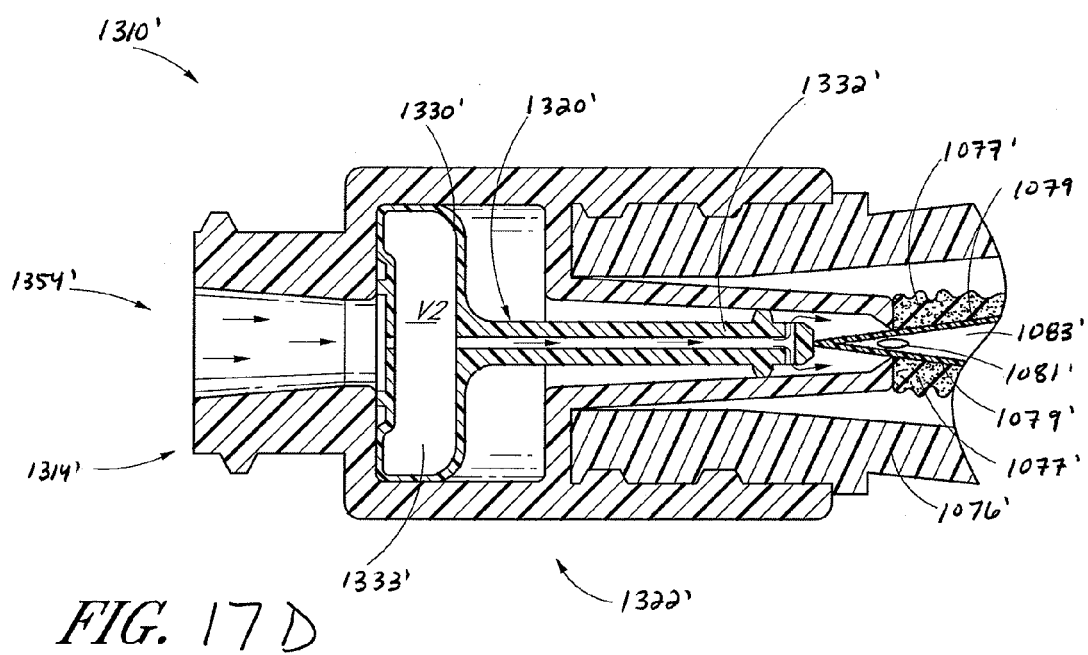
FIG. 17D is a cross-sectional view of the embodiment of the luer connector shown in FIG. 17C in an open position.

Referring now to FIGS. 17C-17D, some embodiments of the closeable luer connector 1310' will be described in greater detail. In some embodiments, the luer connector 1310' may comprise any of the components, features, materials, sizes, geometries, details, or configurations of any of the other luer connectors disclosed in FIGS. 12A-19D and the associated written disclosure. FIG. 17C is a cross-sectional view of the luer connector 1310' in a closed position such that fluid is generally prevented from flowing through the luer connector 1310'. FIG. 17D is a cross-sectional view of the embodiment of the luer connector 1310' in an open position due to the engagement of a female connector 1076' with the luer connector. The flow of fluid or medicament through the luer connector 1310' is represented by arrows in FIG. 17D. As described above, when the valve member 1310' of the luer connector 1310' is in the open position, fluid can be generally permitted to flow through the luer connector 1310'.

In some embodiments, the luer connector 1310' can be the same or similar to the luer connector 1310 described above, with certain differences in some versions as illustrated and/or described below. In some embodiments, as in the illustrated embodiment, the valve member 1320' can be moved from the closed position (as illustrated in FIG. 17C) to the open position (as illustrated in FIG. 17D) without the use of the actuators or struts 1336 as described above with respect to luer connector 1310. With reference to FIG. 17D, the luer connector 1310' can be threadedly engaged with the closeable female connector 1076'. The closeable female connector tip 1082' of the female connector 1076' can have a radially extending surface 1084' disposed on its external surface that can engage with the inner threads formed on the inside surface of the shroud 1328' of the luer connector 1310' to engage the connectors 1310', 1076' as illustrated. In the illustrated engagement, the fluid conduit 1079' of the female connector 1076' can advance through the opening 1338' in the luer tip 1326' by displacing the tube 1332' toward the second end 1314' of the luer connector 1310'. The tube 1332' can be configured so as to compress the bladder member 1330' when the tube 1332' is displaced as illustrated in FIG. 17D. As the bladder member 1330' is compressed, the volume of the cavity 1333' within the bladder member 1330' can decrease and exerts a force on the tube 1332' so as to return the tube 1332' to the closed position within luer tip 1326' (as illustrated in FIG. 17C) when the female connector 1076' is disengaged from the luer connector 1310'. Additionally, in some embodiments, the volume of space within the cavity 1333' of the bladder member 1330' can increase as the valve member 1320' returns to the closed position, creating a suction force that can draw excess fluid from the interior of the luer tip 1326' into the bladder member 1330'.

Further, as illustrated, as the fluid conduit 1079' of the female connector 1076' advances through the opening 1338' in the luer tip 1326', a compressible seal element 1077' surrounding the fluid conduit 1079' can be compressed so as to allow the fluid conduit 1079' to protrude therethrough. The force exerted to engage the connectors 1310', 1076' can be sufficient to compress the seal element 1077' to expose the one or more openings 1081' in the fluid conduit 1079'. With the seal element 1077' compressed, the fluid passageway 1083' can be in fluid communication with the interior space of the luer tip 1332'. As can be seen in FIG. 17D, the front surface of the fore portion 1326a' can contact the front surface of the sealing member 1077' so as to create and maintain a generally fluid tight seal therewith. The compressed seal element 1077' can inhibit fluid flow into the interior of the closeable female connector 1076' beyond the luer tip 1332'. In this configuration, fluid can flow from the second end 1314' of the luer connector 1310', through at least the fluid passageway 1354', the bladder member 1330', the tube 1332', the one or more openings 1364' in the tube 1332', the opening 1338' in the luer tip 1326', through the one or more openings 1081' in the female connector 1076', and through the fluid passageway 1083'. Thus, in the engaged position, the fluid conduit 1079' can protrude through the compressible seal element 1077' to a sufficient extent so that the fluid passageway 1083' of the female connector 1076' is in fluid communication fluid passageway 1354' of the luer connector 1310'. In some embodiments, the luer connector 1310' may also comprise struts (not shown) as described above and relating to FIG. 12A and higher to allow the valve 1320' to be opened and closed, even if a female connector of the type illustrated in FIG. 17D is used.

Figure 18A:
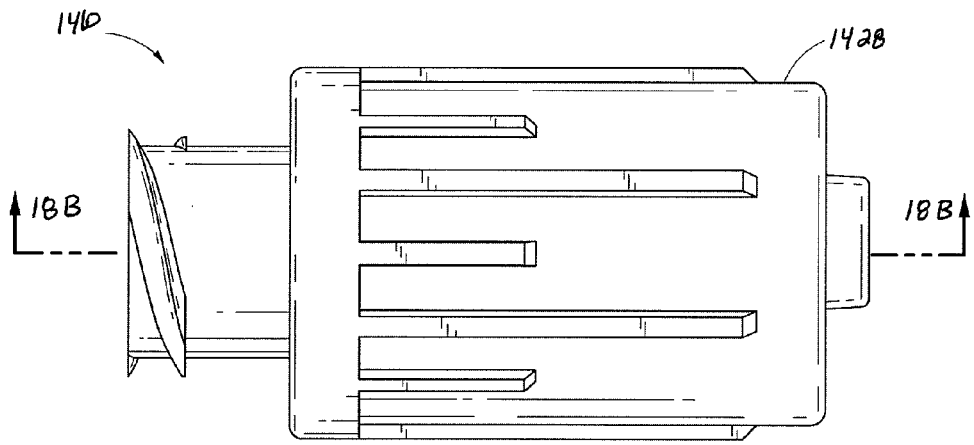
FIG. 18A is a side view of another embodiment of a luer connector.
Figure 18B:
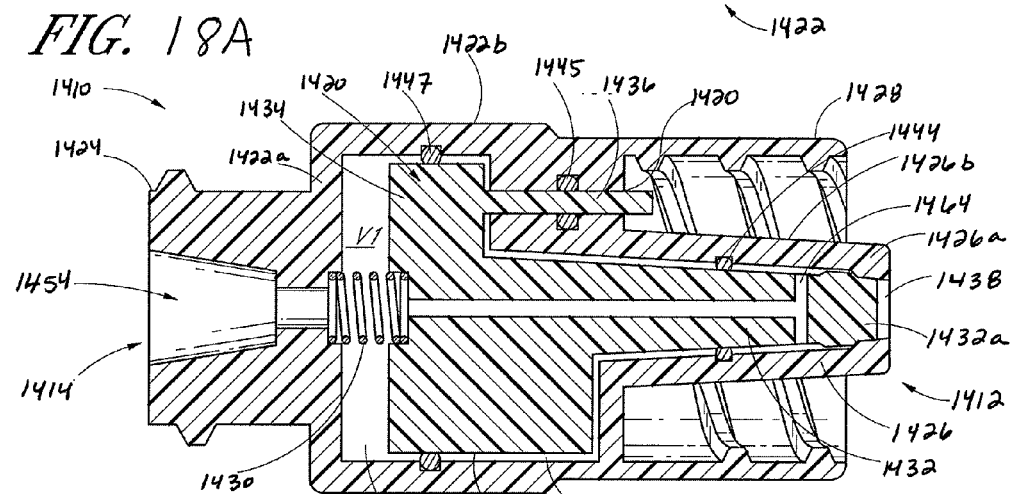
FIG. 18B is a cross-sectional view of the embodiment of the luer connector shown in FIG. 18A in a closed position.
Figure 18C:
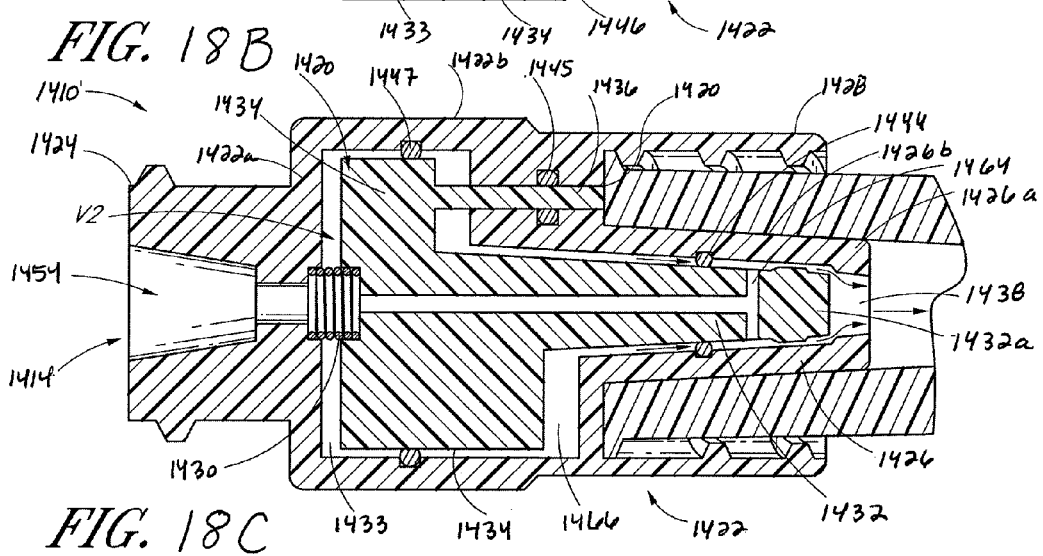
FIG. 18C is a cross-sectional view of the embodiment of the luer connector shown in FIG. 18A in an open position.

Referring now to FIGS. 18A-18C, some embodiments of the closeable luer connector 1410 will now be described. In some embodiments, the luer connector 1410 may comprise any of the components, features, materials, sizes, geometries, details, or configurations of any of the other luer connectors disclosed in FIGS. 12A-19D and the associated written disclosure. Detail and description of components or features that are similar to those of other luer connectors or other devices disclosed in FIGS. 12A-19D and the associated written disclosure may be limited or omitted.

FIG. 18A is a side view of the outside of the embodiment of the luer connector 1410. FIG. 18B is a cross-sectional view of the luer connector 1410 in a closed position so that fluid is generally prevented from flowing through the luer connector 1410. FIG. 18B is a cross-sectional view of the luer connector 1410, showing the valve member 1420 in an open position configured to permit the flow of fluid through the luer connector 1410.

As illustrated in FIG. 18A, some embodiments of the assembled luer connector 1410 can comprise a housing 1422, a port 1424 positioned near the second or distal end 1414 of the luer connector 1410, a luer tip 1426 positioned near the first or proximal end 1412 of the luer connector 1410, a shroud 1428 surrounding at least a portion of the luer tip 1426, a resilient spring member 1430 supported within the housing 1422, and the valve member 1420 mentioned above also supported within the housing 1422. In some embodiments, the spring member 1430 may be helical in shape and formed from a metallic material, such as stainless steel, spring alloy, or other suitable metallic material, or from a suitable plastic or rubber material in a helical shape or in the shape of a solid, hollow, or perforated cylinder.

In the illustrated embodiment, the valve member 1420 can comprise a tube 1432 projecting from a valve base 1434 toward the first end 1412 of the connector 1410, and a valve strut 1436 that can project from the valve base 1434. In some embodiments, in an assembled configuration, the luer connector 1410 may comprise more than one valve strut 1436, each of which can be positioned so as to be adjacent to the tip 1426 along two sides of the tip 1426. When the luer connector 1410 is in the closed position, the outer surface of the distal portion 1432a of the valve tube 1432 can be sealingly closed against the inner surface of the distal portion 1426a of the luer tip 1426 such that fluid is generally prevented from flowing through the opening 1438 formed in the distal and 1426a of the luer tip 1426.

In the illustrated embodiment, the tube 1432 can be slidably supported so as to translate axially within the luer tip 1426. Further, the valve struts 1436 that can be supported in a cantilevered disposition by the valve base 1434 can be configured so as to slide within the openings 1440 formed through the internal wall 1442 of the housing 1422. The number of openings 1440 through the internal wall 1442 can be equal to the number of the valve struts 1436 that can be supported by the valve base 1434. A sealing member 1444 (which can define an annular shape) can be positioned around the outside surface of the tube 1432 so as to provide a seal between the outside surface of the tube 1432 and the inside surface of the luer tip 1426 during the operation of the luer connector 1410 (i.e., as the valve member 1420 moves between the open and the closed positions). In some embodiments, the sealing member 1444 may be integrally formed with the luer tip 1426 or may be separately formed and fused to, adhered to, or otherwise attached to or supported by the luer tip 1426. In some embodiments, the sealing member 1444 may be integrally formed with the tube 1432 or may be separately formed and fused to, adhered to, or otherwise attached to or supported by the tube 1432.

Additionally, an annular sealing member 1445 can be positioned around the outside surface of each of the valve struts 1436 so as to provide a seal between each of the valve struts 1436 and each of the openings 1440 in the internal wall 1442, so as to prevent any fluid from flowing through the opening or openings 1440 into the chamber 1446. In the illustrated embodiment, the chamber 1433 is the space that is generally confined by the end wall 1422a of the housing 1422, the sidewall 1422b (which can be cylindrically shaped) of the housing 1422, and the internal wall 1442 formed in the housing 1422. Some embodiments of the luer connector 1410 can comprise a sealing member 1447 which, in some embodiments, can be annular, around the outside surface 1434a (which can be cylindrically shaped) of the valve base 1434. In some embodiments, the luer connector 1410 can be configured such that the sealing member 1447 remains in a constant position relative to the valve base 1434 so as to move with the valve base 1434 as the valve member 1420 moves between the open and the closed position.

In the illustrated embodiment, the spring member 1430 can be supported near the second end 1414 of the luer connector 1410 by the end wall 1422a of the housing 1422 and at the other end by the valve base 1434. The spring member 1430 can comprise an axial opening through the center thereof through which fluid or medicament can pass. Additionally, in some embodiments, a fluid may pass between the coils of the spring member 1430. The spring member 1430 can be resilient and biased toward an expanded position, as illustrated in FIG. 18B, so as to exert a force on the valve member 1420 that biases the valve member 1420 toward the closed position. In some embodiments, as the valve member 1420 moves relative to the housing 1422, the preferably resilient spring member 1430 will compress, causing the spring member 1430 to exert a force on the valve member 1420 that can bias the valve member 1420 toward the closed position. The biasing force from the spring member 1430 can be resisted by the threaded engagement of the female connector 1076 with the luer connector 1410. However, when the female connector 1076 is withdrawn from the male luer 1410, the spring member 1430 can return the sealing portion of the valve member 1420 to the closed position within the luer tip 1426.

In some embodiments, luer connector 1410 can be configured so that the volume within the chamber 1433 between the sealing member 1447 the valve base 1443, and the end wall 1422*a* of the housing when the valve member 1420 is in the closed position (which is represented by V1 in FIG. 18B) can be greater than volume within the chamber 1433 between the sealing member 1447, the valve base 1434, and the end wall 1422*a* when the valve member 1420 is in the open position (which is represented by V2 in FIG. 18C). In these embodiments, the sealing member 1447 can move with the valve base 1434 along a portion of the inside surface of the sidewall 1422*b* of the housing 1422. In some embodiments, the sidewall 1422*b* of the housing 1422 can define a generally cylindrical shape. Thus, in these embodiments, the volume of space within the portion of the chamber 1433 described above can increase when the valve member 1420 moves from the open position to the closed position, so as to create a force of suction that can reduce the amount of fluid or medicament that can flow through or drip out of the opening 1438, or to retract dripping fluid back into the opening 1438, as the valve member 1420 is closed.

In some embodiments, any of the features of the valve member 1420, including the valve tube 1432, the valve base 1434, and the valve struts 1436 can be integrally formed, or in other embodiments, can be separately formed and adhered or otherwise joined together in subsequent manufacturing steps. In some embodiments, the end wall 1422*a* can be formed integrally with at least the sidewalls 1422*b* of the housing 1422. In some embodiments, the end wall 1422*a* can be formed separately as compared to at least the sidewalls 1422*b* and joined or adhered thereto in a subsequent manufacturing step.

The housing 1422 can be generally a tube-like structure with a passageway 1454 that can extend from the second end 1414 of the connector 1410 through the axial center of the luer connector 1410. Thus, in some embodiments, when the luer connector 1410 is in the open configuration as illustrated in FIG. 18C, the passageway 1454 can permit fluid to flow from the second end 1414 through the port 1424, the spring member 1430, the tube 1432, and out through the opening 1438 in the luer tip 1426 positioned at the first end 1412 of the luer connector 1410. With reference to FIGS. 18B and 18C, near the second end 1414 of the luer connector 1410, the port 1424 and the corresponding section of the fluid passageway 1454 can be adapted to accommodate a section of standard-diameter medical tubing inserted therein or a standard male luer tip.

FIG. 18C is a cross-sectional view of the luer connector 1410 of the luer connector 1410 in an open position so that fluid is generally permitted to flow through the luer connector 1410. The flow of fluid or medicament through the luer connector 1410 is represented by arrows in FIG. 18C. With reference to FIG. 18C, the valve member 1420 has preferably been moved to the open position by the insertion the female connector 1076. As shown in FIG. 18C and discussed above, the struts 1436 of the valve member 1420 can extend through openings 1440 in the internal wall 1442 of the housing 1422 such that, in the closed position, the ends of the struts 1436 extend past the internal wall 1442 toward the first end 1412 of the connector 1410. As with other luer connectors described above and relating to FIG. 12A and higher, the struts 1436 can be configured to engage the proximal ends 1084 of the female connector 1076 as the female connector 1076 advances into engagement with the closeable male luer 1410. FIG. 18C illustrates a cross-section of an embodiment of the luer connector 1410 wherein the valve member 1420 has been caused to be opened by the insertion of an exemplifying female connector 1076 in a similar manner as other luer connectors comprising struts described above and relating to FIG. 12A and higher.

As shown in FIG. 18C, the two connectors 1410, 1076 can be threadedly engaged toward one another until the taper of the inner surface 1086 of the female luer connector 1076 lies adjacent to or abuts the correspondingly tapered external surface 1426*b* of the tip 1426, or until two luers 1410, 1076 can be sealingly engaged and the valve member 1420 has been moved to the open position (as described above and relating to FIG. 12A and higher or in connection with any similarly configured luer connectors or valve members). In other embodiments, the two luers 1410, 1076 may be threadedly engaged until the second end of the tip 1426 forms a closure with a corresponding surface (not shown) of the female connector 1076.

Additionally, when used with certain alternative embodiments of the female connector 1076 an internal fluid conduit of the female connector 1076 may contact the distal end portion 1432*a* of the tube 1432 before the housing of the female connector 1076 contacts the struts 1436 (if any), thereby opening the male connector 1410. In some embodiments, the closure may remain intact until the inner surface 1086 of the tip of the female connector 1076 has formed a closing engagement with the outer surface of the tip 1426 of the luer connector 1410, inhibiting fluid within the passageway 1454 of the luer connector 1410 from being exposed to the external environment.

Figure 18D:
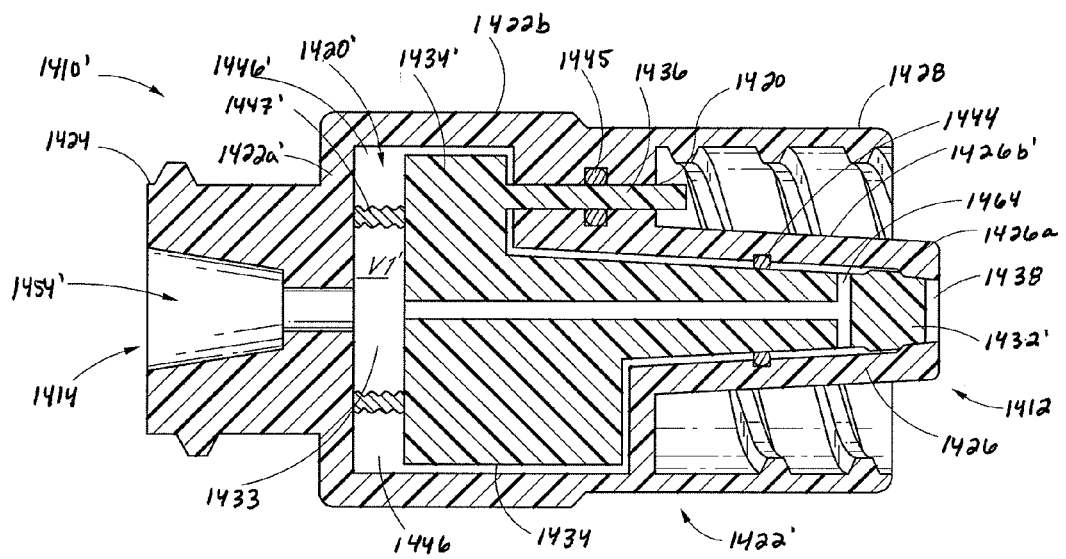
FIG. 18D is a cross-sectional view of another embodiment of a luer connector in a closed position.
Figure 18E:
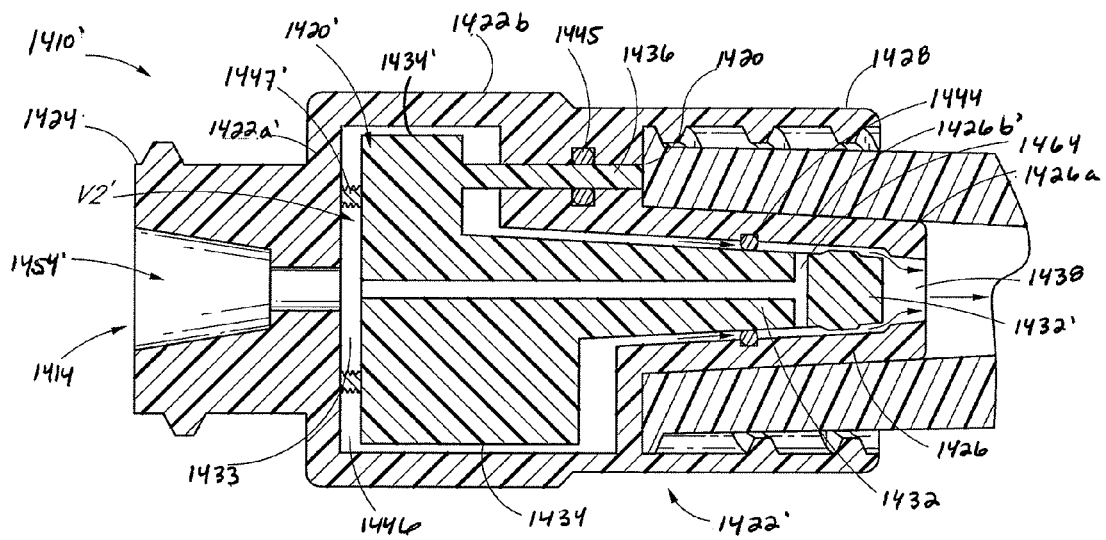
FIG. 18E is a cross-sectional view of the embodiment of the luer connector shown in FIG. 18D in an open position.

Referring now to FIGS. 18D-18E, some embodiments of the closeable luer connector 1410' will be described in greater detail. In some embodiments, the luer connector 1410' may comprise any of the components, features, materials, sizes, geometries, details, or configurations of any of the other luer connectors disclosed in FIGS. 12A-19D herein and in their accompanying written description. In particular, in the illustrated embodiment, the luer connector 1410' can be formed and configured to have the same features as the luer connector 1410 described above, with the exception of the spring member 1430 and the sealing member 1447 of the luer connector 1410, which will now be described.

With reference to FIG. 18D, the sealing member 1447' can be positioned between the preferably generally planar surface of the valve base 1434' and the preferably generally planar interior surface of the end wall 1422*a*'. In some embodiments, the valve base 1434' in the interior surface of the end wall 1422*a*' may define a depression or other features to support the sealing member 1447'. Additionally, in some embodiments, the sealing member 1447' may be secured to either the valve base 1434' or the interior surface of the end wall 1422*a*' with an adhesive or by any other suitable method. As illustrated in FIGS. 18D and 18E, the sealing member 1447' may provide a generally fluid tight seal to prevent fluid that is flowing through the passageway 1454' from leaking into the cavity 1446' outside of the sealing member 1447'. Additionally, as with other embodiments of luer connectors described above and relating to FIG. 12A and higher, the luer connector 1410' can be configured to provide a reduced pressure or suction so as to draw fluid from the opening or openings 1464 within the luer tip 1426 into the sealing member 1447' as the valve member 1420' moves to the closed position.

In particular, similar to other luer connectors described above and relating to FIG. 12A and higher, the volume of space of the cavity 1433' generally formed within the sealing member 1447' when the luer connector 1410' is in the closed position (which is represented by V1' in FIG. 18D) can be larger than the volume of space within of the cavity 1433' of the sealing member 1447' when the luer connector 1410' is in the open position (which is represented by V2' in FIG. 18D). The increase in the volume of the cavity 1433' within the sealing member 1447' as the valve member 1420' moves from the closed to the open position can create a reduced pressure that draws the fluid from the luer tip 1426' or tube 1432' back into the passageway 1454'.

Additionally, in some embodiments, the sealing member 1447' may be formed from a resilient material such as, but not limited to, silicone, rubber, or other suitable material, that exerts a tensile force on the valve base 1434' as the sealing member 1447' is being compressed (i.e., when the valve member 1420' is moved from the closed to the open position). In these embodiments, the tensile force created by the sealing member 1447' can bias the valve member 1420' toward the closed position, so that a separate spring member is not required. However, in some embodiments, the luer connector 1410' may comprise both the sealing member 1447' and an axial spring member, similar to any of the spring members described above and relating to FIG. 12A and higher. Further, in some embodiments, an axial spring member made from a suitable metal or any other suitable material may be formed integrally with the sealing member 1447'.

Figure 18F:
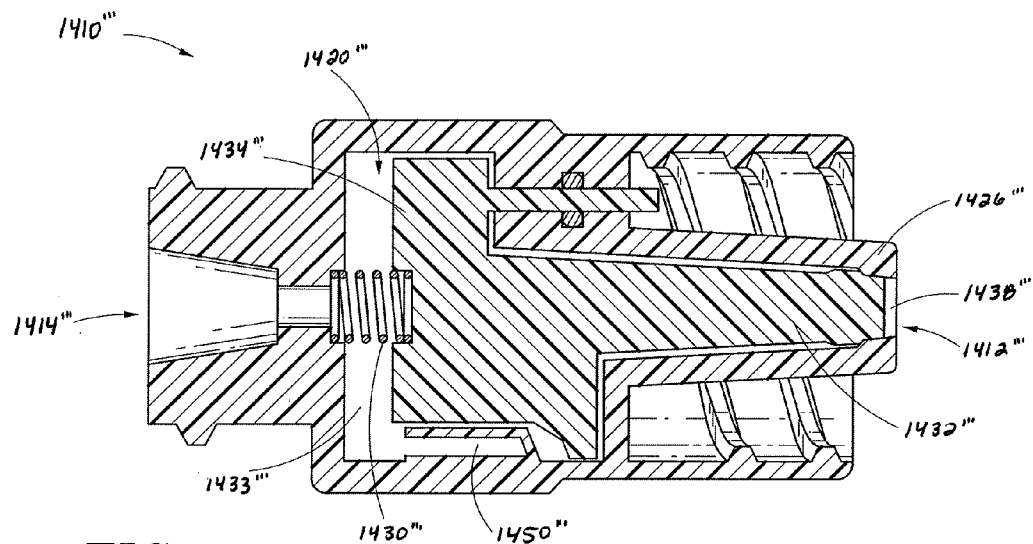
FIG. 18F is a cross-sectional view of another embodiment of a luer connector in a closed position.
Figure 18G:
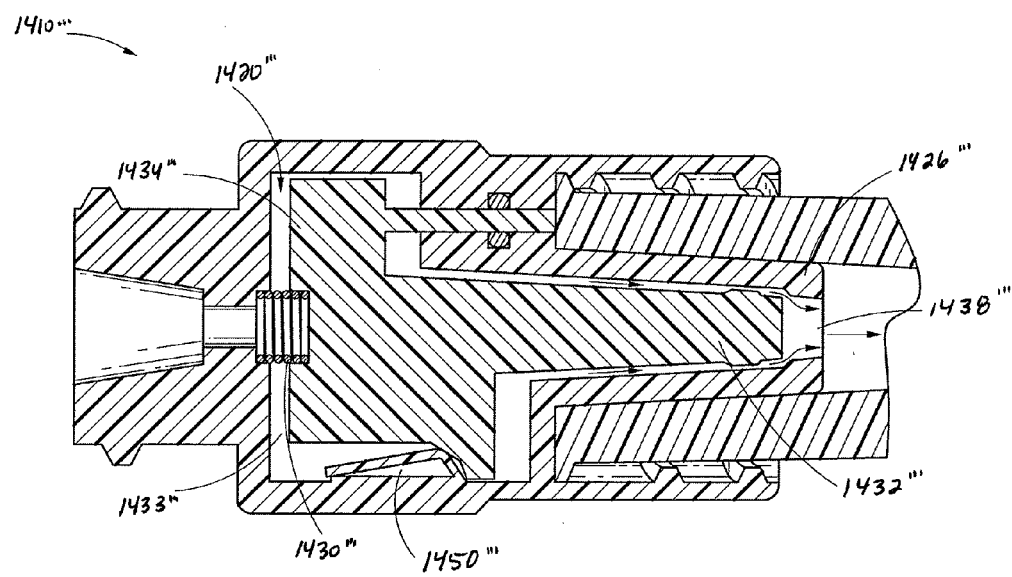
FIG. 18G is a cross-sectional view of the embodiment of the luer connector shown in FIG. 18F in an open position.

Referring now to FIGS. 18F-18G, some embodiments of the closeable luer connector 1410" will be described in greater detail. In some embodiments, the luer connector 1410" may comprise any of the components, features, materials, sizes, geometries, details, or configurations of any of the other luer connectors disclosed in FIGS. 12A-19D and the associated written disclosure. For example, in the illustrated embodiment, the luer connector 1410" can be formed and configured to have the same features as the luer connector 1410, with certain differences in some versions as described below. The valve member 1420" can be configured so that the fluid flow path goes around the valve member 1420" instead of through an internal opening in the valve member as described above with respect to luer connector 1410. Accordingly, the luer connector 1410" can be formed so as to not have a sealing member surrounding the valve member 1420", which would otherwise obstruct the fluid flow path.

Additionally, in the illustrated embodiment, the luer connector 1410" can be configured to generally prevent leakage through the opening 1438" at the end of the luer tip 1426" as the valve member 1420" is moved to the closed position. In particular, the luer connector 1410" can comprise a vacuum member 1450" that can be configured so as to provide a source of reduced pressure to the chamber 1433" as the valve member 1420" is moving towards the closed position.

Figure 19A:
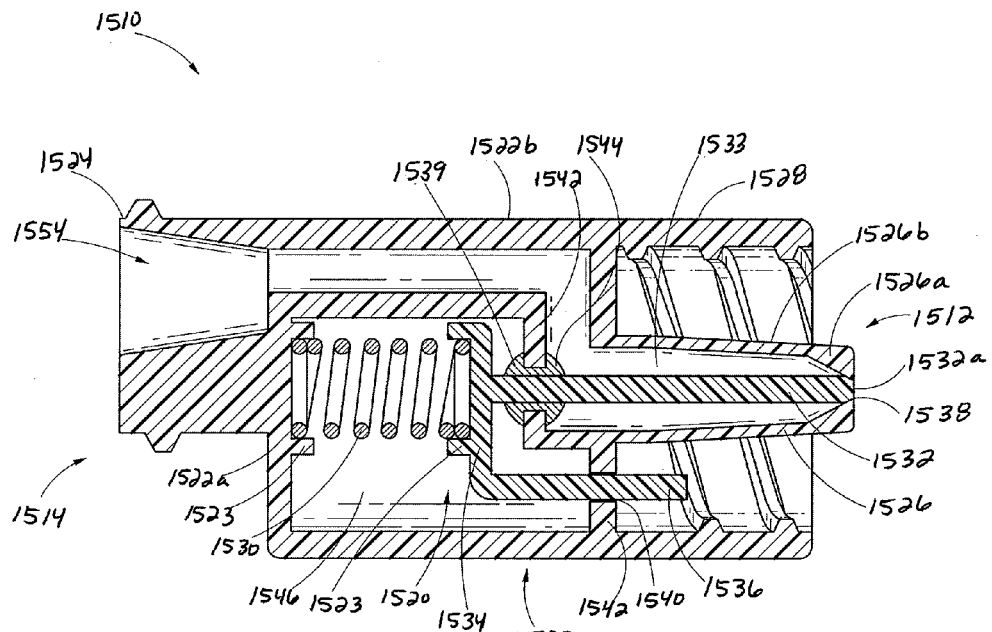
FIG. 19A is a cross-sectional view of another embodiment of a luer connector in a closed position.
Figure 19B:
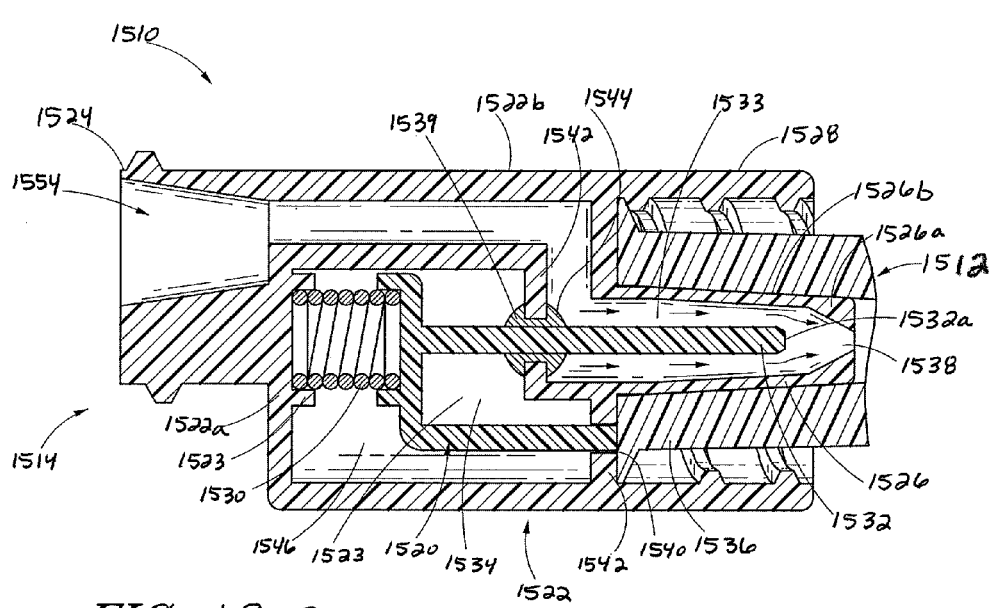
FIG. 19B is a cross-sectional view of the embodiment of the luer connector shown in FIG. 19A in an open position.

Referring now to FIGS. 19A-19B, some embodiments of the closeable luer connector 1510 will now be described. In some embodiments, the luer connector 1510 may comprise any of the components, features, materials, sizes, geometries, details, or configurations of any of the other luer connectors disclosed in FIGS. 12A-19D and the associated written disclosure. Detail and description of components or features that are similar to those of other luer connectors or other devices disclosed in FIGS. 12A-19D and the associated written disclosure may be limited or omitted.

FIG. 19A is a cross-sectional view of the luer connector 1510 in a closed position so that fluid is generally prevented from flowing through the luer connector 1510. FIG. 19B is a cross-sectional view of the luer connector 1510 in an open position. The flow of fluid or medicament through the luer connector 1510 is represented by arrows in FIG. 19B. In the open position, the valve member 1520 can be adapted to facilitate the flow of fluid through the luer connector 1510 by opening a channel through the connector 1510.

As illustrated in FIG. 19A, some embodiments of the assembled luer connector 1510 can comprise a housing 1522, a port 1524 positioned near the second end 1514 of the luer connector 1510, a luer tip 1526 positioned near the first end 1512 of the luer connector 1510, a shroud 1528 surrounding at least a portion of the luer tip 1526, a resilient spring member 1530 supported within the housing 1522, and the valve member 1520 mentioned above also supported within the housing 1522. In some embodiments, the spring member 1530 may be helical in shape and formed from a metallic material, such as stainless steel, spring alloy, or other suitable metallic material. In some embodiments, the spring member 1530 may be formed from a suitable plastic or rubber material, and may be formed in a helical shape, or in the shape of a solid or hollow cylinder. In some embodiments, as in the illustrated embodiment, the valve base 1534 and the end portion 1522a of the housing 1522 can be configured to provide lateral support to the end portions spring member 1530 so as to prevent the end portions of the spring member 1530 from moving in a transverse direction. In particular, the valve base 1534 and the end portion 1522a of the housing 1522 may define protrusions 1523 that can circumscribe the end portions of the spring member 1530. In other embodiments, valve base 1534 and the end portion 1522a may comprise other features such as, but not limited to, depressions, channels, adhesive or other suitable materials or features to suitably secure the end portion of the spring member 1530.

In the illustrated embodiment, the valve member 1520 can comprise a tube 1532 projecting from a valve base 1534 toward the first end 1512 of the connector 1510, and a valve strut 1536 that can also project from the valve base 1534. In some embodiments, in an assembled configuration, the luer connector 1510 may comprise more than one valve strut 1536, each of which can be positioned so as to be adjacent to the tip 1526 along two sides of the tip 1526. When the valve member 1520 of the luer connector 1510 is in the closed position, the outer surface of the distal portion 1532a of the valve tube 1532 can be sealingly closed against the inner surface of the distal portion 1526a of the luer tip 1526 such that fluid can be generally prevented from flowing through the opening 1538 formed in the distal end 1526a of the luer tip 1526. In some embodiments, the end portion 1532a of the tube 1532 can comprise any size, geometry, material or materials, or other features or details as would be suitable for the tube 1532, or as described above with regard to any other tubes disclosed in FIGS. 12A-19D and the associated written disclosure.

In the illustrated embodiment, the tube 1532 can be slidably supported so as to translate axially within an opening 1539 in the internal wall 1542 of the housing 1522, as well as to translate axially within the luer tip 1526. Further, the valve strut 1536 can be supported in a cantilevered disposition by the valve base 1534 and can be configured so as to slide within the opening 1540 formed through the internal wall 1542 of the housing 1522. In some embodiments, the luer connector 1510 may comprise a seal between the valve strut 1536 and the opening 1540 to prevent fluid from leaking into the chamber 1546. The number of openings 1540 through the internal wall 1542 can be equal to the number of the valve struts 1536 that can be supported by the valve base 1534.

A sealing member 1544 (which can be generally annular in shape) can be positioned around the outside surface of the tube 1532 so as to seal the opening 1539 as the tube 1532 slides axially therethrough during the operation of the luer connector 1510 (i.e., as the valve 1520 moves between the open and the closed positions). In some embodiments, the sealing member 1544 may be integrally formed with the luer tip 1526 or may be separately formed and fused to, adhered to, or otherwise attached to or supported by the luer tip 1526. In some embodiments, the sealing member 1544 may be integrally formed with the internal wall 1542 of the housing 1522 or may be separately formed and fused to, adhered to, or otherwise attached to or supported by the internal wall 1542 of the housing 1522.

In the illustrated embodiment, the spring member 1530 can be supported near the second end 1514 of the luer connector 1510 by the end wall 1522a of the housing 1522 and at the other end by the valve base 1534. The spring member 1530 can be resilient and biased toward an expanded position, as illustrated in FIG. 19A, so as to exert a force on the valve member 1520 that biases the valve member 1520 toward the closed position. In some embodiments, as the valve member 1520 moves relative to the housing 1522, the spring member 1530 can compress, increasing the force that is exerted on the valve member 1520. The biasing force from the spring member 1530 can be resisted by the threaded engagement of the female connector 1076 with the luer connector 1510. However, when the female connector 1076 is withdrawn from the luer connector 1510, the spring member 1530 can return the sealing portion of the valve member 1520 to the closed position within the luer tip 1526.

In some embodiments, any of the features of the valve member 1520, including the valve tube 1532, the valve base 1534, and the valve struts 1536 can be integrally formed, or, in other embodiments, can be separately formed and adhered or otherwise joined together in subsequent manufacturing steps. In some embodiments, the end wall 1522a can be formed integrally with at least the sidewalls 1522b of the housing 1522. In some embodiments, the end wall 1522a can be formed separately as compared to at least the sidewalls 1522b and joined or adhered thereto in a subsequent manufacturing step.

The housing 1522 can be generally a tube-like structure with a passageway 1554 that can extend from the second end 1514 of the connector 1510. With reference to FIGS. 19A and 19B, the fluid passageway 1554 can channel the fluid or medicament flowing through the luer connector 1510 around the chamber 1546 in which the valve base 1534 and spring member 1530 can be positioned. The passageway 1554 defines a cavity 1533. In some embodiments, routing the fluid passageway 1554 around the chamber 1546 may decrease the volume of the cavity 1533 within the passageway 1554 which can increase the fluid volume efficiency of the luer connector 1510, i.e., it can reduce the amount of fluid that may be trapped in the luer connector 1510 when the valve member 1520 is closed. Thus, in some embodiments, when the luer connector 1510 is in the open configuration as illustrated in FIG. 19B, the passageway 1554 can permit fluid to flow from the second end 1514 through the passageway 1554 and out through the opening 1538 in the luer tip 1526. As shown in FIG. 19B, in the opened configuration, the fluid passageway 1080 of the female connector 176 can communicate with the passageway 1554 of the valve member 1520 so as to allow fluid to through the passageway 1554 and the fluid passageway 1080 of the female connector 1076 in either direction.

With reference to FIG. 19B, as with certain other luer connectors disclosed in FIGS. 12A-19D and the associated written disclosure, the valve member 1520 has preferably been moved to the open position by the insertion the female connector 1076. As shown in FIG. 19B, the struts 1536 of the valve member 1520 can extend through openings 1540 in the internal wall 1542 of the housing 1522 such that, in the closed position, the ends of the struts 1536 extend past the internal wall 1542 toward the first end 1512 of the connector 1510.

As shown in FIG. 19B, the two connectors 1510, 1076 can be threadedly engaged towards one another until the taper of the inner surface 1086 of the female luer connector 1076 lies adjacent to or abuts the correspondingly tapered external surface 1526b of the tip 1526, or until two luers 1510, 1076 are sealingly engaged and the valve member 1520 has been moved to the open position (as described above or in connection with any similarly configured luer connectors or valve members). In some embodiments, the two luers 1510, 1076 may be threadedly engaged until the second end of the tip 1526 forms a closure with a corresponding surface (not shown) of the female connector 1076.

Additionally, when used with certain alternative embodiments of the female connector 1076, an internal fluid conduit of the female connector 1076 may contact the distal end portion 1532a of the tube 1532 before the housing of the female connector 1076 contacts the struts 1536 (if any), thereby opening the male connector 1510. In some embodiments, the closure may remain intact until the inner surface 1086 of the tip of the female connector 1076 has formed a closing engagement with the outer surface of the tip 1526 of the luer connector 1510, preventing any fluid within the passageway 1554 of the luer connector 1510 from ever being exposed to the external environment.

Figure 19C:
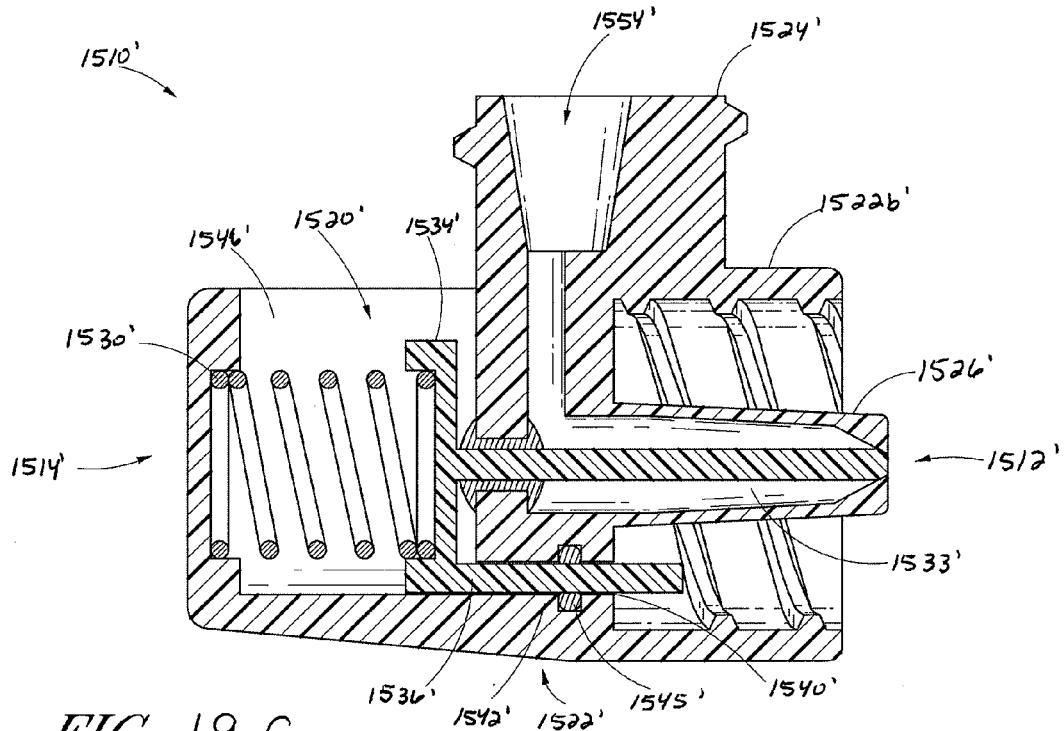
FIG. 19C is a cross-sectional view of another embodiment of a luer connector in a closed position.
Figure 19D:
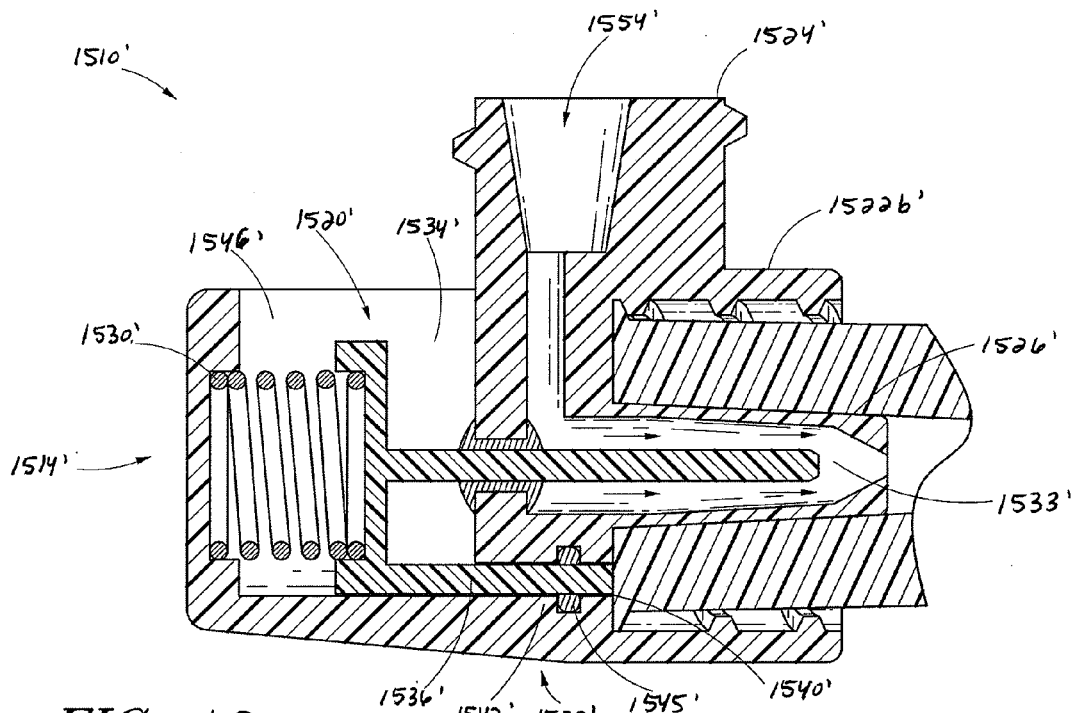
FIG. 19D is a cross-sectional view of the embodiment of the luer connector shown in FIG. 19C in an open position.

With reference to FIGS. 19C and 19D, another configuration of the luer connector 1510 will be described. With reference to FIGS. 19C and 19D, the luer connector 1510' may comprise any of the components, features, materials, sizes, geometries, details, or configurations of any of the other luer connectors disclosed in FIGS. 12A-19D and the associated written disclosure. For example, the luer connector 1510' can be configured so that the port 1524' of the luer connector 1510' is positioned to protrude from a side wall 1522b' of the housing 1522'. In the illustrated embodiment, the luer connector 1510' can be formed and configured to have the same or similar features as the luer connector 1510 described above with some differences. The luer connector 1510' can be configured so that the port 1524' of the luer connector 1510' is positioned to protrude from a side wall 1522b' of the housing 1522'.

Accordingly, the luer connector 1510' can be configured such that the fluid passageway 1554' flowing into the port 1524' can be oriented at an approximately 90 degree angle as compared to the fluid flow path within the luer tip 1526'. This arrangement, as illustrated in FIGS. 19C and 19D, may facilitate the attachment of the luer connector 1510' to particular connectors at the port 1524' portion or at the first end 1512' of the luer connector 1510'. The passageway 1554' can further define a fluid cavity 1533' of the connector 1510'.

Additionally, in some embodiments, the chamber 1546' in which the spring member 1530' and the valve base member 1534' can be positioned may define an open portion (as in the illustrated embodiments), which may provide access to the spring member 1530' and portions of the valve member 1520'. Additionally, in some embodiments, the luer connector 1510' may comprise an annular sealing member 1545' that can be positioned around the outside surface of each of the valve struts 1536' so as to provide a seal between each of the valve struts 1536' and each of the openings 1540' in the internal wall 1542', so as to prevent fluid from flowing through the opening or openings 1540' into the chamber 1546', where such fluid could potentially flow to the chamber 1546' and come into contact with the patient or medical practitioner using the luer connector 1510'.

Any features of the embodiments shown and/or described in FIGS. 12A-19D that have not been expressly described in this text, such as distances, proportions of components, etc. are also intended to form part of this disclosure. Additionally, although disclosed in the context of various embodiments, features, aspects, and examples, it will be understood by those skilled in the art that the present disclosure extends beyond the specifically disclosed embodiments to other alternative embodiments and/or uses and obvious modifications and equivalents thereof. Accordingly, it should be understood that various features and aspects of the disclosed embodiments can be combined with, or substituted for, one another in order to perform varying modes of the disclosure. Thus, it is intended that the scope of the present disclosure disclosed in FIGS. 12A-19D and the associated written disclosure should not be limited by the particular disclosed embodiments.

The following is claimed:

1. A luer connector comprising:
   a housing having a hollow bore, a first end, and a second end;
   a male luer tip supported by the housing configured to rotate with respect to the housing, the male luer tip having an opening in a first end thereof and a passageway through the male luer tip in fluid communication with the opening in the first end thereof; and
   an internal member extending into the passageway of the male luer tip toward the opening in the first end thereof, the internal member having an opening in a first end thereof and a passageway through the internal member in fluid communication with the opening in the first end thereof;
   wherein:
      the male luer tip is rotatable between a first position and a second position relative to the internal member;
      in the first position, the opening in the first end of the male luer tip is substantially offset with respect to the opening in the first end of the internal member so as to substantially prevent a flow of fluid through the male luer tip; and
      in the second position, the opening in the first end of the male luer tip is substantially aligned with respect to the opening in the first end of the internal member so that fluid is permitted to flow through the male luer tip.

2. The luer connector of claim 1, wherein the male luer tip is configured to rotate in a first direction with respect to the housing from the first position to the second position as a female connector is threadedly connected to the luer connector.

3. The luer connector of claim 1, wherein the male luer tip is configured to rotate in a second direction with respect to the housing from the second position to the first position as a female connector is threadedly disconnected from the luer connector.

4. The luer connector of claim 1, wherein the internal member is rotationally fixed relative to the housing.

5. The luer connector of claim 1, wherein the internal member comprises an axial opening through at least a portion of the internal member, the axial opening being in fluid communication with the opening in the first end of the internal member.

6. The luer connector of claim 1, wherein the luer tip is biased toward the first position.

7. The luer connector of claim 1, wherein the male luer tip has a conically shaped outside surface.

8. The luer connector of claim 1, wherein the luer connector is configured such that the male luer tip is prevented from rotating beyond the first or the second position.

9. A medical connector, comprising:
   a substantially rigid housing having a first end and a second end, said first and second ends being connected by a selectively closable fluid passageway;
   said first end including a hollow male luer with an inner surface, a first open end, and a second base end;
   a first valve member supported substantially within the housing, the first valve member being configured to selectively seal an opening adjacent to the first end of the housing at the tip of the male luer when the connector is in a closed position;
   wherein the first valve member is formed with a single strut member extending axially along at least a portion of the valve member and displaced from the valve member, said strut member extending through an opening in the housing and including a sealing member such that said strut member is configured to sealingly engage said housing as said strut member moves axially through said opening; and
   an internal chamber within the housing and extending outside the male luer, the chamber being fluidly coupled with at least a portion of the hollow male luer, the chamber having a first volume in the connector closed position and a second volume smaller than the first volume when the connector is in an open position.

\* \* \* \* \*